(12) United States Patent
Alessi et al.

(10) Patent No.: US 7,897,371 B2
(45) Date of Patent: Mar. 1, 2011

(54) ACTIVATION OF MUTATED RAC-PK

(75) Inventors: Dario Alessi, Dundee (GB); Mirjana Andjelkovic, Basel (CH); Philip Cohen, Invergowrie (GB); Peter David Cron, Basel (CH); Darren Cross, Macclesfield (GB); Brian A. Hemmings, Bettingen (CH)

(73) Assignee: Novartis AG (CH)

( * ) Notice: Subject to any disclaimer, the term of this patent is extended or adjusted under 35 U.S.C. 154(b) by 199 days.

(21) Appl. No.: 11/682,135

(22) Filed: Mar. 5, 2007

(65) Prior Publication Data
US 2008/0213240 A1    Sep. 4, 2008

Related U.S. Application Data

(63) Continuation of application No. 10/823,433, filed on Apr. 12, 2004, now abandoned, which is a continuation-in-part of application No. 10/673,091, filed on Sep. 26, 2003, now abandoned, which is a continuation of application No. 09/845,667, filed on Apr. 30, 2001, now abandoned, which is a continuation of application No. 09/091,763, filed as application No. PCT/GB96/03186 on Dec. 20, 1996, now abandoned, said application No. 10/823,433 is a continuation-in-part of application No. 10/147,123, filed on May 16, 2002, now abandoned, which is a continuation of application No. 09/542,646, filed on Apr. 3, 2000, now abandoned, which is a continuation of application No. 09/091,109, filed as application No. PCT/EP96/04811 on Nov. 5, 1996, now abandoned, said application No. 10/823,433 is a continuation-in-part of application No. 09/970,000, filed on Oct. 3, 2001, now abandoned, which is a continuation of application No. 09/068,702, filed as application No. PCT/EP96/04810 on Nov. 5, 1996, now abandoned.

(30) Foreign Application Priority Data

| Nov. 16, 1995 | (GB) | 9523379.7 |
| Dec. 15, 1995 | (GB) | 9525702.8 |
| Dec. 15, 1995 | (GB) | 9525704.4 |
| Dec. 20, 1995 | (GB) | 9526083.2 |
| May 16, 1996 | (GB) | 9610272.8 |
| Jul. 18, 1996 | (GB) | 9615066.9 |

(51) Int. Cl.
*C12N 9/12* (2006.01)
*C12Q 1/48* (2006.01)
*G01N 33/536* (2006.01)

(52) U.S. Cl. ............ 435/194; 435/69.1; 435/320.1; 435/252.3; 536/23.2; 424/94.5

(58) Field of Classification Search .................. None
See application file for complete search history.

(56) References Cited

U.S. PATENT DOCUMENTS 5,422,125 A * 6/1995 Skyler et al. .................. 424/646

OTHER PUBLICATIONS

Konishi et al. (1995) Biochem. Biophys. Res. Comm., vol. 216(2): 526-534.*
Alessi et al. (1996) EMBO J. 15(23): 6541-6551.*

* cited by examiner

*Primary Examiner* — Lisa J Hobbs
(74) *Attorney, Agent, or Firm* — Paul Paglierani

(57) ABSTRACT

The invention concerns RAC-PK and fragments thereof, as well as activators and inhibitors of RAC-PK for use as medicaments, particularly in the treatment of diseases concerned with abnormalities in processes modulated by insulin, such as cellular proliferation, insulin deficiency and/or excess blood sugar levels. Moreover, the invention provides RAC-PK for use in screening potential mimics or modulators thereof. A method for screening for agents capable of affecting the activity of GSK3 is also disclosed. The invention further provides a screening kit comprising the RAC-PK as an active principle, and a method for screening compounds which are candidate mimics or modulators of RAC-PK activity comprising detecting specific interactions between the candidate compounds and RAC-PK. There is also provided a process for activating RAC-PK comprising treatment thereof with a phosphatase inhibitor.

1 Claim, 21 Drawing Sheets

ACTIVATION OF MUTATED RAC-PK

This application is a continuation of application Ser. No. 10/823,433, Filing Date Apr. 12, 2004 now abandoned, which is a continuation-in-part of application (I) Ser. No. 10/673,091, Filing Date Sep. 26, 2003, now abandoned, which is a continuation of Ser. No. 09/845,667, filed Apr. 30, 2001, now abandoned, which is a continuation of Ser. No. 09/091,763, filed Jun. 19, 1998, now abandoned, which is a National Stage of PCT/GB96/03186, filed Dec. 20, 1996; (II) of application Ser. No. 10/147,123, filed May 16, 2002, now abandoned, which is a continuation of Ser. No. 09/542,646, filed Apr. 3, 2000, now abandoned, which is a continuation of Ser. No. 09/091,109, filed Jun. 11, 1998, now abandoned, which is a National Stage of PCT/EP96/04811, filed Nov. 5, 1996; and (III) of application Ser. No. 09/970,000, now abandoned, filed Oct. 3, 2001, which is a Continuation of Ser. No. 09/068,702, filed May 13, 1998, now abandoned, which is a National Stage of PCT/EP96/04810, filed Nov. 5, 1996.

The present invention relates to the control of glycogen metabolism and protein synthesis, in particular through the use of insulin. Particularly, the present invention is related to the use of RAC protein kinase (RAC-PK) as a therapeutic agent, as a ligand for screening molecules for a possible interaction with RAC-PK and to a method for identifying molecules involved in signal transduction. Further, the present invention relates to a method for producing an active form of a kinase involved in an insulin-dependent signaling pathway.

BACKGROUND OF THE INVENTION

Many people with diabetes have normal levels of insulin in their blood, but the insulin fails to stimulate muscle cells and fat cells in the normal way (type II diabetes). Currently it is believed that there is a breakdown in the mechanism through which insulin signals to the muscle and fat cells.

Protein phosphorylation and dephosphorylation are fundamental processes for the regulation of cellular functions. Protein phosphorylation is prominently involved in signal transduction, where extracellular signals are propagated and amplified by a cascade of protein phosphorylation and dephosphorylation. Two of the best characterized signal transduction, where extracellular signals are propagated and amplified by a cascade of protein phosphorylation and dephosphorylation. Two of the best characterized signal transduction pathways involve the c-AMP-dependant protein kinase (PKA) and protein kinase C(PKC). Each pathway uses a different second messenger molecule to activate the protein kinase, which, in turn, phosphorylates specific target molecules.

A novel subfamily of serine (Ser)/threonine (Thr) kinases has been recently identified and cloned, termed herein the RAC-PK [see Jones et al., Proc Natl Acad Sci USA, Vol. 88, No. 10, pp. 4171-4175 (1991); and Jones, Jakubowicz and Hemmings, Cell Regul, Vol. 2, No. 12, pp. 1001-1009 (1991)], but also known as RAC-PK or Akt. RAC kinases have been identified in two closely-related isoforms, RACα and RACβ, which share 90% homology at the gene sequence. Mouse RACα (c-akt) is the cellular homologue of the viral oncogene v-akt, generated by fusion of the Gag protein from the AKT8 retrovirus to the N-terminus of murine c-akt. Human RACβ is found to be involved in approximately 10% of ovarian carcinomas, suggesting an involvement of RAC kinases in cell growth regulation.

Another kinase implicated in cell growth control is S6 kinase, known as p70S6K. S6 kinase phosphorylates the 40S ribosomal protein S6, an event which up-regulates protein synthesis and is believed to be required in order for progression through the G1 phase of the cell cycle. The activity of p70S6K is regulated by Ser/Thr phosphorylation thereof, and it is itself a Ser/Thr kinase. The p70S6K signaling pathway is believed to consist of a series of Ser/Thr kinases, activating each other in turn and leading to a variety of effects associated with cell proliferation and growth. RAC-PK is believed to lie on the same signaling pathway as p70S6K, but upstream thereof.

RAC kinases contain an amino-terminal pleckstrin homology (PH) domain. See Haslam, Koide and Hemmings, Nature, Vol. 363, No. 6427, pp. 309-310 (1993). The PH domain was originally identified as an internal repeat, present at the amino and carboxy-termini of pleckstrin, a 47 kDa protein which is the major PKC substrate in activated platelets. See Tyers et al., Nature, Vol. 333, No. 6172, pp. 470-473 (1988). The superfamily of PH domain containing molecules consists of over 90 members including Ser/Thr kinases, e.g., RAC, Nrk, β-adrenergic receptor kinase (βARK) and PKC.mu.; tyrosine kinases, e.g., Bruton's tyrosine kinase (Btk), Tec and Itk; GTPase regulators, e.g., ras-GAP, ras-GRF, Vav, SOS and BCR; all known mammalian phospholipase Cs; cytoskeletal proteins, e.g., β-spectrin, AFAP-110 and syntrophin; "adapter" proteins, e.g., GRB-7 and 3BP2; and kinase substrates, e.g., pleckstrin and IRS-1.

While the PH domain structure has been solved for β-spectrin, dynamin and pleckstrin's amino-terminal domain, its precise function remains unclear. The presence of PH domains in many signaling and cytoskeletal proteins implicates it in mediating protein-protein and membrane interactions. Indeed, the PH domain of the βARK appears partly responsible for its binding to the β.gamma.-subunits of the heterotrimeric G-proteins associated with the β-adrenergic receptor, while the PH domain of the Btk appears to mediate an interaction with PKC. Several PH domains have been shown to be able to bind phosphatidyl-inositol-4-5-bisphosphate in vitro, although weakly.

IMPDH is a highly-conserved enzyme (41% amino acid identity between bacterial and mammalian sequences) involved in the rate-limiting step of guanine biosynthesis. In mammals there are two isoforms, 84% identical, called type I and type II which are differentially-expressed. See Natsumeda et al., J Biol Chem, Vol. 265, No. 9, pp. 5292-5295 (1990). Type I is constitutively-expressed at low levels while the type II mRNA and protein levels increase during cellular proliferation. IMPDH activity levels are also elevated during rapid proliferation in many cells. See Collart and Huberman, J Biol Chem, Vol. 263, No. 30, pp. 15769-15772 (1988).

By measuring the metabolic fluxes, the proliferative index of intact cancer cells has been shown to be linked with the preferential channeling of IMP into guanylate biosynthesis. Inhibition of cellular IMPDH activity results in an abrupt cessation of DNA synthesis and a cell-cycle block at the $G_1$-S interface. The specific inhibition of IMPDH by tiazofurin and the subsequent decline in the GTP pool, results in the down regulation of the G-protein ras, which is involved in many signal transduction pathways leading to cellular proliferation. For review see Avruch, Zhang and Kyriakis, Trends Biochem Sci, Vol. 19, No. 7, pp. 279-283 (1994).

Interestingly, p53 has been implicated in regulating IMPDH activity levels. See Sherley, J Biol Chem, Vol. 266, No. 36, pp. 24815-24828 (1991). Here a moderate over-expression of p53 (3- to 6-fold) induces a profound growth arrest which is rescued by purine nucleotide precursors. Indeed, the p53 over-expression induces a specific block in IMP to XMP conversion, and a diminished activity level of IMPDH. The p53 block does not affect the rate of RNA synthesis, nor is the phenotype rescued by deoxynucleotides indicating that a lack of precursors for DNA synthesis is also not the cause of the block. It would seem most likely that this effect is mediated through a down-regulation of the GTP pool required by G-proteins, such as ras.

The above observations suggest that IMPDH type II is primarily involved in producing XMP which is channeled into the GTP pool which is crucial for the regulation of G-proteins involved in signal transduction, such as ras. It may be that the type I enzyme provides a basal level of XMP that is channeled into the GTP/dGTP pools required for RNA and DNA synthesis. Changes in IMPDH type II activity would alter the GTP/GDP ratio by specifically altering the GTP component which could greatly affect ras signaling pathways as ras is sensitive to small changes in the GTP/GDP ratio.

Glycogen synthase kinase-3 (GSK3) is implicated in the control of several processes important for mammalian cell physiology, including glycogen metabolism and the control of protein synthesis by insulin, as well as the modulation of activity of several transcription factors, such as AP-1 and CREB. GSK3 is inhibited in vitro by serine phosphorylation caused by MAP kinase and p70.sup.S6K, kinases which lie on distinct insulin-stimulated signaling pathways.

GSK3 is responsible for serine phosphorylation in glycogen synthase, whose dephosphorylation underlies the stimulation of glycogen synthesis by muscle. Thus, GSK3 inactivates glycogen synthase, resulting in an increase in blood sugar levels. Insulin inhibits the action of GSK3, which, in combination with the concomitant activation of phosphatases which dephosphory late glycogen synthase, leads to the activation of glycogen synthase and the lowering of blood sugar levels.

GSK3 is inhibited in response to insulin with a half-time of 2 minutes, slightly slower than the half-time for activation of RAC-PKα (1 minute). Inhibition of GSK3 by insulin results in its phosphorylation at the same serine residue (serine 21) which is targeted by RAC-PKα in vitro. Like the activation of RAC-PKα, the inhibition of GSK3 by insulin is prevented by phosphatidyl inositol (PI-3) kinase inhibitors wortmannin and LY 294002. The inhibition of GSK3 is likely to contribute to the increase in the rate of glycogen synthesis [see Cross et al., Biochem J, Vol. 303, Pt. 1, pp. 21-26 (1994)] and translation of certain mRNAs by insulin. See Welsh et al., Biochem J, Vol. 303, Pt. 1, pp. 15-20 (1994).

We have used the yeast two-hybrid system [see Fields and Song, Nature, Vol. 340, No. 6230, pp. 245-246 (1989); and Chien, Bartel, Sternglanz and Fields, Proc Natl Acad Sci USA, Vol. 88, No. 21, pp. 9578-9582 (1991)] to determine if RAC-PK could function by forming specific interactions with other proteins. We have identified RAC-PK as interacting with human inosine-5' monophosphate dehydrogenase (IMPDH) type II, and with a novel protein termed RAC-PK Carboxy-Terminal Binding Protein (CTBP). RAC-PK stimulates IMPDH type II activity. In conjunction with the known role of IMPDH in GTP biosynthesis, our findings suggest a role for RAC-PK in the regulation of cell proliferation.

Moreover, using a peptide derived from GSK3 and GSK3 itself, we have been able to show that RAC-PK interacts with, phosphorylates and inactivates GSK3. This implicates RAC-PK in the regulation of insulin-dependent signaling pathways, which control cellular proliferation. Taken together, these results suggest a major involvement for RAC-PK in the control of insulin action.

Many growth factors trigger the activation of phosphatidylinositol (PI) 3-kinase, the enzyme which converts PI 4,5 bisphosphate (PIP2) to the putative second messenger PI 3,4,5 trisphosphate (PIP3) and RAC-PK lies downstream of PI 3-kinase. See Franke et al., Cell, Vol. 81, No. 5, pp. 727-736 (1995). RAC-PKα is converted from an inactive to an active form with a half-time of about 1 minute when cells are stimulated with PDGF [see Franke et al. (1995), supra], EGF or basic FGF [see Burgering and Coffer, Nature, Vol. 376, No. 6541, pp. 599-602 (1995)] or insulin [see Cross et al. (1995), supra; and Kohn, Kovacina and Roth, EMBO J, Vol. 14, No. 17, pp. 4288-4295 (1995)] or perpervanadate. See Andjelkovic et al., Proc Natl Acad Sci USA, Vol. 93, No. 12, pp. 5699-5704 (1996). Activation of RAC-PK by insulin or growth factors is prevented if the cells are pre-incubated with inhibitors of PI 3-kinase (wortmannin or LY 294002) or by over-expression of a dominant negative mutant of PI 3-kinase. See Burgering and Coffer (1995), supra. Mutation of the tyrosine residues in the PDGF receptor that when phosphorylated bind to PI 3-kinase also prevent the activation of RAC-PKα. See Burgering and Coffer (1995), supra; and Franke et al. (1995), supra.

When isolated from natural sources, especially convenient sources, such as tissue culture cells, RAC-PK and other signaling kinases are normally in the inactive state. In order to isolate active PKs, it is necessary to stimulate cells in order to switch on the signaling pathway to yield active kinase. Moreover, when cells expressing kinase enzymes are used in kinase activity assays, it is necessary to employ activating agents prior to conducting the assay. Thus, cells are normally stimulated with mitogens and/or activating agents, such as IL-2, platelet-derived growth factor (PDGF), insulin, epidermal growth factor (EGF) and basic fibroblast growth factor (bFGF). Such agents are expensive and, when it is desired to produce active kinases or to activate cells in large amounts, the use of such agents is disadvantageous.

Screening of candidate compounds for activity as inhibitors of RAC-PK, or other signaling kinases in order to identify candidate immunosuppressive or anti-proliferative agents requires a plentiful supply of PK. Using modern day technology, it is possible to produce large quantities of virtually any desired protein in recombinant DNA expression systems. In the case of kinases, such as those with which we are presently concerned, however, such systems are unsatisfactory because the proteins produced would be unphosphorylated and therefore inactive. There is therefore a requirement to identify a cost-effective way to produce phosphorylated PKs which can be employed in screening procedures.

It is known [see Jano et al., Biochemistry, Vol. 85, pp. 406-410 (1988)] that vanadate can activate p70S6K itself. The mechanism of this activation, however, is not known. We have now found that vanadate acts generally on signaling kinases, activating them and preventing deactivation by phosphatases. Moreover, we have found that okadaic acid, a different class of compound from vanadate which interacts with different proteins, may be used to similar effect.

BRIEF DESCRIPTION OF THE DRAWINGS

In FIG. 1(b), L6 myotubes were stimulated with insulin for the times indicated with (filled triangle) or without (filled circles) a 15 minutes pre-incubation with LY 294002. The open circles show experiments from insulin-stimulated cells where GSK3 was assayed after reactivation with PP2A. In FIG. 1(c), cells were incubated with rapamycin (triangles) or rapamycin plus PD 98059 (circles) before stimulation with insulin, and GSK3 activity measured before (filled symbols) and after (open symbols) pretreatment with PP2A.

In FIG. 4(a), GSK3-β was maximally inactivated by incubation with RAC-PK and Mg-[γ-$^{32}$P]ATP and after SDS-PAGE, the $^{32}$P-labelled GSK3-β ($M_r$ 47K was digested with trypsin[11] and chromatographed on a C18-column. Fractions (0.8 mL) were analyzed for $^{32}$P-radioactivity (open circles), and the diagonal line shows the acetonitrile gradient.

In FIG. 4(b), the major phosphopeptide from a (400 c.p.m.) was subjected to solid-phase sequencing, and $^{32}$P-radioactivity released after each cycle of Edman degradation is shown.

In FIG. 4(c), GSK3-α and GSK3-β were co-immunoprecipitated from the lysates of $^{32}$P-labelled cells, denatured in SDS, subjected to SDS-PAGE, transferred to nitrocellulose and autoradioqraphed. In lanes 1-3, GSK3 isoforms immunoprecipitated from unstimulated cells; in lanes 4-6, GSK3 isoforms immunoprecipitated from insulin-stimulated cells.

In FIG. 4(d), GSK3 isoforms from (c) were digested with trypsin, and the resulting phosphopeptides separated by isoelectric focusing and identified by auto-radiography. Lanes 1 and 4 show the major phosphopeptide resulting from in vitro phosphorylation of GSK3-β by RAC-PK and MAPKAP kinase-1, respectively; lanes 2 and 5, the phosphopeptides obtained from GSK3-β and GSK3-α, immunoprecipitated from unstimulated cells; lanes 3 and 6, the phosphopeptides obtained from GSK3-β and GSK3-α immunoprecipitated from cells stimulated for 5 minutes with 0.1 μM insulin; the arrow denotes the peptides whose phosphorylation is increased by insulin. The PI values of two markers, Patent Blue (2.4) and azurin (5.7) are indicated.

In FIG. 7(a), peptides A and B from FIG. 5(b) (1000 cpm) were incubated for 90 minutes at 110° C. in 6 M HCl, electrophoresed on thin layer cellulose at PH 3.5 to resolve orthophosphate (Pi), phosphoserine (pS), phosphthreonine (pT) and phosphotyrosine (pY) and autoradioqraphed.

FIG. 8(b) shows 20 µof protein from each lysate was electrophoresed on a 10% SDS/polyacrylamide gel and immunoblotted using monoclonal HA-antibody. The molecular markers are those used in FIG. 5(b).

In FIG. 11(a), 0.5 µg of immunoprecipitated HA-RAC-PKα was incubated with MAPKAP kinase-2 (50 U/mL), 10 mM magnesium acetate and 100 mM [γ$^{32}$P] ATP in a total of 40 µL of Buffer B. At various times, aliquots were removed and either assayed for RAC-PKα activity (open circles) or for incorporation of phosphate into RAC-PKα (closed circles). Before measuring RAC-PKα activity, EDTA was added to a final concentration of 20 mM to stop the reaction, and the immunoprecipitates washed twice with 1.0 mL of buffer B containing 0.5 M NaCl, then twice with 1.0 mL of buffer B to remove MAPKAP kinase-2. The results are presented as ±SEM for 6 determinations (2 separate experiments) and RAC-PKα activities are presented relative to control experiments in which HA-RAC-PKα was incubated with MgATP in the absence of MAPKAP kinase-2 (which caused no activation). Phosphorylation was assessed by counting the $^{32}$P-radioactivity associated with the band of RAC-PKα after SDS/polyacrylamide gel electrophoresis. The open triangles show the activity of immunoprecipitated HA-KD RAC-PKα phosphorylated by MAPKAP kinase-2.

In FIG. 11(b), HA-RAC-PKα phosphorylated for 1 hour with MAPKAP kinase-2 and $^{32}$P-γ-ATP as in (a) was digested with trypsin and chromatographed on a C18-column as described in the legend for FIG. 2(c). The major $^{32}$P-labelled peptide from (b) was analyzed on the 470A sequencer as in FIG. 3 to identify the site of phosphorylation.

In FIG. 12(a), WT and mutant HA-RAC-PKα proteins were immunoprecipitated from the lysates of unstimulated COS-1 cells expressing these constructs and incubated for 60 minutes with MgATP in the absence (−, filled bars) or presence (+, hatched bars) of MAPKAP kinase-2 and MgATP (50 U/mL). The RAC-PKα protein was expressed as similar levels in each construct and specific activities are presented relative to WT HA-RAC-PKα incubated in the absence of MAPKAP kinase-2 (0.03 U/mg). The results are shown as the average ±SEM for 3 experiments.

In FIG. 12(b), 20 µg of protein from each lysate was electrophoresed on a 10% SDS/polyacrylamide gel and immunoblotted using monoclonal HA-antibody. After incubation with MAPKAP kinase-2 and MgATP, the activity of HA-308D RAC-PKα was nearly 5-fold higher than that of WT HA-RAC-PKα phosphorylated at Ser473. These results suggested that the phosphorylation of either Thr308 or Ser473 leads to partial activation of RAC-PKα in vitro, and that phosphorylation of both residues results in a synergistic activation of the enzyme.

FIG. 20 depicts the effect of Ro 318220 and GF 109203× on PKs activated by growth factors, cytokines and cellular stresses. FIG. 20(a) shows the mixed isoforms of PKC were potently inhibited by Ro 318220 with an $IC_{50}$ of 5 nM in the assay. In contrast, a number of PKs activated by growth factors (c-Rafl, MAPKK-1 and p42 MAP kinase) and 1 PK that is activated by cellular stresses and proinflammatory cytokines (MAPKAP-K2) were not inhibited significantly by Ro 318022 in vitro.

FIG. 20(b) shows that PK B, an enzyme that is activated in response to insulin and growth factors, was inhibited by Ro 318220 ($IC_{50}$ of 1 μM), similar to the $IC_{50}$ for PKα.

SUMMARY OF THE INVENTION

Figure 1:
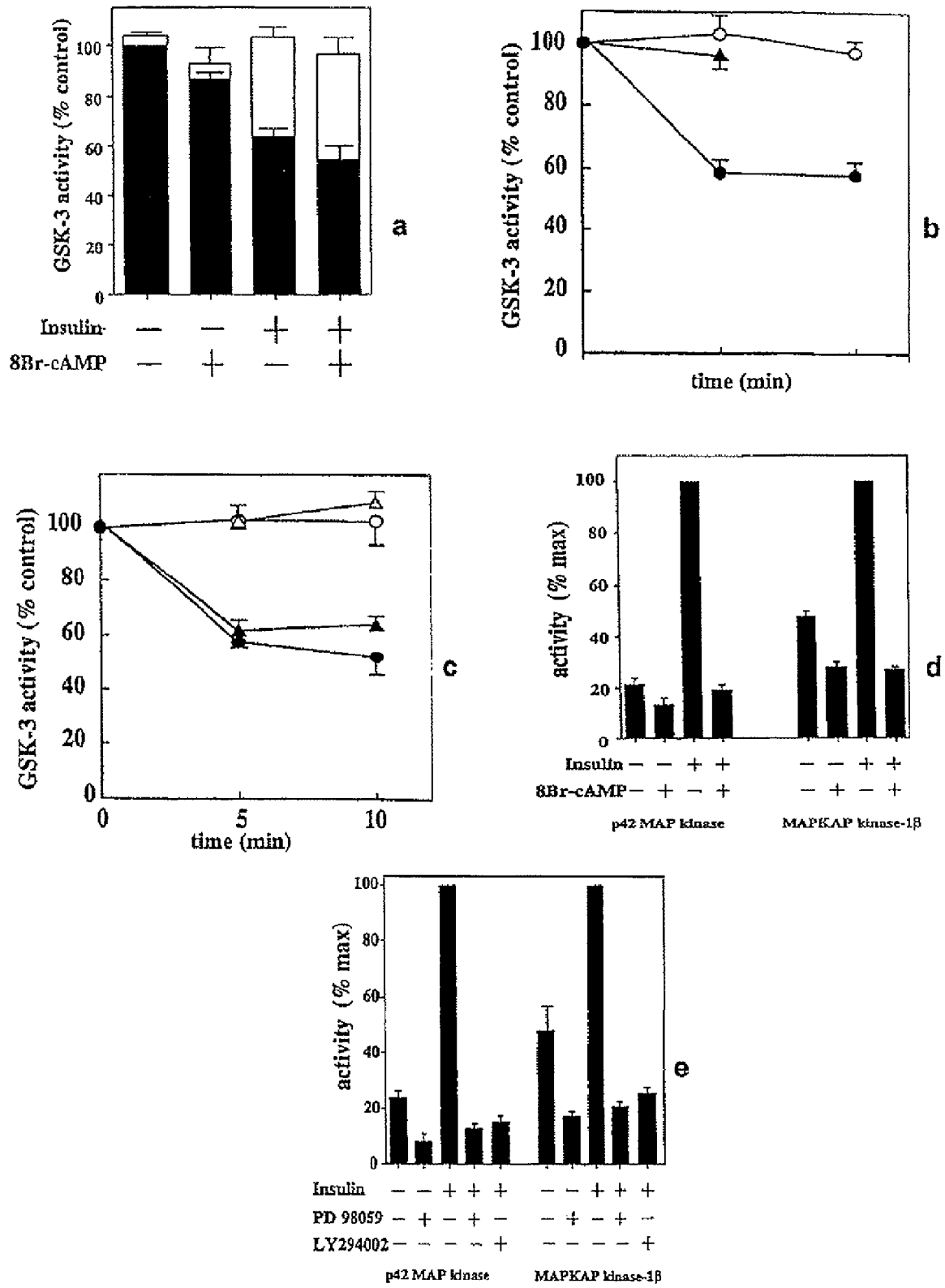
FIG. 1(a) depicts the co-immunoprecipitation of two GSK3 isoforms before (black bars) and after (white bars) reactivation with PP2A. The results are presented relative to the activity in unstimulated cells, which was 0.08±0.006 U mg$^{-1}$ (n=10).
FIGS. 1(b) and 1(c) depict the inhibition of GSK3 by insulin, which is unaffected by rapamycin and PD 98059, but prevented by LY 294002.
FIGS. 1(d) and 1(e) depict the immunoprecipitation of p42 MAP kinas and MAPKAP kinase-1β, after incubation with 8Br-cAMP (15 minutes), PD 98059 (60 minutes) or LY 294002 (15 minutes) and then with insulin.

According to the invention, there is provided RAC-PK and fragments, analogues, isoforms and functional equivalents thereof, as well as activators and inhibitors of RAC-PK for use in the treatment of diseases concerned with abnormalities in processes modulated by insulin, such as cellular proliferation, insulin deficiency and/or excess blood sugar levels, e.g., in the treatment of type II diabetes and cancer, such as ovarian, breast and pancreatic cancer. Moreover, the invention provides RAC-PK for use in screening potential mimics or modulators thereof. The invention further provides a screening kit comprising the RAC-PK as an active principle, and a method for screening compounds which are candidate mimics or modulators of RAC-PK activity comprising detecting specific interactions between the candidate compounds and RAC-PK.

The present invention also provides a novel peptide comprising the amino acid sequence Arg-xaa-Arg-Yaa-zaa-Ser/Thr-Hyd, where Xaa is any amino acid, Yaa and Zaa are any amino acid [preferably not glycine (Gly)] and Hyd is a large hydrophobic residue, such as Phe or Leu, or a functional equivalent thereof. The invention also provides a method for screening for substances which inhibit the activation of RAC-PK in vivo by preventing its interaction with PIP3 or P13,4-bisP. Thus the invention also provides a method of determining the ability of a substance to affect the activity or activation of RAC-PK. The method of the invention can also be used for identifying activators or inhibitors of GSK3. The invention also provides a method for screening for inhibitors or activators of enzymes that catalyze the phosphorylation of RAC-PK.

There is also provided a process for producing an active form of a kinase involved in an insulin dependent signaling pathway.

DETAILED DESCRIPTION OF THE PREFERRED EMBODIMENTS

In a first aspect, the invention provides RAC-PK or a fragment thereof, or a modulator thereof except vanadate and wortmannin, for use as a medicament.

Vanadate, which term as used herein includes various forms thereof, such as ortho- and metavanadate, pervanadate and other related vanadium ions, is known as a therapeutic agent in the treatment of diabetes. See, e.g., U.S. Pat. No. 5,421,125, European Patent Application Nos. 0521787, 0264278 and 0245979. In UK Patent Application No. 9525702.8 (Ciba-Geigy AG), filed Dec. 15, 1995, it is disclosed that vanadate is a potent activator of kinases of the insulin-stimulated signaling pathways and of RAC-PK in particular. Accordingly vanadate exerts its therapeutic effect on diabetes by stimulating RAC, which phosphorylates GSK3 and deactivates it, leading to a lowering in blood sugar levels.

RAC-PK and activators thereof are therefore useful in the treatment of diabetes and other diseases where blood sugar levels are excessive. Conversely, inhibitors of RAC-PK, such as wortmannin and okadaic acid are useful in the treatment of diseases involving insufficiency in blood sugar levels.

In the present invention, RAC-PK may be any isoform of RAC-PK as described in the literature, from any species. Human RAC-PK is preferred. Human RAC-PKα is represented in SEQ ID NO. 3. Domains of RAC-PK are the individual functional portions thereof, such as the PH domain, the catalytic domain and the C-terminal domain. Fragments of RAC, which include domains of RAC, are functionally-active portions of the RAC-PK which may be used in the present invention in place of RAC. Fragments of RAC-PK are preferably the domains thereof, advantageously the PH domain, the catalytic domain and the C-terminal domain. In each case, the terminology used embraces mutants and derivatives of RAC-PK and its fragments which can be created or derived from the naturally-occurring protein according to available technology. For instance, nucleic acids encoding RAC-PK may be mutated without affecting the nature of the peptide encoded thereby, according to the degeneracy of the amino acid code. Moreover, conservative amino acid substitutions may be made in RAC-PK or a fragment thereof, substantially without altering its function. Further additions, deletions and/or substitutions which improve or otherwise alter the function of RAC-PK or a fragment thereof are envisaged and included within the scope of the invention.

The invention also provides the use of RAC-PK or a fragment thereof, or a modulator of RAC-PK activity, except vanadate, for the preparation of a medicament for use in the treatment of diseases involving an anomaly in blood sugar levels, such as diabetes.

Moreover, the invention provides the use of RAC-PK or a fragment thereof, or a modulator of RAC-PK activity, except wortmannin, for the preparation of a medicament for use in the treatment of abnormalities in cellular proliferation.

The antibiotic wortmannin, which is known to inhibit phosphatidylinositol 3-OH kinase (PI-3K) activation, targets signal transduction and indirectly inactivates inter alia RAC, possibly via PI-3K. Wortmannin has been indicated in the treatment of neoplastic conditions. However, the broad involvement of the various isoforms of RAC-PK in mitogenic signal transduction, as well as insulin-dependent signaling has hitherto not been known. We have now shown that RAC-PK is involved in the regulation of both GSK3 and IMPDH, a factor involved in growth control. It can be concluded, therefore, that RAC-PK plays a central role in growth control.

Therapeutic agents according to the invention may be formulated conventionally, according to the type of agent. Where the agent is a salt, such as vanadate, it is conveniently formulated in aqueous solution at neutral pH and administered orally at room temperature. In the case of a peptide medicament, such as RAC-PK itself, more elaborate delivery techniques, such as liposomal delivery, may be required in order to introduce the peptide into target cells. Delivery systems for peptide therapeutics are documented in the art.

The identification of RAC-PK as a major mediator in growth control permits the design of screening systems to identify putative therapeutic agents for use in treating anomalies of growth control. Thus, in a second aspect of the invention there is provided a method for screening potential modulators of intracellular signaling comprising the steps of:

(a) incubating RAC-PK or a fragment thereof with the compound to be screened; and (b) detecting interaction between the compound and RAC.

The screening may be carried out using complete RAC-PK or a fragment thereof. In particular, it has been shown that the PH domain of RAC-PK is important in mediating many of its effects, as set out, e.g., in UK patent application No. 9525703.6 (Ciba-Geigy AG), filed Dec. 15, 1995. Moreover, as disclosed hereinbelow, RAC-PK interacts with IMPDH via the PH domain. The interaction is not observable in the yeast two-hybrid system if complete RAC-PK is used, although in vitro binding of RAC-PK to IMPDH occurs.

Interactions also occur between other fragments of RAC-PK and its physiological targets and regulators. For example, GSK3 binds to RAC-PK via the catalytic domain, as evidenced by the phosphorylation of GSK3 by RAC. CTBP, on the other hand, does not bind the catalytic or PH domains but binds specifically to the carboxy terminal domain of RAC.

Preferably, therefore, the invention includes incubating the compound to be screened with a fragment of RAC, which is advantageously the PH domain, the catalytic domain or the carboxy terminal domain.

RAC-PK fragments for use in the method of the present invention may be in the form of isolated fragments, or in the form of the fragment complexed with further polypeptides. For example, in the case of the two-hybrid system, the fragment is complexed to a DNA binding or transcriptional activation domain derived from another protein, such as the yeast activator GAL4.

Moreover, the RAC-PK used in the method of the invention may be in the form of a mutant thereof, e.g., a constitutively activated kinase. An important activating residue is T308, present in the so-called T-loop between subdomains 7 and 8 of the kinase. A general guide to kinase structure is given in Woodgeft, Protein Kinases, IRL Press, UK (1994). Substitution of T308 with aspartic acid results in a clear increase in basal activity of the kinase, which however retains a potential for further activation. The invention therefore provides a RAC-PK in which Thr308 has been mutated to Asp.

Preferably, Ser473 is additionally mutated to Asp. Phosphorylation of this residue is required for full activation of RAC-PK in vivo, and the T308/S473 double mutant (both residues converted to Asp) shows a constitutive activity 18-fold higher than native RAC-PK. The double mutant is not susceptible to further activation.

The mutations may be carried out by means of any suitable technique. Preferred, however, is in vitro site-directed mutagenesis of a nucleotide sequence encoding RAC and subsequent expression of RAC in a recombinant DNA expression system. This method is an in vitro mutagenesis procedure by which a defined site within a region of cloned DNA can be altered. See Zoller and Smith, Methods Enzymol, Vol. 100, pp. 468-500 (1983); and Botstein and Shortle, Science, Vol. 229, No. 4719, pp. 1193-1201 (1985). Methods for site-directed mutagenesis are well-known to those of skill in the art, as exemplified by Sambrook et al., Molecular Cloning—A Laboratory Manual, Cold Spring Harbor, N.Y., USA (1989), and the number of commercially-available in vitro mutagenesis kits.

The compound to be screened may be present in essentially pure, uncomplexed form, or may be complexed with chemical groups or further polypeptides. In the case of the two hybrid system, it is complexed to a DNA binding or transcriptional activation domain, in order to complement the PH domain.

Isolated PH domain for use in the present invention may be prepared as set forth in UK patent application No. 9525705.1 (Ciba-Geigy AG), filed Dec. 15, 1995. Where a small quantity of PH domain suffices, however, PH domain may be obtained by expressing a nucleic acid sequence encoding it in bacterial cell culture in the form of a fusion protein which is subsequently cleaved according to techniques known in the art. For example, amino acids 1-131 of RAC, which encode the PH domain, may be expressed as a fusion protein, advantageously with glutathione-S-transferase (GST), subsequently cleaving the fusion protein with thrombin and isolating the domain by protein purification techniques, such as FPLC. This method gives a relatively small yield of pure soluble PH domain.

Carboxy and kinase domains are likewise advantageously synthesised as fusion proteins, for instance as GST fusions.

RAC-PK or a fragment thereof for use in the present invention may be prepared as set forth in UK patent application No. 9525702.8. Alternatively, RAC-PK may be expressed in recombinant cell culture. Baculovirus vectors, specifically intended for insect cell culture, are especially preferred and are widely obtainable commercially, e.g., from Invitrogen and Clontech. Other virus vectors capable of infecting insect cells are known, such as Sindbis virus. See Hahn, Hahn, Braciale and Rice, Proc Natl Acad Sci USA, Vol. 89, No. 7, pp. 2679-2683 (1992). The baculovirus vector of choice [reviewed by Miller, Ann Rev Microbiol, Vol. 42, pp. 177-199 (1988)] is *Autographa californica* multiple nuclear polyhedrosis virus (AcMNPV).

Typically, the heterologous gene replaces at least in part the polyhedrin gene of AcMNPV, since polyhedrin is not required for virus production. In order to insert the heterologous gene, a transfer vector is advantageously used. Transfer vectors are prepared in *E. coli* hosts and the DNA insert is then transferred to AcMNPV by a process of homologous recombination. Baculovirus techniques useful in the present invention are standard and well-known in the art. See O'Reilly et al., Baculovirus expression vectors; A laboratory manual, Oxford University Press Inc., New York (1994), as well as in literature published by suppliers of commercial baculovirus kits, e.g., Pharmingen.

Incubation conditions will vary according to the precise method used to detect the interaction between the PH domain and the screened compound. In the case of transcription activation detection systems, such as the yeast two-hybrid system, incubation conditions are suitable for gene transcription, such as those prevailing inside a living cell. Other detection systems, however, will require different incubation conditions. For example, if the detection of interaction is based on relative affinity in a chromatographic assay, e.g., as is known in affinity chromatography, conditions will be adjusted to promote binding and then gradually altered, such that the point at which the screened compound no longer binds to the RAC-PK PH domain may be determined.

The detection method may employ the natural fluorescence of tryptophan at position 22 ($Trp^{22}$) in the RAC-PK PH domain, which is inhibited by certain interactions with the domain, as set forth in UK patent application No. 9525703.6. Briefly, fluorescence of the amino-terminal Trp residue in the PH domains of certain PH domain containing proteins may be detected by exciting the molecule to fluoresce at the appropriate frequency and monitoring the emission. The N-terminal $Trp^{22}$ of RAC, e.g., fluoresces at 345 nm when excited at 290 nm. Techniques for monitoring protein fluorescence are widely-known in the art. We have shown that the PH domain of RAC-PK binds phospholipid with high affinity, which suggests that RAC-PK may be membrane-bound in vivo via the PH domain. Binding of phospholipid to the RAC-PK PH domain quenches the natural fluorescence of the N-terminal $Trp^{22}$. Interaction of the PH domain with the cell membrane is believed to be important for the stable interaction of RAC-PK with membrane bound partners in signaling pathways, such that disruption of this interaction will lead to modulation of the signaling effect through the dissociation of the signaling molecule from the cell membrane. The modulation could be either down-regulating, e.g., if the otherwise stable interaction of the molecule with membrane-bound partners is a stimulatory interaction, or up-regulating, in the event that the interaction is an inhibitory interaction. Accordingly, a compound which is a candidate modulator of signal response may be screened for by means of a method comprising the steps of:

(a) incubating the compound with the PH domain of a signaling molecule which is capable of fluorescing; and (b) determining the phospholipid-induced modulation in the fluorescence of the PH domain, an alteration of the fluorescence in the presence of the compound being indicative of a functional interaction between the compound and the PH domain.

In this case, the incubation conditions will be adjusted to facilitate the detection of fluorescence at 345 nm when the PH domain is excited at a frequency of 290 nm.

Incubation according to the invention may be achieved by a number of means, but the basic requirement is for RAC-PK or a fragment thereof and the screened compound to be able to come into contact with each other. This may be achieved by admixing RAC-PK or a fragment thereof and the compound, or by producing them in situ, such as by expression of nucleic acids encoding them. Where the RAC-PK or RAC-PK fragment and/or the compound are in the form of fusions with other polypeptides, they may be expressed as such in situ.

Preferably, the method of the invention is based on a two-hybrid system. Such systems detect specific protein:protein interactions by exploiting transcriptional activators having separable DNA-binding and transcription activating domains, such as the yeast GAL4 activator. A reporter gene is operatively linked to an element responsive to the transcriptional activator being used, and exposed to RAC-PK or a fragment thereof and the compound to be screened, one of which is complexed to the transcription activating domain of the transcriptional activator and the other of which is joined to the DNA binding domain thereof. If there is a specific interaction between RAC-PK or a fragment thereof and the compound, the DNA binding and transcription activating domains of the transcriptional activator will be brought into juxtaposition and transcription from the reporter gene will be activated.

Alternatively, the detection may be based on observed binding between RAC-PK or a fragment thereof, such as its PH domain or its catalytic domain, and the screened compound, or a fragment thereof. For example, the interaction between RAC-PK and the insulin mediator GSK3 is detected hereinbelow by monitoring the interaction of a peptide surrounding the major phosphorylation site of GSK3 known to be responsible for its inactivation with RAC-PK. In a similar manner, the involvement of RAC-PK on the activation or inactivation of a particular compound may be screened for by monitoring the interaction of a portion thereof known to be involved in modulation events with RAC.

RAC-PK or a fragment thereof may be used to screen for compounds which bind thereto by incubating it with the compound to be screened and subsequently "pulling down" RAC-PK complexes with a RAC-specific antibody. Antibodies suitable for immunoprecipitation or immuno-affinity chromatography may be prepared according to conventional techniques, known to those of ordinary skill in the art, and may be monoclonal or polyclonal in nature. For example, see Lane et al., EMBO J, Vol. 11, No. 5, pp. 1743-1749 (1992). After the RAC-compound complex has been isolated by affinity, the compound may be dissociated from the RAC-PK antibody and characterised by conventional techniques.

The interaction of RAC-PK or a fragment thereof with the screened compound may also be observed indirectly. For example, an inhibitor or activator of RAC-PK function may be detected by observing the effects of RAC-PK on a substrate in the presence or absence of the compound.

The activity of RAC-PK or the catalytic domain thereof may be assessed by means of a kinase activity assay, employing a substrate for the kinase. For example, myelin basic protein (MBP) may be used, in accordance with established assay procedures. Physiological substrates, such as GSK3, may also be used. Alternatively, RAC-PK activity may be assessed by determining the degree of activating phosphorylation of RAC-PK itself. Advantageously, phosphorylation on residues normally implicated in kinase activation is assessed.

RAC-PK, as disclosed in UK patent application No. 9525702.8, is preferentially activated by phosphorylation at Ser and Thr residues.

The assay of the invention may be used to measure the direct effect of the candidate compound on RAC, or it may be used to determine the effect of the compound on a kinase acting upstream thereof in a signaling pathway. In the latter situation, RAC-PK acts as a substrate for the upstream kinase and the activity of the upstream kinase is assessed by determining the phosphorylation state or the activity of RAC-PK.

In order to obtain a meaningful result, the activity of RAC-PK exposed to the candidate immunosuppressive or antiproliferative agent should be compared to the activity of RAC-PK not exposed to the agent, a modulation of RAC-PK activity being indicative of potential as a modulator of cell proliferation and/or insulin signal transduction.

Promising compounds may then be further assessed by determining the properties thereof directly, for instance, by means of a cell proliferation assay. Such an assay preferably involves physical determination of proliferation in cells which have been subjected to kinase activation by a phosphatase inhibitor, exposed to the candidate RAC-PK modulator and optionally subsequently stimulated with a mitogen, such as a growth factor, IL-2 or PMA. More simply, the assay may involve exposure of unstimulated cells to the candidate modulator, followed by stimulation with a phosphatase inhibitor.

The invention further comprises the use of RAC-PK or a fragment thereof in a screening system. The screening system is preferably used to screen for compounds which are modulators of insulin activity, particularly where that activity is related to glycogen metabolism or cell proliferation.

Kits useful for screening such compounds may be prepared, and will comprise essentially RAC-PK or a fragment thereof together with means for detecting an interaction between RAC-PK and the screened compound. Preferably, therefore, the screening kit comprises one of the detection systems set forth hereinbefore.

RAC-PK for use in kits according to the invention may be provided in the form of a protein, e.g., in solution, suspension or lyophilised, or in the form of a nucleic acid sequence permitting the production of RAC-PK or a fragment thereof in an expression system, optionally in situ. Preferably, the nucleic acid encoding RAC-PK or a fragment thereof encodes it in the form of a fusion protein, e.g., a GST fusion.

In a still further embodiment, the invention provides a compound which interacts directly or indirectly with RAC-PK or a fragment thereof. In the case of indirectly acting compounds, agents, such as insulin and wortmannin, are excluded. Such a compound may be inorganic or organic, e.g., an antibiotic, and is preferably a proteinaceous compound involved in intracellular signaling. For example, the compound may be CTBP (SEQ ID NOs: 1 and 2).

Compounds according to the invention may be identified by screening using the techniques described hereinbefore, and prepared by extraction from natural sources according to established procedures, or by synthesis, especially in the case of low molecular weight chemical compounds. Proteinaceous compounds may be prepared by expression in recombinant expression systems, e.g., a baculovirus system as described hereinbefore or in a bacterial system, e.g., as described in UK patent application No. 9525705.1. Proteinaceous compounds are mainly useful for research into the function of signaling pathways, although they may have a therapeutic application.

Low molecular weight compounds, on the other hand, are preferably produced by chemical synthesis according to established procedures. They are primarily indicated as therapeutic agents. Low molecular weight compounds and organic compounds in general may be useful as insulin mimics or anti-proliferative agents.

The present invention further provides the use of RAC-PK, its analogues, isoforms, inhibitors, activators and/or the functional equivalents thereof to regulate glycogen metabolism and/or protein synthesis, in particular, in disease states where glycogen metabolism and/or protein synthesis exhibits abnormality, e.g., in the treatment of type II diabetes; also in the treatment of cancer, such as ovarian, breast and pancreatic cancer. A composition comprising such agents is also covered by the present invention, and the use of such a composition for treatment of disease states where glycogen metabolism and/or protein synthesis exhibit abnormality.

The present invention also provides a novel peptide comprising the amino acid sequence Arg-xaa-Arg-Yaa-zaa-Ser/Thr-Hyd, where Xaa is any amino acid, Yaa and Zaa are any amino acid (preferably not Gly), and Hyd is a large hydrophobic residue, such as Phe or Leu, or a functional equivalent thereof. Represented in single letter code, a suitable peptide would be RXRX'X'S/TF/L, where X' can be any amino acid, but is preferably not Gly; Gly can in fact be used, but other amino acids are preferred. Typical peptides include GRPRTSSFAEG (SEQ ID NO: 5), RPRAATC (SEQ ID NO: 6) or functional equivalents thereof. The peptide is a substrate for measuring RAC-PK activity.

The invention also provides a method for screening for substances which inhibit the activation of RAC-PK in vivo by preventing its interaction with PIP3 or PI3,4-bisP.

Thus the invention also provides a method of determining the ability of a substance to affect the activity or activation of RAC-PK, the method comprising exposing the substance to RAC-PK and phosphatidyl inositol polyphosphate, i.e., PIP3 or PI3,4-bisP, etc) and determining the interaction between RAC-PK and the phosphatidyl inositol polyphosphate. The interaction between RAC-PK and the phosphatidyl inositol polyphosphate can conveniently be measured by assessing the phosphorylation state of RAC-PK, preferably at T308 and/or S473, e.g., by measuring transfer of radiolabelled .sup.32P from the PIP3, e.g., to the RAC-PK and/or by SDS-PAGE.

The method of the invention can also be used for identifying activators or inhibitors of GSK3, such a method can comprise exposing the substance to be tested to GSK3, and optionally, a source of phosphorylation, and determining the state of activation of GSK3, optionally by determining the state of its phosphorylation. This aspect of the invention can be useful for determining the suitability of a test substance for use in combating diabetes, cancer, or any disorder which involves irregularity of protein synthesis or glycogen metabolism.

The invention also provides a method for screening for inhibitors or activators of enzymes that catalyse the phosphorylation of RAC-PK, the method comprising exposing the substance to be tested to:

(a) one or more enzymes upstream of RAC-PK;

(b) RAC-PK; and optionally (c) nucleoside triphosphate and determining whether, and optionally to what extent the RAC-PK has been phosphorylated on T308 and/or S473.

Also provided is a method of identifying agents able to influence the activity of GSK3, said method comprising:

(a) exposing a test substance to a substrate of GSK3; and (b) detecting whether, and optionally, to what extent said peptide has been phosphorylated.

The test substance may be an analogue, isoform, inhibitor or activator of RAC-PK, and the above method may be modified to identify those agents which stimulate or inhibit RAC-PK itself. Thus such a method may comprise the following steps:

(a) exposing the test substance to a sample containing RAC-PK, to form a mixture;

(b) exposing said mixture to a peptide comprising the amino acid sequence defined above or a functional equivalent thereof (usually in the presence of Mg.sub.2+ and ATP); and (c) detecting whether, and optionally, to what extent said peptide has been phosphorylated.

In this aspect, the method of the invention can be used to determine whether the substance being tested acts on RAC-PK or directly on GSK3. This can be done by comparing the phosphorylation states of the peptide and RAC-PK; if the phosphorylation state of GSK3 is changed but that of RAC-PK is not then the substance being tested acts directly on GSK3 without acting on RAC-PK. In a further aspect, the present invention provides a method of treatment of the human or non-human, preferably mammalian, animal body, said method comprising administering RAC-PK, its analogues, inhibitors, stimulators or functional equivalents thereof to said body. Said method affects the regulation of glycogen metabolism in the treated body.

The method of treatment of the present invention may be of particular use in the treatment of type II diabetes, where desirably an activator of RAC-PK is used, so that the down-regulation of GSK3 activity due to the action of RAC-PK is enhanced.

The method of treatment of the present invention may alternatively be of particular use in the treatment of cancer, such as ovarian cancer, where desirably an inhibitor of RAC-PK is used, so that the down-regulation of GSK3 activity due to the action of RAC-PK is depressed. Other cancers associated with irregularities in the activity of RAC-PK and/or GSK3 may also be treated by the method, such as pancreatic cancer and breast cancer.

Stimulation of RAC-PK with insulin increases activity 12-fold within 5 minutes and induces its phosphorylation at Thr308 and Ser473. RAC-PK transiently-transfected into cells can be activated 20-fold in response to insulin and 46-fold in response to IGF-1 and also became phosphorylated at Thr308 and Ser473. The activation of RAC-PK and its phosphorylation at both Thr308 and Ser473 can be prevented by the phosphatidylinositol (PI) 3-kinase inhibitor wortmannin. The phosphorylation of Thr308 and Ser473 act synergistically to activate RAC-PK.

MAPKAP kinase-2-phosphorylated RAC-PK at Ser473 in vitro increases activity 7-fold, an effect that can be mimicked (5-fold activation) by mutating Ser473 to Asp. Mutation of Thr308 to Asp also increases RAC-PK activity 5-fold and subsequent phosphorylation of Ser473 by MAPKAP kinase-2 stimulates activity a further 5-fold, an effect mimicked (18-fold activation) by mutating both Thr308 and Ser473 to Asp. The activity of the Asp308/Asp473 double-mutant was similar to that of the fully phosphorylated enzyme and could not be activated further by insulin. Mutation of Thr308 to alanine (Ala) did not prevent the phosphorylation of transfected RAC-PK at Ser473 after stimulation of 293 cells with insulin or IGF-1, but abolished the activation of RAC-PK. Similarly, mutation of Ser473 to Ala did not prevent the phosphorylation of transfected RAC-PK at Thr308 but greatly reduced the activation of transfected RAC-PK. This demonstrates that the activation of RAC-PK by insulin or IGF-1 results from the phosphorylation of Thr308 and Ser473 and that phosphorylation of both residues is preferred to generate a high level of RAC-PK activity in vitro or in vivo. Also, phosphorylation of Thr308 in vivo is not dependent on the phosphorylation of Ser473 or vice versa, that the phosphorylation of Thr308 and Ser473 are both dependent on PI 3-kinase activity and suggest that neither Thr308 nor Ser473 phosphorylation is catalyzed by RAC-PK itself.

Thus, it is preferred that the present invention incorporates the use of any agent which affects phosphorylation of RAC-PK at amino acids 308 and/or 473, e.g. insulin, inhibitors of PI 3-kinase, such as wortmannin or the like. The use of RAC-PK, itself altered at amino acids 308 and/or 473, e.g., by phosphorylation and/or mutation, is also suitable.

In a variation of the method of the present invention, stimulation or inhibition of RAC-PK may be assessed by monitoring the phosphorylation states of amino acids 308 and/or 473 on RAC-PK itself.

Different isoforms of RAC-PK may be used or targeted in the present invention, e.g., RAC-PKα, β or .gamma.

We have observed that modulation of RAC-PK activity appears to be effected by reversible phosphorylation, in which the equilibrium of the phosphorylation/dephosphorylation reaction is shifted in order to change the levels of active RAC-PK with respect to its inactive form. Build-up of the active form may therefore be promoted by inhibition of the dephosphorylation reaction, achieved by treatment with a phosphatase inhibitor.

A surprising aspect of the present invention is that tyrosine phosphatase inhibitors, such as vanadate, are able to activate RAC-PK notwithstanding the fact that, as is disclosed herein, this kinase is activated by phosphorylation at Ser and Thr residues.

It is known that vanadate activates p70S6K. The invention accordingly does not extend to the use of vanadate to activate p70S6K. However, the use of phosphatase inhibitors, such as okadaic acid, which acts through a quite different mechanism, is part of the present invention.

As referred to herein, the signaling pathways are the activation cascades which ultimately regulate signal transduction and kinases of these pathways are kinases whose in vivo targets include at least one entity which contributes to such signal transduction. Preferably, the signaling pathways of the invention are insulin-dependent signaling pathways, which are responsible for transduction of signals from insulin and other growth factors. Without in any way wishing to place any limitation on the present invention, one such a pathway is believed to be triggered in vivo by binding of growth factors, such as insulin and the like to their receptors, which stimulates inter alia PI-3K. PI-3K in turn directly or indirectly phosphorylates RAC-PK, which indirectly leads to the eventual phosphorylation of p70S6K.

Treatment of kinases according to the invention in order to activate them requires the exposure of the kinase to a phosphorylating agent, such as another kinase of the signaling pathway and the phosphatase inhibitor. This may be accomplished, e.g., in vitro by:

(a) incubating together a kinase of a signaling pathway, an agent capable of phosphorylating the kinase in order to activate it, and a phosphatase inhibitor; and (b) purifying the kinase from the incubation mixture.

The phosphorylating agent should be effective to phosphorylate the kinase on residues which lead to activation thereof. In the case of RAC-PK, the phosphorylating agent advantageously targets Ser and Thr residues.

Preferably, the phosphorylating agent is one or more kinases of the signaling pathway which act, in the presence of suitable activating factors, to phosphorylate and thereby activate the kinase of interest. Preferably, this is accomplished by recovering active kinase enzyme form phosphatase-inhibitor treated cells, which contain the required signaling pathway kinases.

In the context of the present invention, in vitro signifies that the experiment is conducted outside a living organism or cell. In vivo includes cell culture. Treatment of cells in vivo with phosphatase inhibitors is especially effective for the preparation of active RAC-PK. However, since RAC-PK and other signaling kinases, e.g., p70S6K, are on the same pathway, activation of RAC-PK results in the activation of other kinases on the same signaling pathway, e.g., p70S6K itself. The invention therefore includes a method for activating kinases on signaling pathways in general, except for p70S6K, especially where such kinases are downstream of RAC-PK in the pathway.

Cells which produce kinases which may be used in the present invention generally include any cell line of mammalian origin, especially fibroblast cell lines, such as RAT-1, COS or NIH 3T3. Swiss 3T3 cells are particularly preferred. Where human cell lines are used, human embryonic kidney 293 cells are preferred.

Phosphatase inhibitors are agents which inhibit protein dephosphorylation by inhibiting the activity of phosphatase enzymes. A phosphatase has essentially the inverse activity of a kinase, and removes phosphate groups.

Examples of phosphatase inhibitors are vanadate and okadaic acid, with vanadate being the more effective agent in the case of RAC-PK. However, the action of vanadate is believed to be indirect, since it is a specific tyrosine phosphatase inhibitor and RAC-PK does not appear to be stimulated by tyrosine phosphorylation. Okadaic acid, on the other hand, which is known to act directly on phosphatase PP2A, appears to directly inhibit dephosphorylation of RAC-PK.

The use of other phosphatase inhibitors is envisaged and limited only by the suitability of such inhibitors for administration to the particular cell line being used. Vanadate and okadaic acid are believed to be generally applicable, but those of skill in the art will recognize that other phosphatase inhibitors are available and that their activity and suitability may easily be determined by routine empirical testing. For example, phosphatase inhibitors which may be suitable in the present invention include calyculin A, cantharidic acid, cantharidin, DTX-1, microcystin, nodularin and tautomycin. These and other phosphatase inhibitors are available commercially, e.g., from Calbiochem.

The phosphatase inhibitor is administered to cells in their normal growth medium, which may be serum free. Serum is itself observed to stimulate kinase activity, but is expensive and its function may be substituted by a phosphatase inhibitor according to the present invention. Suitable concentrations of phosphatase inhibitors include levels from 0.01-10 mM, preferably 0.1-1 mM. The most preferred concentration for vanadate is 0.1 mM.

The method of the invention may comprise additional steps intended to isolate the desired active kinase from the cells in which it is produced. Such steps are conventional procedures familiar to those skilled in the art and may be substituted for equivalent processes within the scope of the invention. The preferred process, however, comprises the steps of homogenizing the cells, removing cell debris, e.g., by centrifugation, and separating the desired kinase by affinity purification.

Homogenization may be carried out in a standard isotonic lysis buffer, advantageously containing a proteinase inhibitor, such as phenylmethyl sulphonyl fluoride (PMSF) and a phosphatase inhibitor in order to inhibit deactivation of the kinase during the purification procedure. The cells are disrupted, thereby releasing the cytoplasmic and nuclear contents thereof into the lysis buffer.

Cell debris is then advantageously removed from the lysed cellular preparation, preferably by centrifuging the mixture in order to pellet all particulate matter. Only the soluble fraction remains in the supernatant.

The supernatant can then be subjected to standard protein purification techniques in order to isolate the kinase of interest if desired. Preferred methods, especially for relatively low volume preparations, involve affinity chromatography. Such techniques may employ an anti-kinase antibody or antiserum immobilised to a suitable matrix. Other immobilized binding agents, such as substrate analogues, may be employed.

Antibodies useful for immunoseparation of activated kinases according to the invention may be prepared according to techniques known in the art. In order to prepare a polyclonal serum, e.g., an antigenic portion of the desired kinase, consisting of a peptide derived therefrom, such as a C-terminal peptide, or even the whole kinase, optionally in the presence of an adjuvant or conjugated to an immunostimulatory agent, such as keyhole limpet haemocyanin, is injected into a mammal, such as a mouse or a rabbit, and antibodies are recovered therefrom by affinity purification using a solid-phase bound kinase or antigenic portion thereof. Monoclonal antibodies may be prepared according to established procedures.

Alternatively, and especially for larger scale preparations, separation procedures not involving affinity chromatography may be used.

For example, numerous methods are available in the art for separating polypeptides on the basis of size, such as chromatography and gel electrophoresis. Preferred are methods which perform a purification function, as well as a size separating function, while not introducing unacceptable contaminants. Thus, methods, such as step or continuous gradient centrifugation, particularly using sucrose gradients, dialysis techniques using controlled-pore membranes and membrane (Amicon) centrifugation, are preferred. Especially preferred, however, is size exclusion chromatography, typically performed using porous beads as the chromatographic support. Size exclusion chromatography is, e.g., described by Stellwagen in Deutscher, Ed., Guide to Protein Purification, Academic Press, Inc., San Diego, Calif., pp. 317-328 (1990).

Alternative purification methods, described in general in Deutscher (1990), supra, include chromatography based on separation by charge difference, such as ion exchange chromatography using an exchange group, such as DEAE or CM bound to a solid phase packing material, such as cellulose, dextran, agarose or polystyrene. Other methods include hydroxyapatite column chromatography [see, e.g., Gorbunoff, Methods Enzymol, Vol. 117, pp. 370-380 (1985)], and general affinity chromatography using glass beads or reactive dyes as affinity agents.

Advantageously, cation exchange chromatography may be employed, such that protein elution can be tailored to take into account the known or estimated PI of the kinase in question. The PI for any kinase may be determined experimentally, by isoelectric focusing. In this manner, it is possible selectively to elute from the cation exchange resin those proteins having a PI at or around that of the kinase, which results in a high degree of purification.

The invention further provides the use of an active kinase prepared according to the invention in a method for screening potential modulators of signaling pathways. Thus, the claimed method may comprise the additional step of exposing the kinase to a potential inhibitor and subsequently assessing the activity of the kinase in order to determine the effectiveness of the modulator.

The invention accordingly provides a method for screening candidate modulators of signaling pathways comprising:

(a) incubating together a kinase of a signaling pathway and a phosphatase inhibitor;

(b) adding a candidate modulator of the signaling pathway; and (c) determining the activity of the kinase.

The exposure to the modulator may be performed on the activated or inactivated kinase either in a cell-free environment, optionally after purification of the kinase from the crude cellular preparation, or in situ in the cells which produce the kinase, after phosphatase inhibitor activation. Steps (a) and (b) may therefore be reversed, or conducted contemporaneously.

In step (a), especially if the assay is to be performed in vitro, an agent capable of phosphorylating the kinase may be added to the incubation mixture. Phosphatase inhibitors activate kinases by preventing dephosphorylation, so a phosphorylating agent will be required. Advantageously, the phosphorylating agent is a kinase of an insulin-dependent signaling pathway or an analogue thereof. Moreover, factors may be required to initiate or assist signal transduction in the signaling pathway. For example, it the compound being tested is a rapamycin analogue which binds FKBP, FKBP will be required in the incubation mixture.

Preferably, however, the procedure is carried out in vivo in cells containing kinases of the signaling pathway. In such an assay, the phosphatase inhibitor replaces serum or other agents previously employed as external stimulating agents to activate kinases of the signaling pathway.

The activity of the kinase may be assessed by means of a kinase activity assay, employing a substrate for the kinase. For example, MBP may be used, in accordance with established assay procedures. Physiological substrates, such as the 40S ribosomal subunit, or S6, may also be used. Alternatively, kinase activity may be assessed by determining the degree of phosphorylation of the kinase. Advantageously, phosphorylation on residues normally implicated in kinase activation is assessed. The identification of such residues, which is part of the present invention, is set forth below.

The assay of the invention may be used to measure the direct effect of the candidate compound on the assayed kinase, or it may be used to determine the effect of the compound on a kinase acting upstream thereof in the signaling pathway. In the latter situation, the assayed kinase acts as a substrate for the upstream kinase and the activity of the upstream kinase is assessed by determining the phosphorylation state or the activity of the assayed kinase.

In order to obtain a meaningful result, the activity of the assayed kinase exposed to the candidate modulator of the signaling pathway should be compared to the activity of the kinase not exposed to the agent, an inhibition of kinase activity being indicative of potential as an immunosuppressive or anti-proliferative.

Compounds which demonstrate elevated levels of kinase inhibition may then be further assessed by determining the immunosuppressive or anti-proliferative properties thereof directly, for instance, by means of a cell proliferation inhibition assay. Such an assay preferably involves physical determination of T-cell proliferation in cells which have been subjected to kinase activation by a phosphatase inhibitor, exposed to the candidate kinase inhibitor and optionally subsequently stimulated with a mitogen, such as a growth factor, IL-2 or PMA. More simply, the assay may involve exposure of unstimulated cells to the candidate inhibitor, followed by stimulation with a phosphatase inhibitor.

According to a further aspect of the invention, we have been able to determine which sites are important for the phosphorylation of kinases, particularly those of the p70.sup.S6K/RAC-PK family. Surprisingly, the majority of activating phosphorylation appears to take place on Ser and Thr residues. It is known that phosphorylation may in certain cases be mimicked by replacement of the phosphorylated amino with an acidic amino acid, such as aspartic acid or glutamic acid.

The invention accordingly provides a recombinant RAC-PK protein wherein at least one threonine residue involved in activation of the kinase through phosphorylation in vivo is replaced with an acidic amino acid residue. Moreover, the invention provides a method for screening compounds which inhibit signaling by RAC-PK comprising exposing cells treated with the constitutively active recombinant RAC-PK to the compounds.

For example, an important activating residue is Thr308, present in the so-called T-loop between subdomains 7 and 8 of the kinase. A general guide to kinase structure is given in Woodgett (1994), supra. Substitution of Thr308 with aspartic acid results in a clear increase in basal activity of the kinase, which however retains a potential for further activation. The invention therefore provides a RAC-PK in which Thr308 has been mutated to Asp.

Preferably, Ser473 is additionally mutated to Asp. Phosphorylation of this residue is required for full-activation of RAC-PK in vivo, and the Thr308/Ser473 double-mutant (both residues converted to Asp) shows a constitutive activity 18-fold higher than native RAC-PK. The double-mutant does not retain the capability for further activation.

Constitutively active kinases according to the invention may be employed in place of the phosphatase inhibitor activated kinase in screening techniques as described herein. Advantageously, such constitutively activated kinases require no external stimulating agents.

The present invention will now be described in more detail in the accompanying examples which are provided by way of non-limiting illustration, and with reference to the accompanying drawings.

EXAMPLE 1

Specific Interaction of RAC-PK with IMPDH a. Bacterial and Yeast Strains

All yeast strains and plasmids for two-hybrid experiments are obtained from Clontech (Palo Alto, Calif.) as components of the MATCHMAKER Two Hybrid System or from Dr. Nathans, Howard Hughes Medical Institute, Baltimore, Md. Yeast strains SFY526, e.g., MATa, Ura3-52, His3-200, Ade2-101, Lys2-801, Trp1-901, Leu2-3, 112, can.sup.r, Gal4-542, Gal80-538 and Ura3::GAL1-lacZ; HF7c, e.g., MATa, Ura3-52, His3-200, Lys2-801, Ade2-101, Trp1-901, Leu2-3, 112, Gal4-542, Gal80-538, Lys2::Gal1-His3 and Ura3::(Gal417-mer)sub.3-CYC1-LacZ; and PCY2 [see Chevray and Nathans, Proc Natl Acad Sci USA, Vol. 89, No. 13, pp. 5789-5793 (1992)], e.g., MATα, His3-200, Ade2-101, Lys2-801, Trp1-63, Leu2-3, Gal4-542, Gal80-538 and Ura3::Gal1-LacZ, are used to assay for protein-protein interactions. Yeast strain HF7c is used for library screening. SFY526 and PCY2 have the upstream activating sequence and TATA sequence of the GAL1 promoter fused to the LacZ gene. In HF7c, His3 is fused to a Gal1 promoter sequence and LacZ is fused to three copies of a 17-mer Gal4 consensus sequence plus the TATA sequence of the CYC1 promoter. Both His3 and LacZ are responsive to Gal4 activation. Yeast techniques including transformation are performed according to the instructions in the MATCHMAKER Two Hybrid System and as described Ausubel et al., Current Protocols in Molecular Biology, John Wiley and Sons, New York, N.Y. (1994). The bacterial strains XL1-blue (Statagene) and JM109 are employed in the cloning of plasmids and the production of GST fusion proteins. The bacterial strains JM109(DE3), BL21 (DE3)pLysS and BL21 (DE3)pLysE (Invitrogen) are used for the production of (His).sub.6-tagged proteins. General molecular biological techniques are performed as previously described in Sambrook et al. (1989), supra; and Davis et al., Basic Methods in Molecular Biology, Elsevier Science Publishing Co., New York, N.Y. (1986).

b. Plasmid Construction

Yeast vector plasmids containing the Gal4 DNA binding domain (amino acids 1-147, pGBT9) and the Gal4 activation domain (amino acids 768-881, pGAD424), as well as the control plasmids pCL1 (full-length Gal4 gene), pVA3 (p53 gene), pTD1 (SV40 large T antigen), and pLAM5' (human lamin C gene) are from Clontech. The yeast vector pPC62, containing the Gal4 DNA binding domain, is from Dr. Nathans. The GST fusion vector pGEX-2T is from Pharmacia. The baculovirus transfer vector (pVL1392) and the (His).sub.6-tag vector (pRSET-A) are from Invitrogen. pGBT-PH127, pGBT-PH150, pGBT-PHI-III and pGBT-PHIII-VI contain in-frame fusions of amino acids 1-127, 1-150, 1-47 and 47-127 of the human RACα PH domain, respectively, with the Gal4 DNA binding domain. They are constructed by subcloning PCR fragments generated with specific oligonucleotides into the EcoRI-BamHI sites of pGBT9. pGEX-PH131, pGEX-PH-KIN, pGEX-PH-KIN-CT, pGEX-KIN-CT, pGEX-KIN and pGEX-CT contained in-frame fusions of amino acids 1-131, 1-411, 1-480, 147-480, 147-411 and 411-480 of human RACα, respectively, with GST. They are constructed by subcloning PCR fragments generated with specific oligonucleotides into the BamHI-EcoRI sites of pGEX-2T, pGBT-PH-KIN, pGBT-PH-KIN-CT, pGBT-KIN-CT, pGBT-KIN and pGBT-CT contain in-frame fusions of amino acids 1-411, 1-480, 147-480, 147-411 and 411-480 of human RACα, respectively, with the Gal4 DNA binding domain. They are constructed by subcloning the appropriate BamHI-EcoRI fragments from the corresponding pGEX constructs into the PstI-XbaI sites of pPC62 using PstI-BamHI and EcoRI-XbaI adapters. The XhoI-XbaI fragments from the resultant pPC62 plasmids are then isolated and subcloned into the XhoI-EcoRI sites of pGBT9 using a XbaI-EcoRI adapter. pGAD-IMPDH1-481, pGAD-IMPDH1-427, pGAD-IMPDH1-325, pGAD-IMPDH28-514, pGAD-IMPDH70-514, pGAD-IMPDH140 and pGAD-IMPDH428-514 contain in-frame fusions of amino acids 1-481, 1-427, 1-325, 28-514, 70-514, 1-40 and 428-514 of human IMPDH type II, respectively, with the Gal4 activation domain. They are constructed by subcloning PCR fragments generated with specific oligonucleotides into the BamHI-SalI sites of pGAD424, pGEX-IMPDH contains an in-frame fusion of the complete human IMPDH type II with GST. It is constructed by subcloning the SmaI-XhoI IMPDH fragment from pGADGH-IMPDH into the SmaI site of pGEX-2T using a XhoI-SmaI adapter. pVL1392-hRACα contained the EcoRI fragment from W138xRAC71 [see Jones et al. (1991), supra] encompassing the full-coding region of human RACα. pRSET-PHQKKK contains an in-frame fusion of amino acids 1-116 of human RACα with an amino-terminal (His).sub.6-tag and the addition of 3 lysines at the carboxy terminus. It is constructed by subcloning an NdeI-PflMI fragment from pRK-RAC [see Jones et al. (1991), supra] into the BamHI-EcoRI sites of pRSET-A using BamHI-NdeI and PflMI-EcoRI adapters. All plasmid constructions are confirmed by restriction fragment analysis and sequencing.

c. Library Screening

To determine if RAC's PH domain could interact with other proteins we fuse it to the Gal4 DNA binding domain and screen a HeLa complementary DNA (cDNA) library fused to the Gal4 transcriptional activation domain in the yeast reporter strain HF7c. The human HeLa S3 MATCHMAKER cDNA library is purchased from Clontech. pGBT-PH127 is transformed into HF7c with and without the control plasmids (pGAD424, pCL1 and pTD1). Colonies from this transformation are tested for His3 and LacZ expression to confirm that the PH domain alone does not activate transcription. The HF7c transformant containing just pGBT-PH 127 is then transformed with enough of the HeLa S3 cDNA library inserted into the 2-hybrid activation vector pGADGH to produce $1.0 \times 10^6$ yeast Leu.sp.+/Trp.sup+ transformants. Doubly-transformed cells are plated onto Leu.sup.−, Trp.sup.− and His.sup.− plates and incubated at 30.degree. C. for 3-8 days. Positive colonies are picked, re-streaked onto triple minus plates and assayed for LacZ activity by the filter assay. Library clones that are His.sup.+ and LacZ.sup.+ are then cured of the pGBT-PH127 plasmid and tested again for His auxotrophy and LacZ activity. Cured clones that are negative in both assays are then mated to transformants of PCY2 containing either pGBT9, pGBT-PH127, pLAM5' or pTD1. The activation clones corresponding to the diploids which become positive for both His auxotrophy and LacZ activity only in the presence of pGBT-PH127 are chosen for sequencing.

In our screen of $1.0 \times 10^6$ primary transformants we identify 37 clones which show specific interaction with RAC's PH domain, by activation of the reporters for His auxotrophy and LacZ activity. These clones could be subdivided into 6 different cDNA classes, based on the size of the cDNA insert. Upon sequencing all clones were found to encode human IMPDH type II inclusive of the initiator methionine through to the termination codon of the previously cloned cDNA. See Collart and Huberman (1988), supra.

The interaction requires a complete PH domain as constructs containing either subdomains I-III (amino acids 1-47) or subdomains IV-VI (amino acids 47-127) alone do not show any interaction with IMPDH. The lack of interaction with subdomains IV-VI is significant as this region has previously been shown to interact weakly with the β.gamma.-subunits of heterotrimeric G-proteins. This interaction of IMPDH and RAC's PH domain is however inhibited in the 2-hybrid system with constructs containing RAC's kinase domain juxtaposed to RAC's PH domain as occurs in its natural context. This could be due to an intramolecular interaction of RAC's PH domain with itself or another region of RAC. However, inclusion of amino acids between the PH and kinase domains (including the first four amino acids of the kinase domain) didn't inhibit the interaction. We also fuse RAC's PH domain to the Gal4 activation domain to test if it could interact with any of the human RACα Gal4 DNA binding constructs. We can detect no such interaction, indicating that the PH domain does not self associate or form a complex with other regions of the RAC-PK molecule in this system. The inhibition of interaction observed above would thus appear to be due to steric hindrance.

We construct nested amino and carboxyl-terminal deletions of IMPDH to determine the region of the molecule responsible for interaction with RAC's PH domain. This indicates that an almost intact IMPDH molecule is required for the interaction. The amino-terminal boundary of the PH interaction domain is found to lie between amino acids 28 and 70, while the carboxyl-terminal boundary lies between amino acids 427 and 481.

d. In Vitro Binding Studies

To test if IMPDH could interact directly with RAC's PH domain we employ an in vitro binding assay system using GST fusions. GST fusions produced from the plasmids pGEX-2T, pGEX-PH131 and pGEX-IMPDH are expressed in E. coli XL-1 blue cells by induction with 0.1 mM IPTG for 2 hours at 24.degree. C. The fusion proteins are purified as described [see Smith and Johnson, Gene, Vol. 67, No. 1, pp. 31-40 (1988)] except that the cells are lysed in a French Press. The human RACα PH domain (His).sup.6 tagged fusion produced by B121(DE3)pLysS cells transformed with pRSET-PHQKKK is expressed and purified as described in UK patent application No. 9525705.1. Briefly, cells are induced with 0.2 mM IPTG for 2 hours at 24.degree. C. before harvesting. Cell pellets are lysed in a French Press and the soluble PH domain is purified sequentially on Ni(II) affinity, cation exchange and gel filtration columns. Binding studies are performed using GST fusions (2.5.mu.g) coupled to glutathione-agarose beads in binding buffer (20 mM phosphate buffer, pH 7.2, 150 mM NaCl, 1% Triton X-100, 5 mM DTT) containing 2.5.mu.g of (His).sup.6-tagged PH domain or baculovirus produced human RACα in a total volume of 100.mu.L. The samples are incubated at 4.degree. C. for 1-2 hours with agitation every 5 minutes. The beads are then washed 3.times. with buffer (20 mM phosphate buffer, pH 7.2, 150 mM NaCl) before being analyzed by SDS-PAGE and stained with coomassie blue R-250 [for (His).sub.6-tagged PH domain binding] or SDS-PAGE followed by Western blot analysis using a human RACα specific antiserum (for human RACα binding). See Jones et al., Jakubowicz and Hemmings (1991), supra. The secondary antibody is a horseradish peroxidase coupled anti-rabbit antibody (Amersham) which is detected using the ECL method (Amersham) by autoradiography. In this assay we see that the (His).sub.6-tagged PH domain can bind to the GST-IMPDH fusion but not to GST alone.

We also employ this assay system to test if full-length baculovirus purified human RACα could directly interact with IMPDH. Full-length human RACα is expressed and purified from the baculovirus system as described in UK patent application No. 9525702.8. Briefly, a baculovirus is constructed by co-transfection of Sf9 cells with pVL1392-hRACα and wild-type (WT) baculovirus AcMNPV DNA and purified by limiting dilution and detected by dot-blot hybridization. The purified virus is used to produced human RACα in Sf9 cells. The human RACα is purified by sequential anion exchange, phospho-cellulose and gel filtration chromatography. Here we see specific interaction of the full-length RAC-PK molecule with GST-IMPDH and not GST alone or the GST-PH fusion.

e. In Vivo Pull-Down Assay

Using GST-IMPDH in a pull-down assay with MCF-7 cell extracts we see a specific association of human RACα with the GST-IMPDH and not with GST. MCF-7 cells are lysed in buffer (50 mM Tris-HCl, pH 8.0, 120 mM NaCl, 1% NP-40, 1 mM EDTA, 1 mM EGTA, 30 mM pNPP, 25 mM β-glycerol phosphate, 15 mM PPi, 25 mM NaF, 1 mM vanadate, 20.mu.M PAO, 1 mM benzamidine, 0.1 mM PMSF) using 12 strokes of a dounce homogenizer. Soluble protein from the supernatant of lysates centrifuged at 14,000.times.g for 15 minutes at 4.degree. C. are added to GST, GST-PH or GST-IMPDH protein (5.mu.g) attached to glutathione beads and incubated at 4.degree. C. for 2 hours with continuous agitation. The beads are then washed 4.times. with lysis buffer before being analyzed by Western blotting as described above with the human RACα-specific antiserum. See Jones, Jakubowicz and Hemmings (1991), supra] or an IMPDH-specific antiserum. See Collart and Huberman (1988), supra. We could also perform the converse experiment, pulling down IMPDH from cell lysates using the GST-PH domain fusion protein. Thus we have shown the existence of an association between human RACα and human IMPDH type II in 3 heterologous systems.

f. Enzyme Assays

We then assay the effect of this interaction on the activity of IMPDH. The addition of soluble PH domain as a GST fusion produced an activation of IMPDH compared to the addition of GST alone. Assays for IMPDH activity are performed essentially [see Antonio and Wu, Biochem, Vol. 33, pp. 1753-1759 (1994)], monitoring the production of XMP by absorbance at 286 nm. The IMPDH is produced as a GST fusion purified on glutathione beads and then eluted as soluble protein with reduced glutathione. IMPDH activity is tested in the presence of either soluble GST (produced from pGEX-2T) or PH domain (produced from pGEX-PH131) at a molar ratio of IMPDH to GST/PH domain of 1:5. RAC kinase assays with the baculovirus produced human RACα using various substrates, e.g., myelin basic protein, GST or GST-IMPDH, are performed essentially as described. See Jones, Jakubowicz and Hemmings (1991), supra. When IMPDH is tested in RAC-PK assays using the baculovirus produced human RACα to see if it is a substrate we could detect no significant phosphorylation of the IMPDH.

EXAMPLE 2

Inhibition of GSK3

Two major kinases known to be involved in regulating the insulin-dependent signaling pathways are MAPKAP kinase-1 and p70.sup.S6K. These kinases are respectively inhibited by PD98059 and rapamycin. Both of these agents fail to inhibit phosphorylation of GSK3, suggesting that the kinase responsible for GSK3 inactivation is not MAPKAP kinase-1 or p70.sup.S6K.

L6 myotubes are incubated with both compounds and the stimulated with insulin, as follows. Monolayers of L6 cells are grown in 6 cm petri dishes to the stage of myotubes, deprived of serum overnight and then incubated for 1 hour in 20 mM Hepes/NaOH, pH 7.4, 0.14 M NaCl, 5 mM KCl, 2.5 mM MgSO.sub.4, 1 mM CaCl.sub.2, 25 mM glucose (HBS buffer), in the presence or absence of 50.mu.M PD98059 or 100.mu.M LY294002. Two (2) mM 8-Br-cAMP or 0.1.mu.M rapamycin, when added, are included for the last 15 minutes. The cells are stimulated for 5 minutes with 0.1.mu.M insulin, or for time courses of up to 10 minutes. The medium is removed by aspiration, the cells placed on ice and lysed in 0.2 mL of ice-cold buffer A, 50 mM Tris-HCl, pH 7.5, 20.degree. C., 1 mM EDTA, 1 mM EGTA, 1% (.sup w/.sub.v) Triton X-100, 1 mM sodium orthovanadate, 10 mM sodium glycerophosphate, 50 mM sodium fluoride, 5 mM sodium pyrophosphate, 2.mu.M microcystin, 0.1% (.sup.v/.sub.v) 2-mercaptoethanol, leupeptin 4.mu.g/mL, 1 mM benzamidine, 1 mM phenylmethane sulphonyl fluoride, 30.mu.g/mL aprotinin, 30.mu.g/mL antipain, 10.mu.g/mL pepstatin.

Precipitation of p42.sup.MAPK, MAPKAP kinase-1 or GSK3 from the cell lysates by immunoprecipitation and analysis of their activity with specific protein or peptide substrates [see Cross et al. (1994), supra] shows that insulin inactivation of GSK3 is not affected by agents (2 mM 8-BrcAMP or 0.1.mu.M rapamycin) which inhibit classical MAP kinase or p70.sup.S6K signaling pathways.

In order to identify the kinase which inhibits GSK3 in the presence of rapamycin and PD98059, cells are lysed as above and the cell lysates (0.3 mg) chromatographed on a 5.times.0.16 cm column of Mono Q [see Sutherland and Cohen, FEBS Lett, Vol. 338, No. 1, pp. 37-42 (1994)] except that the buffer additionally contains 1 mM EGTA, 0.1 mM sodium orthovanadate and 0.5% (.sup.w/.sub.v) Triton X-100.

The fractions (0.05 mL) assayed with the synthetic peptide GRPRTSSFAEG SEQ ID NO: 5, which corresponds to the sequence of GSK3 surrounding the serine (bold type) whose phosphorylation triggers the inactivation of GSK 3α (Ser21) and GSK3β (Ser9). Three peaks of activity which result in phosphorylation of this peptide are eluted. These peaks are absent if insulin stimulation is not given, or if cells are incubated with 0.1.mu.M wortmannin prior to insulin stimulation. The inactivating effect of insulin on GSK3 is known to be prevented by administering this concentration of wortmannin, or 100.mu.M LY294002, a structurally-unrelated inhibitor of PI-3K.

All 3 peaks of phosphorylating activity can be immunoprecipitated with an anti-RAC antibody using a polyclonal rabbit antiserum directed against the peptide FPQF-SYSASSTA SEQ ID NO: 7 raised by injecting rabbits subcutaneously with the peptide and purified by precipitation using 50% (NH.sub.4).sub.2SO.sub.4 followed by affinity chromatography on RAC-peptide coupled Affigel® 10 column (Bio-Rad).

In contrast, immunoprecipitating with an anti-MAPKAP kinase-1 antibody fails to deplete any peptide phosphorylating activity from the Mono Q column.

In order to determine that complete GSK3 can be inactivated by RAC, GSK3α and GSK3β are partially purified from rabbit skeletal muscle [see Sutherland and Cohen (1994), supra] and assayed with a specific peptide substrate. See Cross et al. (1994), supra. Each GSK3 isoform is diluted to 15 U/mL and GSK3 activity measured after incubation for 20 minutes with MgATP in the presence or absence of RAC. The incubation is the made 20 mM in EDTA to stop the kinase reaction, incubated for 20 minutes with 5 mU/mL PP2A, to reactivate GSK3, made 2.mu.M in okadaic acid to inactivate PP2A, and then assayed for GSK3 activity.

In the absence of RAC, GSK3 is stably active throughout the experiment. Otherwise, however, RAC-PK successfully inhibited GSK3 activity and, this inactivation was sensitive to PP2A.sub.1, which restored GSK3 activity. The absence of insulin stimulation, the presence of wortmannin or the disruption of RAC-PK immunoprecipitation by incubation of the anti-RAC antibody with the peptide immunogen all result in a lack of GSK3 inactivation in this experiment.

EXAMPLE 3

To determine if RAC-PK's domain with its carboxyl-terminal extension could interact with other proteins we fused it to the Gal4 DNA binding domain and screened a HeLa cDNA library fused to the Gal4 transcriptional activation domain in the yeast reporter strain HF7c following the procedure of Example 1. Briefly, amino acids 147-480 of RACα are fused in frame to GST in the expression vector pGEX-2T (see Example 1). Appropriate BamHI-EcoRI fragment is then subcloned into the PstI-XbaI sites of yeast vector pPC62 (Dr. Nathans) using PstI-BamHI and EcoRI-XbaI linkers in order to create a Gal4 DNA binding domain-RAC-PK and C-terminal domain fusion. XhoI-XbaI fragments are then subcloned into pGBT9 (Clontech). The HeLa S3 MATCH-MAKER cDNA library is used as before.

In our screen of 1.5.times.10.sup.6 primary transformants, we identify 7 clones which show specific interaction with RAC-PK's domain plus the carboxyl-terminal extension, by activation of the reporters for His auxotrophy and LacZ activity. A detailed analysis of the specific region of RAC-PK that the clone interacts with shows that the carboxyl-terminal 69 amino acids are all that is required to confer the interaction. We thus denote this molecule carboxyl-terminal binding protein (CTBP). None of the clones shows an interaction with the kinase domain alone. This interaction is seen in all constructs containing the carboxyl-terminal extension including a full-length RAC-PK construct, indicating that the interaction is not inhibited by another region of the RAC-PK molecule. Interestingly, the C-terminal domain of RAC-PK is phosphorylated in response to insulin activation, suggesting a role for CTBP as a modulator of insulin action.

All 7 specific interacting clones contain identical cDNA inserts of 1.3 kb in length with an ALU repeat of .about.300 nt at the 3' end (SEQ ID NO: 1). Searches of the Gene-EMBL nucleotide database using the cDNA sequence without the ALU repeat with the FASTA programme (GCG Package) identify no significant homologies. The deduced amino acid sequence of the CTBP cDNA produces a short 47-residue polypeptide rich in alanines (21%) and arginines (21%). Searches of the PIR, Swiss-Prot and GP protein databases using FASTA (GCG Package) and the Gene-EMBL nucleotide database using TFASTA (GCG Package) reveal no significant homologies to the CTBP protein sequence.

The sequence of CTBP identified is believed to represent the 3' end of the complete CTBP molecule.

To test if the novel protein CTBP could interact directly with RAC-PK we employ an in vitro binding assay system using GST fusions, as described in Example 1. In this assay we see specific interaction of the full-length RAC, produced in the baculovirus system with GST-CTBP and not GST alone.

To test if this interaction occurs in vivo we employ a pull-down assay using the GST-CTBP fusion protein and MCF-7 cell extracts, as described in Example 1. Here we see the specific association of the MCF-7 RACα with the GST-CTBP but not GST alone.

EXAMPLE 4

RAC-PK Influences GSK3 Activity

FIG. 1 (a)—L6 myotubes were incubated for 15 minutes with 2 mm 8-bromocyclic-AMP (8Br-cAMP) and then with 0.1.mu.M insulin (5 minutes). Both GSK3 isoforms were co-immunoprecipitated from the lysates and assayed before (black bars) and after (white bars) reactivation with PP2A. See Cross et al. (1994), supra. The results are presented relative to the activity in unstimulated cells, which was 0.08.+-.0.006 U mg.sup.-1 (n=10).

(b and c)—The inhibition of GSK3 by insulin (0.1.mu.M) is unaffected by rapamycin (0.1.mu.M) and PD 98059 (50.mu.M), but prevented by LY 294002 (100.mu.M).

(b)—L6 myotubes were stimulated with insulin for the times indicated with (filled triangle) or without (filled circles) a 15 minutes pre-incubation with LY 294002, and GSK3 measured as in (a). The open circles show experiments from insulin-stimulated cells where GSK3 was assayed after reactivation with PP2A. See Cross et al. (1994), supra.

(c)—Cells were incubated with rapamycin (triangles) or rapamycin plus PD 98059 (circles) before stimulation with insulin, and GSK3 activity measured as in (a), before (filled symbols) and after (open symbols) pretreatment with PP2A.

(d and e)—L6 myotubes were incubated with 8Br-cAMP (15 minutes), PD 98059 (60 minutes) or LY 294002 (15 minutes) and then with insulin (5 minutes) as in (a-c). Each enzyme was assayed after immunoprecipitation from lysates, and the results are presented relative to the activities obtained. In the presence of insulin and absence of 8Br-cAMP, which were $0.04.+-.0.005$ U mg.sup.-1 (p42 MAP kinase, n=6) and $0.071.+-.0.004$ U mg.sup.-1 (MAPKAP Kinase.sup.-1, n=6).

All the results (.+-.s.e.m.) are for at least 3 experiments.

Monolayers of L6 cells were cultured, stimulated and lysed as described previously. See Cross et al. (1994), supra. p42 MAP kinase, MAPKAP kinase 1 or GSK3-α plus GSK3-β were then immunoprecipitated from the lysates and assayed with specific protein or peptide substrates as described previously. See Cross et al. (1994), supra. One unit of PK activity was that amount which catalyzed the phosphorylation of 1 nmol of substrate in 1 minute. Where indicated, GSK3 in immunoprecipitates was reactivated with PP2A. See Cross et al. (1994), supra.

Figure 2:
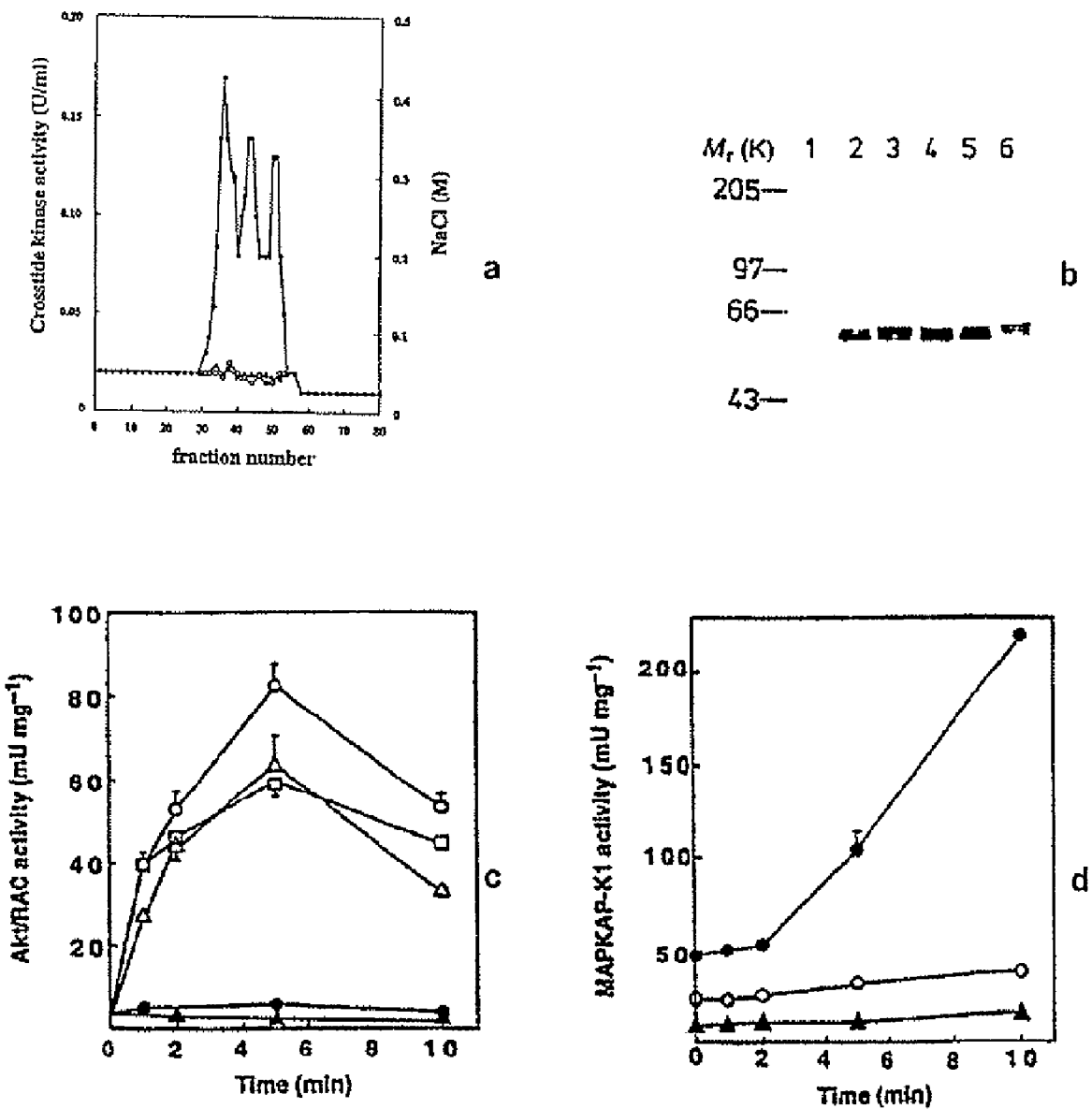
FIG. 2(a) depicts RAC-PK kinase activity. L6 myotubes were incubated with 50 μM PD 98059 (for 1 hour) and 0.1 μM rapamycin (for 10 minutes), then stimulated with 0.1 μM insulin (5 minutes) and lysed. The lysates (0.3 mg protein) were chromatographed on Mono Q (5.times.0.16 cm) and fractions (0.05 mL) were assayed for Crosstide kinase (filled circles). In separate experiments insulin was omitted (open circles) or wortmannin (0.1.mu.M) added 10 minutes before the insulin (filled triangles). The broken line shows the NaCl gradient.
FIG. 2(b) depicts RAC-PK kinase activity from 6 additional experiments with results similar to those shown in 2(a). Pooled fractions (10 μL apiece), 31-34 (lane 1), 35-38 (lane 2), 39-42 (lane 3), 43-45 (lane 4), 46-49 (lane 5) and 50-53 (lane 6), from a were electrophoresed on a 10% SDS/polyacrylamide gel and immunoblotted with the C-terminal anti-RAC-PKα antibody. Marker proteins are indicated. No immunoreactive species were present in fractions 1-30 or 54-80.
FIG. 2(c) depicts the results of L6 myotubes stimulated with 0.1 μM insulin and RAC-PK immunoprecipitated from the lysates (50.mu.g protein) essentially as described previously, using the anti-PH domain antibody and assayed for Crosstide kinase (open circles). In control experiments, myotubes were incubated with 0.1 μM rapamycin plus 50 μM PD 98059 (open triangles) or 2 mM 8Br-cAMP (open squares), or 0.1 μM wortmannin (filled circles) or 100 μM LY 294002 (filled triangles) before stimulation with insulin. The error bars denote triplicate determinations.
FIG. 2(d) depicts the results of L6 myotubes stimulated with 0.1 μM insulin and MAPKAP kinase-1 was immunoprecipitated from the lysates and assayed with S6 peptide (filled circles). In control experiments, cells were incubated with 0.1 μM rapamycin plus 50 μM PD 98059 (filled triangles) or with 2 μM 8BR-cAMP (open circles) before stimulation with insulin. The error bars denote triplicate determinations.

FIG. 2—Identification of RAC-PK as the insulin-stimulated, wortmannin-sensitive and PD 98059/rapamycin-insensitive Crosstide kinase in L6 myotubes.

(a)—Cells were incubated with 50.mu.M PD 98059 (for 1 hour) and 0.1.mu.M rapamycin (10 minutes), then stimulated with 0.1.mu.M insulin (5 minutes) and lysed. See Cross et al. (1994), supra. The lysates (0.3 mg protein) were chromatographed on Mono Q (5.times.0.16 cm) and fractions (0.05 mL) were assayed for Crosstide kinase (filled circles). In separate experiments insulin was omitted (open circles) or wortmannin (0.1.mu.M) added 10 minutes before the insulin (filled triangles). The broken line shows the NaCl gradient.

Similar results were obtained in 6 experiments.

(b)—Pooled fractions (10.mu.L), 31-34 (lane 1), 35-38 (lane 2), 39-42 (lane 3), 43-45 (lane 4), 46-49 (lane 5) and 50-53 (lane 6), from a were electrophoresed on a 10% SDS/polyacrylamide gel and immunoblotted with the C-terminal anti-RAC-PKα antibody. Marker proteins are indicated. No immunoreactive species were present in fractions 1-30 or 54-80.

(c)—L6 myotubes were stimulated with 0.1.mu.M insulin and RAC-PK immunoprecipitated from the lysates (50.mu.g protein) essentially as described previously [see Lazar et al., J Biol Chem, Vol. 270, No. 35, pp. 20801-20807 (1995)], using the anti-PH domain antibody and assayed for Crosstide kinase (open circles). In control experiments, myotubes were incubated with 0.1.mu.M rapamycin plus 50.mu.M PD 98059 (open triangles) or 2 mM 8Br-cAMP (open squares), or 0.1.mu.M wortmannin (filled circles) or 100.mu.M LY 294002 (filled triangles) before stimulation with insulin.

(d)—As (c) except that MAPKAP kinase-1 was immunoprecipitated from the lysates and assayed with S6 peptide (filled circles). In control experiments, cells were incubated with 0.1.mu.M rapamycin plus 50.mu.M PD 98059 (filled triangles) or with 2.mu.M 8BR-cAMP (open circles) before stimulation with insulin. In (c) and (d), the error bars denote triplicate determinations, and similar results were obtained in 3 separate experiments.

Mono Q chromatography was performed as described [see Burgering and Coffer (1995), supra], except that the buffer also contained 1 mM EGTA, 0.1 mM sodium orthovanadate and 0.5% (.sup.w/.sub.v) Triton X-100. Two RAC-PKα antibodies were raised in rabbits against the C-terminal peptide FPQFSYSASSTA (SEQ ID NO: 7) and bacterially-expressed PH domain of RAC-PKα. The C-terminal antibody was affinity purified. See Jones et al. (1991), supra. The activity of RAC-PK towards Crosstide is threefold higher than its activity towards histone H2B and 11-fold higher than its activity towards myelin basic protein, the substrates used previously to assay RAC-PK. Other experimental details and units of protein kinase activity are given in FIG. 1.

Figure 3:
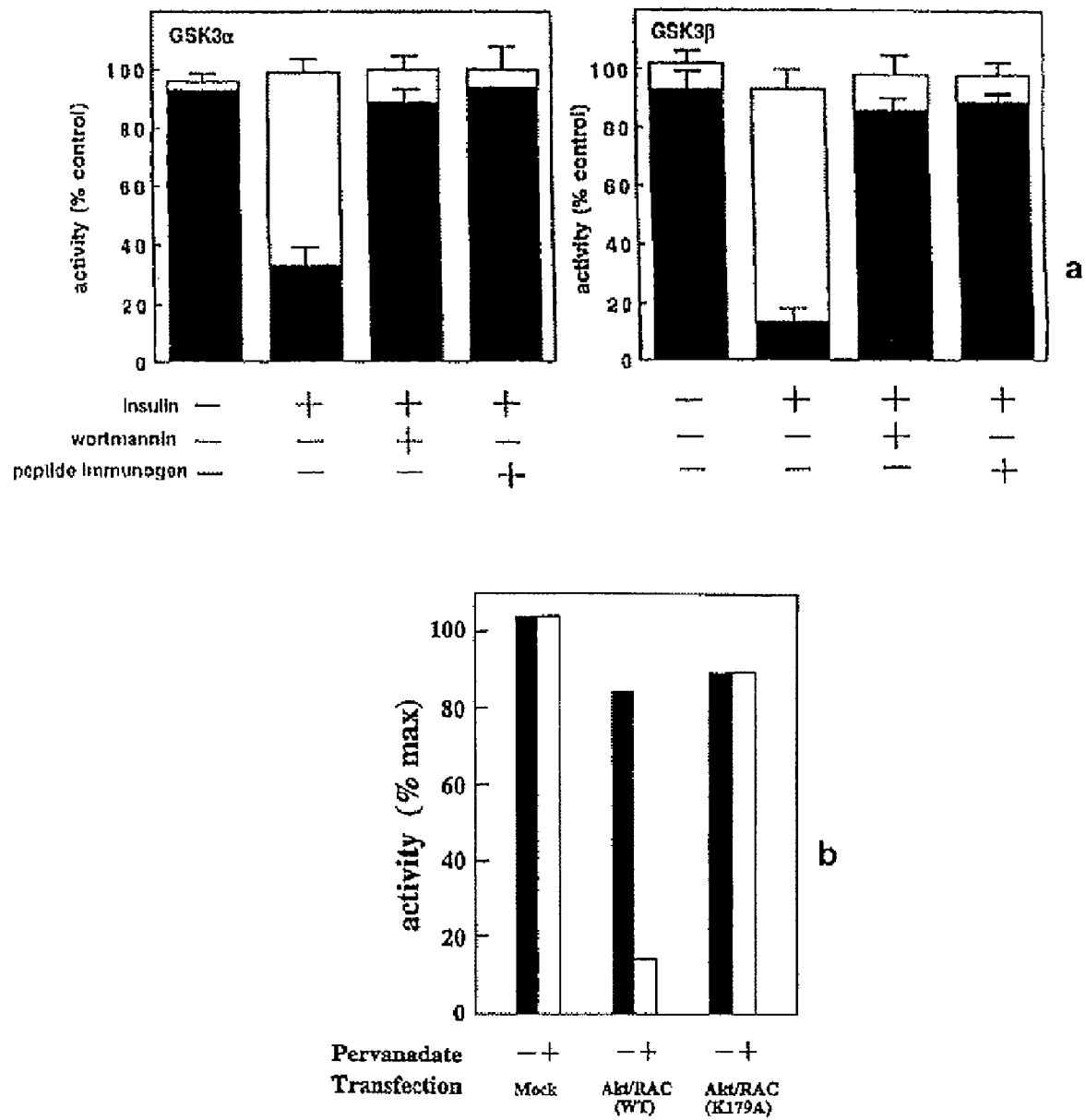
FIG. 3(a) depicts GSK3 inactivation by RAC-PK from insulin-stimulated L6 myotubes. The black bars show GSK3 activity measured after incubation with MgATP and RAC-PK as a percentage of the activity obtained in control incubations where RAC-PK was omitted. In the absence of RAC-PK, GSK3 activity was stable throughout the experiment. The white bars show the activity obtained after reactivation of GSK3 with PP2A. No inactivation of GSK3 occurred if insulin was omitted, or if wortmannin (0.1 μM) was added 10 minutes before the insulin, or if the anti-RAC-PK antibody was incubated with peptide immunogen (0.5 mM) before immunoprecipitation. The results (±s.e.m.) are for 3 experiments (each carried out in triplicate).
FIG. 3(b) depicts inactivation of GSK3-β by HA-RAC-PKα. cDNA encoding HA-RAC-PKα was transfected into COS-1 cells, and after stimulation for 15 minutes with 0.1 mM sodium pervanadate the tagged protein kinase was immunoprecipitated from 0.3 mg of lysate and incubated for 20 minutes with GSK3-β and MgATP. In control experiments, pervanadate was omitted, or WT RAC-PKα replaced by vector (mock translation) or by a kinase-inactive mutant of RAC-PKα in which Lys179 was mutated to Ala (K179A).

FIG. 3—GSK3 is inactivated by RAC-PK from insulin-stimulated L6 myotubes.

(a)—Cells were stimulated for 5 minutes with 0.1.mu.M insulin, and RAC-PK immunoprecipitated from 100.mu.g of cell lysate and used to inactivate GSK3 isoforms essentially as described previously. See Sutherland, Leighton and Cohen, Biochem J, Vol. 296, Pt. 1, pp. 15-19 (1993); and Sutherland and Cohen (1994), supra. The black bars show GSK3 activity measured after incubation with MgATP and RAC-PK as a percentage of the activity obtained in control incubations where RAC-PK was omitted. In the absence of RAC-PK, GSK3 activity was stable throughout the experiment. The white bars show the activity obtained after reactivation of GSK3 with PP2A. See Embi, Rylatt and Cohen, Eur J Biochem, Vol. 107, No. 2, pp. 519-527 (1980). No inactivation of GSK3 occurred if insulin was omitted, or if wortmannin (0.1.mu.M) was added 10 minutes before the insulin, or if the anti-RAC-PK antibody was incubated with peptide immunogen (0.5 mM) before immunoprecipitation. The results (.+-.s.e.m.) are for 3 experiments (each carried out in triplicate).

(b)—Inactivation of GSK3-β by HA-RAC-PKα. cDNA encoding HA-RAC-PKα was transfected into COS-1 cells, and after stimulation for 15 minutes with 0.1 mM sodium pervanadate the tagged protein kinase was immunoprecipitated from 0.3 mg of lysate and incubated for 20 minutes with GSK3-β and MgATP. In control experiments, pervanadate was omitted, or WT RAC-PKα replaced by vector (mock translation) or by a kinase-inactive mutant of RAC-PKα in which Lys179 was mutated to Ala (K179A). Similar results were obtained in 3 separate experiments. The levels of WT and K179A-RAC-PKα in each immunoprecipitate were similar in each transfection.

In a GSK3-α and GSK3-β were partially-purified, assayed, inactivated by RAC-PK and reactivated by PP2A from rabbit skeletal muscle as described previously. See Sutherland, Leighton and Cohen, Biochem J (1993), supra; and Sutherland and Cohen (1994), supra. There was no reactivation in control experiments in which okadaic acid (2.mu.M) was added before PP2A.

Figure 4:
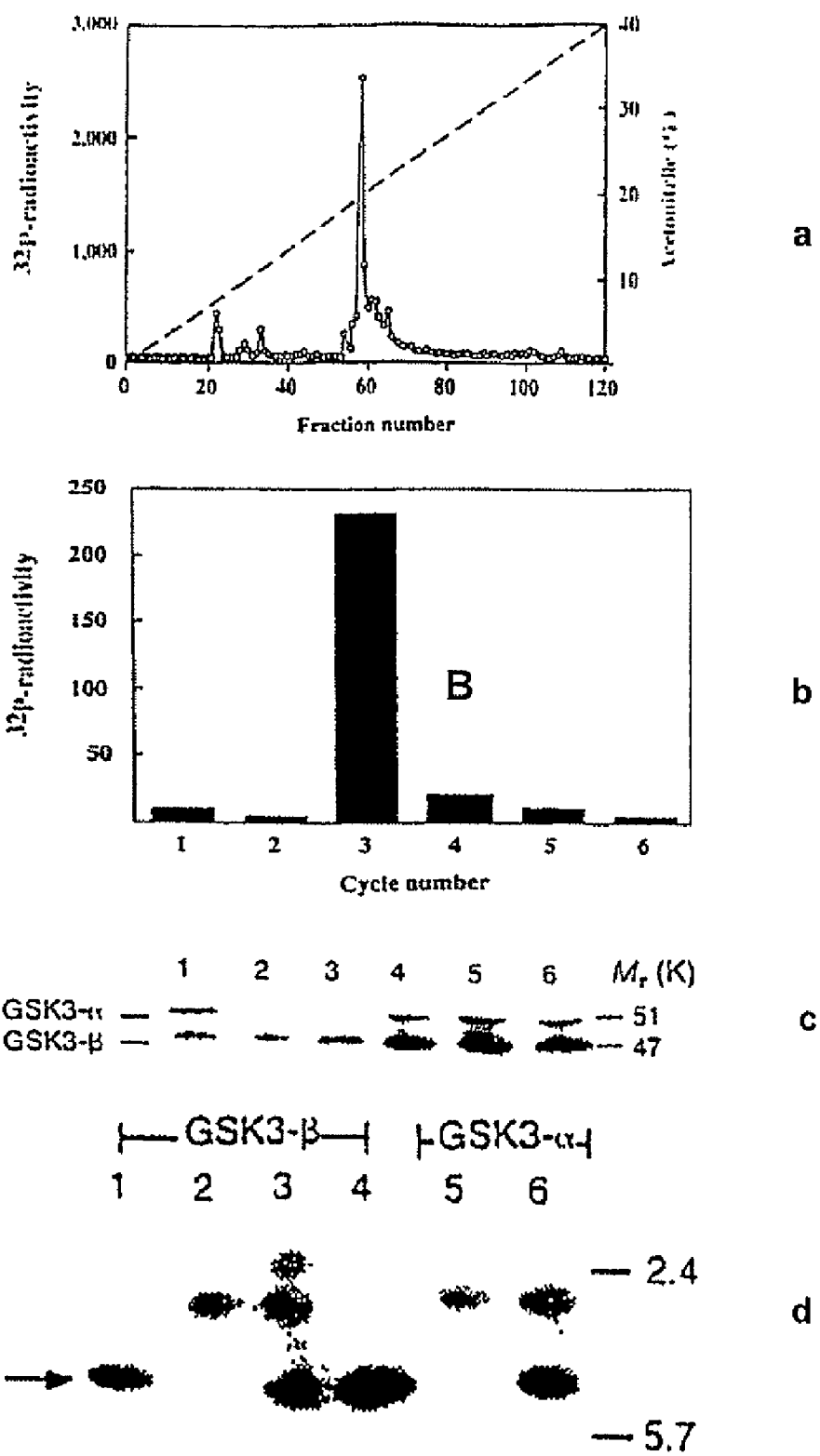
FIGS. 4(a)-4(d) depict identification of the residues in GSK3 phosphorylated by RAC-PK in vitro and in response to insulin in L6 myotubes.

FIG. 4—Identification of the residues in GSK3 phosphorylated by RAC-PK in vitro and in response to insulin in L6 myotubes.

(a)—GSK3-β was maximally inactivated by incubation with RAC-PK and Mg-[.gamma.-.sup.32P]ATP and after SDS-PAGE, the .sup.32P-labelled GSK3-β (M.sub.r 47K) was digested with trypsin.sup.11 and chromatographed on a C18-column. See Sutherland, Leighton and Cohen, Biochem J (1993), supra. Fractions (0.8 mL) were analyzed for, .sup.32P-radioactivity (open circles), and the diagonal line shows the acetonitrile gradient.

(b)—The major phosphopeptide from a (400 c.p.m.) was subjected to solid-phase sequencing [see Sutherland, Leighton and Cohen, Biochem J (1993), supra], and .sup.32P-radioactivity released after each cycle of Edman degradation is shown.

(c)—GSK3-α and GSK3-β were co-immunoprecipitated from the lysates of .sup.32P-labelled cells, denatured in SDS, subjected to SDS-PAGE, transferred to nitrocellulose and autoradiographed. See Saito, Vandenheede and Cohen, Biochem J (1994). Lanes 1-3, GSK3 isoforms immunoprecipitated from unstimulated cells; lanes 4-6, GSK3 isoforms immunoprecipitated from insulin-stimulated cells.

(d)—GSK3 isoforms from (c) were digested with trypsin, and the resulting phosphopeptides separated by isoelectric focusing [see Saito, Vandenheede and Cohen (1994), supra] and identified by auto-radiography. Lanes 1 and 4 show the major phosphopeptide resulting from in vitro phosphorylation of GSK3-β by RAC-PK and MAPKAP kinase-1, respectively; lanes 2 and 5, the phosphopeptides obtained from GSK3-β and GSK3-α, immunoprecipitated from unstimulated cells; lanes 3 and 6, the phosphopeptides obtained from GSK3-β and GSK3-α immunoprecipitated from cells stimulated for 5 minutes with 0.1.mu.M insulin; the arrow denotes the peptides whose phosphorylation is increased by insulin. The PI values of two markers, Patent Blue (2.4) and azurin (5.7) are indicated.

In (a), RAC-PKα was immunoprecipitated with the C-terminal antibody from the lysates (0.5 mg protein) of insulin-stimulated L6 myotubes and used to phosphorylate GSK-β. In (c), three 10 cm diameter dishes of L6 myotubes were incubated for 4 hours in HEPES-buffered saline [see Cross et al. (1994), supra] containing 50.mu.M PD 98059, 100 nM rapamycin and 1.5 mCl ml-1.sup.32P-orthophosphate-, stimulated for 5 minutes with insulin (0.1.mu.M) or buffer and GSK3 isoforms co-immunoprecipitated from the lysates as in FIG. 1.

Discussion

Inhibition of GSK3 induced by insulin in L6 myotubes in FIG. 1 (a-c) was unaffected by agents which prevented the activation of MAPKAP kinase-1 (8-bromo-cyclic AMP, or PD 98059) [see Alessi et al., J Biol Chem, Vol. 270, No. 46, pp. 27489-27494 (1995)], FIG. 1 (d and e) and/or p70.sup.S6k rapamycin [see Kuo et al., Nature, Vol. 358, No. 6381, pp. 70-73 (1992); and Cross et al. (1994), supra], suggesting that neither MAPKAP kinase-1 nor p70.sup.S6k are essential for this process. However, the phosphorylation and inhibition of GSK3-β after phorbol ester treatment [see Stambolic and Woodget, Biochem J, Vol. 303, Pt. 3, pp. 701-704 (1994)] is enhanced by co-expression with MAPKAP kinase-1 in HeLa S3 cells, whereas in NIH 3T3 cells the EGF-induced inhibition of GSK3-α and GSK3-β [see Saito, Vandenheede and Cohen (1994), supra] is largely suppressed by expression of a dominant-negative mutant of MAP kineas kinase-1. See Eldar-Finkelman, Seger, Vandenheede and Krebs, J Biol Chem, Vol. 270, No. 3, pp. 987-990 (1995). MAPKAP kinase-1 may therefore mediate the inhibition of GSK3 by agonists which are much more potent activators of the classical MAP kinase pathway than is insulin.

To identify the insulin-stimulated protein kinase (ISPK) that inhibits GSK3 in the presence of rapamycin and PD 98059, L6 myotubes were incubated with both compounds and stimulated with insulin. The lysates were then chromatographed on Mono Q and the fractions assayed with "Crosstide" GRPRTSSFAEG (SEQ ID NO:5), a peptide corresponding to the sequence in GSK3 surrounding the Ser (underlined) phosphorylated by MAPKAP kinase-1 and p70.sup.S6k (Ser21 in GSK3-α) [see Sutherland and Cohen (1994), supra] and Ser9 in GSK3-β, See Sutherland, Leighton and Cohen, Biochem J, Vol. 296, Pt. 1, pp. 15-19 (1993). Three peaks of Crosstide kinase activity were detected, which were absent if insulin stimulation was omitted or if the cells were first preincubated with the PI 3-kinase inhibitor wortmannin. See FIG. 2 (a). Wortmannin [see Cross et al. (1994), supra; and Welsh et al. (1994), supra], and the structurally-unrelated PI 3-kinase inhibitor LY 294002; FIG. 1 (b), both prevent the inhibition of GSK3 by insulin.

The PKs RAC-PK-α, RAC-PK-β and RAC-PK.gamma. are Ser-/Thr-specific and cellular homologues of the viral oncogene v-akt. See Coffer and Woodgett, Eur J Biochem, Vol. 201, No. 2, pp. 475-481 (1991); Jones et al. (1991), supra, Ahmed et al., Mol Cell Biol, Vol. 15, pp. 2304-2310 (1995); and Cheng et al., Proc Natl Acad Sci USA, Vol. 89, No. 19, pp. 9267-9271 (1992). These enzymes have recently been shown to be activated in NIH 3T3, Rat-1 or Swiss 3T3 cells in response to growth factors or insulin, activation being suppressed by blocking the activation of PI 3-kinase in different ways. See Franke et al., (1995), supra; and Burgering and Coffer (1995), supra. All three peaks of Crosstide kinase [see FIG. 2 (a)], but no other fraction from Mono Q, showed the characteristic multiple bands of RAC-PK (relative molecular mass, Mr 58K, 59K or 60K) that have been observed in other cells, when immunoblotting was performed with an antibody raised against the carboxyl-terminal peptide of RAC-PK-α. See FIG. 2 (b). The more slowly migrating forms represent more highly-phosphorylated protein, and are converted to the fastest migrating species by treatment with phosphatases. Phosphatase treatment also results in the inactivation of RAC-PK [see Burgering and Coffer (1995), supra] and the complete loss of Crosstide kinase activity (data not shown). Of the Crosstide kinase activity in peaks 2 and 3 from Mono Q, 70-80% was immunoprecipitated by a separate antibody raised against the amino-terminal PH domain of RAC-PK-α. The C-terminal antibody also immunoprecipitated RAC-PK activity specifically from peaks 2 and 3, but was less effective than the anti-PH-domain antibody. Peak-1 was hardly immunoprecipitated by either antibody and may represent RAC-PKβ. An immunoprecipitating anti-MAPKAP kinase-1 antibody [see Cross et al. (1994), supra] failed to deplete any of the Crosstide kinase activity associated with peaks 1, 2 or 3.

Insulin stimulation of L6 myotubes increased RAC-PK activity by more than 10-fold [see FIG. 2 (c)], and activation was blocked by wortmannin or LY 294002, but was essentially unaffected by 8-bromo-cyclic AMP or rapamycin plus PD 98059. See FIG. 2 (c). The half-time (t0.5) or activation of RAC-PK (1 minute) was slightly faster than that for inhibition of GSK3 (2 minutes). See Cross et al. (1994), supra. In contrast, the activation of MAPKAP kinase-1 [see FIG. 2 (d)] and p70.sup.s6k (not shown) was slower (t0.5>5 minutes). Activation of MAPKAP kinase-1 was prevented by 8-bromo-cyclic AMP or PD 98059 [see FIG. 2 (d)], and activation of p70.sup.S6k by rapamycin. See Cross et al. (1994), supra. Akt/RAC phosphorylated the Ser in the Crosstide equivalent to Ser21 in GSK3-α and Ser9 in GSK3-β (data not shown).

RAC-PK from insulin-stimulated L6 myotubes (but not from unstimulated or wortmannin-treated cells) inactivated GSK3-α and GSK3-β in vitro, and inhibition was reversed by the Ser-Thr-specific protein phosphatase PP2A. See Embi, Rylatt and Cohen (1980) and FIG. 3 (a). To further establish that inactivation was catalyzed by RAC-PK, and not by a co-immunoprecipitating PK, hemagglutonin-tagged RAC-PK-a (HA-RAC-PK) was transfected into COS-1 cells and activated by stimulation with pervanadate, which is the strongest inducer of RAC-PK activation in this system. The HA-RAC-PK inactivated GSK3-β, but not if treatment with pervanadate was omitted or if WT HA-RAC-PK was replaced with a "kinase inactive" mutant. See FIG. 3 (b).

The inactivation of GSK3-β by RAC-PK in vitro was accompanied by the phosphorylation of one major tryptic peptide [see FIG. 4 (a)] which co-eluted during C18-chromatography [See Sutherland, Leighton and Cohen, Biochem J, (1993), supra] and isoelectric focusing with that obtained after phosphorylation by MAPKAP kinase-1. See FIG. 4 (d).

Stimulation of L6 myotubes with insulin (in the presence of rapamycin and PD 98059) increased the .sup.32P-labelling of GSK3-α and GSK3-β by 60-100% [see FIG. 4 (c)] and increased the .sup.32P-labelling of the same tryptic peptides labelled in vitro. See FIG. 4 (d). Sequence analyses established that the third residue of these, corresponding to Ser9 (GSK3-β) or Ser21 (GSK3-α), was the site of phosphorylation in each phosphopeptide, both in vitro [see FIG. 4 (b)] and in vivo (not shown). The .sup.32P-labelling of other (more acidic) tryptic phosphopeptides was not increased by insulin. See FIG. 4 (d). These peptides have been noted previously in GSK3 from A431 cells and shown to contain phosphoserine and phosphotyrosine. See Saito, Vandenheede and Cohen, Vol. 303 (1994), supra.

PKC-delta (.delta.), epsilon (.epsilon.) and zeta (.zeta.) are reported to be activated by mitogens, and PKC-.zeta. activity is stimulated in vitro by several inositol phospholipids, including PI(3, 4, 5)P3 the product of the PI 3-kinase reaction. See Andjelkovic et al., Proc Natl Acad Sci USA, Vol. 93, No. 12, pp. 5699-5704 (1995). However, purified PKC-.epsilon. [see Palmer et al., J Biol Chem, Vol. 270, No. 38, pp. 22412-22416 (1995)], PKC-.epsilon. and PKC-.zeta. (data not shown) all failed to inhibit GSK3-α or GSK3-β in vitro. Moreover, although PKC-α, β1 and .gamma. inhibit GSK3-β in vitro [see Palmer et al. (1995), supra], GSK3-α is unaffected, while their downregulation in L6 myotubes by prolonged incubation with phorbol esters abolishes the activation of MAPKAP kinase-1 in response to subsequent challenge with phorbol esters, but has no effect on the inhibition of GSK3 by insulin (not shown).

Taken together, our results identify GSK3 as a substrate for RAC-PK. The stimulation of glycogen synthesis by insulin in skeletal muscle involves the dephosphorylation of Ser residues in glycogen synthase that are phosphorylated by GSK3 in vitro. See Parker, Candwell and Cohen, Eur J Biochem, Vol. 130, No. 1, pp. 227-234 (1983). Hence the 40-50% inhibition of GSK3 by insulin, coupled with a similar activation of the relevant glycogen synthase phosphatase [see Goode, Hughes, Woodgett and Parker, J Biol Chem, Vol. 267, No. 24, pp. 16878-16882 (1992)], can account for the stimulation of glycogen synthase by insulin in skeletal muscle [see Parker, Candwell and Cohen (1983), supra] or L6 myotubes. See Goode, Hughes, Woodgett and Parker (1992), supra. The activation of glycogen synthase and the resulting stimulation of glycogen synthesis by insulin in L6 myotubes is blocked by wortmannin, but not by PD 98059 [see Dent et al., Nature, Vol. 348, pp. 302-308 (1990)], just like the activation of Akt/RAC and inhibition of GSK3. However, GSK3 is unlikely to be the only substrate of RAC-PK in vivo, and identifying other physiologically relevant substrates will be important because RAC-PKβ is amplified and over-expressed in many ovarian neoplasms. See Cheng et al. (1992), supra.

EXAMPLE 5

Activation of RAC-PK by Insulin in L6 Myotubes is Accompanied by Phosphorylation of Residues Thr308 and Ser473

Insulin induces the activation and phosphorylation of RAC-PKα in L6 myotubes. Three 10 cm dishes of L6 myotubes were .sup.32P-labelled and treated for 10 minutes with or without 100 nM wortmannin and then for 5 minutes with or without 100 nM insulin. RAC-PKα was immunoprecipitated from the lysates and an aliquot (15%) assayed for RAC-PKα activity. See FIG. 5 (a). The activities are plotted .+-. SEM for 3 experiments relative to RAC-PKα derived from unstimulated cells which was 10 mU/mg. The remaining 85% of the immunoprecipitated RAC-PKα was alkylated with 4-vinylpyridine, electrophoresed on a 10% polyacrylamide gel (prepared without SDS to enhance the phosphorylation-induced decrease in mobility) and autoradiographed. The positions of the molecular mass markers glycogen phosphorylase (97 kDa), bovine serum albumin (66 kDa) and ovalbumin (43 kDa) are marked.

Figure 5:
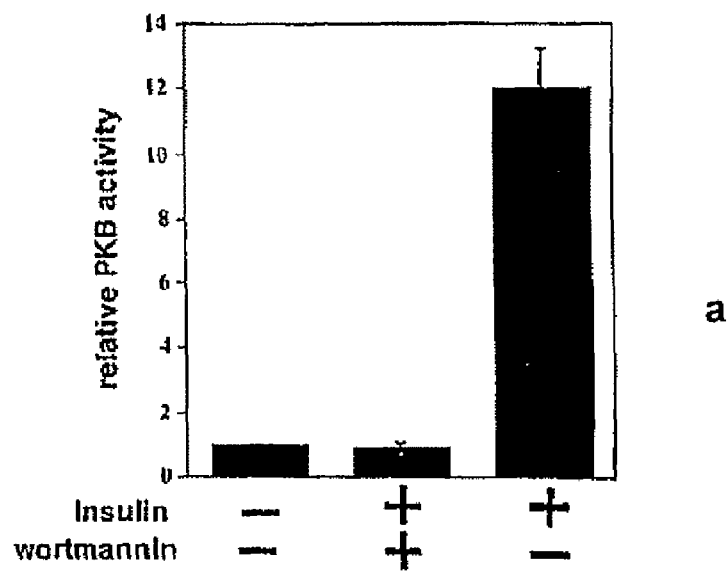
FIG. 5(a) depicts insulin inducing the activation and phosphorylation of RAC-PKα in L6 myotubes. Three 10 cm dishes of L6 myotubes were $^{32}$P-labelled and treated for 10 minutes with or without 100 nM wortmannin and then for 5 minutes with or without 100 nM insulin. RAC-PKα was immunoprecipitated from the lysates and an aliquot (15%) assayed for RAC-PKα activity. The activities are plotted ±SEM for 3 experiments relative to RAC-PKα derived from unstimulated cells which was 10 mU/mg. The remaining 85% of the immunoprecipitated RAC-PKα was alkylated with 4-vinylpyridine, electrophoresed on a 10% polyacrylamide gel (prepared without SDS to enhance the phosphorylation-induced decrease in mobility) and autoradioqraphed. The positions of the molecular mass markers glycogen phosphorylase (97 kDa), bovine serum albumin (66 kDa) and ovalbumin (43 kDa) are marked.
FIG. 5(b) depicts how insulin stimulation resulted in a 12-fold activation of RAC-PKα, and how it was accompanied by a 1.9.+-.0.3-fold increase in ±32P-labelling (4 experiments) and retardation of its mobility on SDS-polyacrylamide gels FIG. 6(a), (b), and (c) depict how insulin stimulation of L6 myotubes induces the phosphorylation of two peptides in RAC-PKα.
Figure 5:
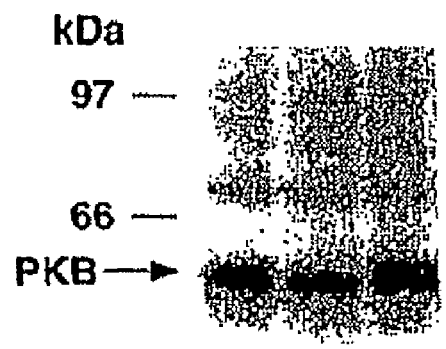

Under these conditions, insulin stimulation resulted in a 12-fold activation of RAC-PKα [see FIG. 5 (a)] and was accompanied by a 1.9.+-.0.3-fold increase in .sup.32P-labelling (4 experiments) and retardation of its mobility on SDS-polyacrylamide gels. See FIG. 5 (b). The activation of RAC-PKα, the increase in its .sup.32P-labelling and reduction in electrophoretic migration were all abolished by prior incubation of the cells with 100 nM wortmannin. Phosphoamino acid analysis of the whole protein revealed that .sup.32P-labelled RAC-PKα was phosphorylated at both serine and threonine residues and that stimulation with insulin increased both the .sup.32P-labelling of both phosphoamino acids (data not shown).

Figure 6:
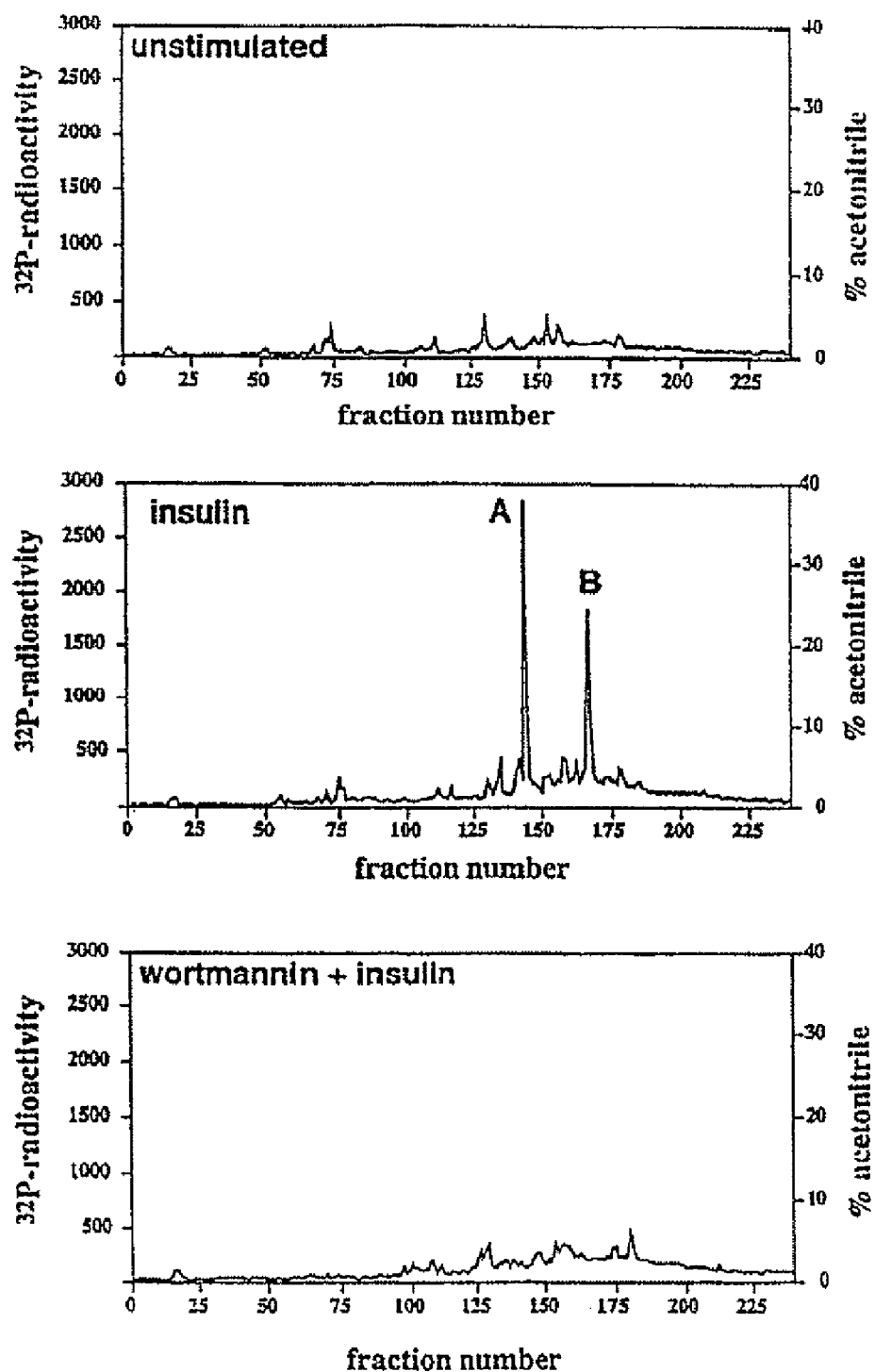
FIG. 6(a) shows a tryptic peptide map of $^{32}$P-labelled RAC-PKα from unstimulated L6 myotubes.
FIG. 6(b) shows a tryptic peptide map of $^{32}$P-labelled RAC-PKα from insulin-stimulated L6 myotubes.
FIG. 6(c) shows a tryptic peptide map of $^{32}$P-labelled RAC-PKα from L6 myotubes treated with wortmannin prior to insulin. The two major $^{32}$P-labelled peptides eluting at 23.7% and 28% acetonitrile are named Peptide A and Peptide B, respectively.

FIG. 6—Insulin stimulation of L6 myotubes induces the phosphorylation of two peptides in RAC-PKα. Bands corresponding to .sup.32P-labelled RAC-PKα, from FIG. 5 (b), were excised from the gel, treated with 4-vinylpyridine to alkylate cysteine (Cys) residues, digested with trypsin and chromatographed on a Vydac 218TP54 C18-column (Separations Group, Hesperia, Calif.) equilibrated with 0.1% (by vol) trifluoroacetic acid (TFA) and the columns developed with a linear acetonitrile gradient (diagonal line). The flow rate was 0.8 mL/min. and fractions of 0.4 mL were collected.

(a)—Tryptic peptide map of .sup.32P-labelled RAC-PKα from unstimulated L6 myotubes.

(b)—Tryptic peptide map of .sup.32P-labelled RAC-PKα from insulin-stimulated L6 myotubes.

(c)—Tryptic peptide map of .sup.32P-labelled RAC-PKα from L6 myotubes treated with wortmannin prior to insulin. The two major .sup.32P-labelled peptides eluting at 23.7% and 28% acetonitrile are named Peptide A and Peptide B, respectively. Similar results were obtained in 4 (a and b) and 2 (c) experiments.

No major .sup.32P-labelled peptides were recovered from .sup.32P-labelled RAC-PKα derived from unstimulated L6 myotubes [see FIG. 6 (a)] indicating that, in the absence of insulin, there was a low level phosphorylation at a number of sites. However, following stimulation with insulin, two major .sup.32P-labelled peptides were observed, termed A and B [see FIG. 6 (b)], whose .sup.32P-labelling was prevented if the myotubes were first preincubated with wortmannin. See FIG. 6 (c).

Figure 7:
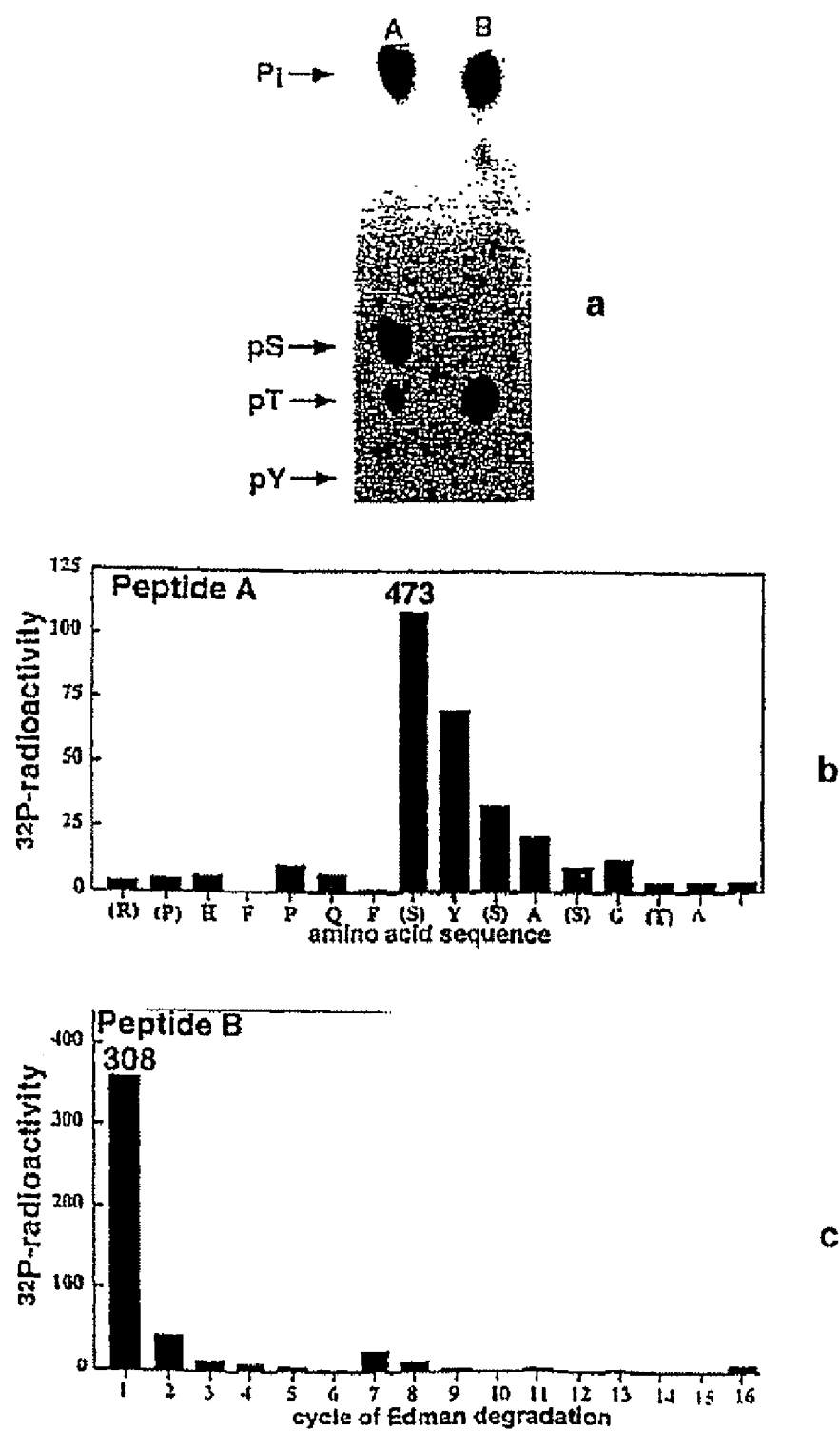
FIG. 7(a), (b), and (c) depict identification of the phosphorylation sites in Peptides A and B.
In FIG. 7(b), peptide A from FIG. 5(b3) was obtained from 50 10 cm dishes of $^{32}$P-labelled L6 myotubes was further purified by chromatography on a microbore C18-column equilibrated in 10 mM ammonium acetate pH 6.5 instead of 0.1% TFA. A single peak of $^{32}$P-radioactivity was observed at 21% acetonitrile which coincided with a peak of 214 nm absorbance. Eighty percent (80%) of the sample (1 µmol) was analysed on an Applied Biosystems 476A sequencer to determine the amino acid sequence, and the phenylthiohydantoin (Pth) amino acids identified after each cycle of Edman degradation are shown using the single letter code for amino acids. The residues in parentheses were not present in sufficient amounts to be identified unambiguously. To identify the site(s) of phosphorylation, the remaining 20% of the sample (600 cpm) was then coupled covalently to a Sequelon arylamine membrane and analysed on an Applied Biosystems 470A sequencer. $^{32}$P-radioactivity was measured after each cycle of Edman degradation.
In FIG. 7(c), peptide B from FIG. 2(b) (800 cpm) was subjected to solid phase sequencing as in (b).

FIG. 7—Identification of the phosphorylation sites in Peptides A and B.

(a)—Peptides A and B from FIG. 5 (b) (1000 cpm) were incubated for 90 minutes at 110.degree. C. in 6 M HCl, electrophoresed on thin layer cellulose at pH 3.5 to resolve orthophosphate (Pi), phosphoserine (pS), phosphthreonine (pT) and phosphotyrosine (pY) and autoradiographed.

(b)—Peptide A [see FIG. 5 (b3)] obtained from 50 10 cm dishes of .sup.32P-labelled L6 myotubes was further purified by chromatography on a microbore C18-column equilibrated in 10 mM ammonium acetate pH 6.5 instead of 0.1% TFA. A single peak of .sup.32P-radioactivity was observed at 21% acetonitrile which coincided with a peak of 214 nm absorbance. Eighty percent (80%) of the sample (1 pmol) was analysed on an Applied Biosystems 476A sequencer to determine the amino acid sequence, and the phenylthiohydantoin (Pth) amino acids identified after each cycle of Edman degradation are shown using the single letter code for amino acids. The residues in parentheses were not present in sufficient amounts to be identified unambiguously. To identify the site(s) of phosphorylation, the remaining 20% of the sample (600 cpm) was then coupled covalently to a Sequelon arylamine membrane and analysed on an Applied Biosystems 470A sequencer using the modified program described by Stokoe et al., EMBO J, Vol. 11, No. 11, pp. 3985-3994 (1992)..sup.32P-radioactivity was measured after each cycle of Edman degradation.

(c)—Peptide B from FIG. 2 (b) (800 cpm) was subjected to solid phase sequencing as in (b).

Peptide A was phosphorylated predominantly on Ser while Peptide B was labelled on Thr. See FIG. 7(a). Amino acid sequencing established that Peptide A commenced at residue 465. Only a single burst of .sup.32P-radioactivity was observed after the eighth cycle of Edman degradation [see FIG. 7 (b)], demonstrating that insulin stimulation of L6 myotubes had triggered the phosphorylation of RAC-PKα at Ser473, which is located 9 residues from the C-terminus of the protein. Phosphopeptide B was only recovered in significant amounts if .sup.32P-labelled RAC-PKα was treated with 4-vinylpyridine prior to digestion with trypsin, indicating that this peptide contained a Cys residue(s), and a single burst of .sup.32p-radioactivity was observed after the first cycle of Edman degradation. See FIG. 7 (c). This suggested that the site of phosphorylation was residue 308, since it is the only Thr in RAC-PKα that follows a Lysine (Lys) or Arginine (Arg) residue and which is located in a tryptic peptide containing a Cys residue (at position 310). The acetonitrile concentration at which phosphopeptide B is eluted from the C18-column (28%) and its isoelectric point (4.0) are also consistent with its assignment as the peptide comprising residues 308-325 of RAC-PKα. The poor recoveries of Peptide B during further purification at pH 6.5 prevented the determination of its amino acid sequence, but further experiments described below using transiently transfected 293 cells established that this peptide does correspond to residues 308-325 of RAC-PKα.

Figure 8:
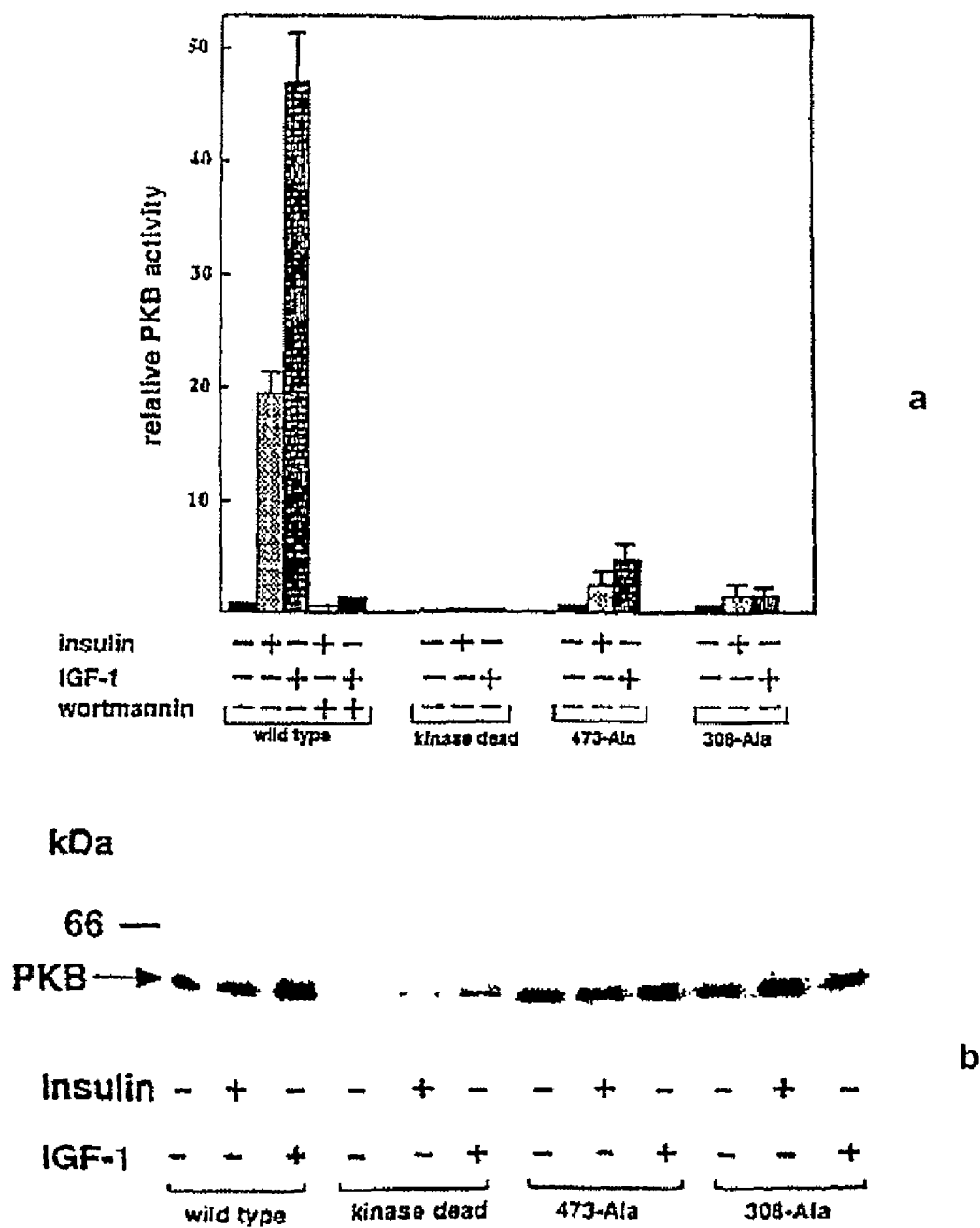
FIG. 8 depicts mapping the phosphorylation sites of RAC-PKα in transiently transfected 293 cells. Two hundred ninety-three (293) cells were transiently transfected with DNA constructs expressing WT RAC-PKα, or a hemagglutonin (HA) epitope-tagged RAC-PKα encoding the human protein, such as HA-KD RAC-PKα, HA-473A RAC-PKα or HA-308A RAC-PKα. After treatment for 10 minutes with or without 100 nM wortmannin, the cells were stimulated for 10 minutes with or without 100 nM insulin or 50 ng/mL IGF-1 in the continued presence of wortmannin. RAC-PKα was immunoprecipitated from the lysates and assayed, and activities corrected for the relative levels of expression of each HA-RAC-PKα. The results are expressed relative to the specific activity of WT HA-RAC-PKα from unstimulated 293 cells (2.5±0.5 U/mg).

FIG. 8—Mapping the phosphorylation sites of RAC-PKα in transiently transfected 293 cells. Two hundred ninety-three (293) cells were transiently transfected with DNA constructs expressing WT RAC-PKα, or a hemagglutonin (HA) epitope-tagged RAC-PKα encoding the human protein, such as HA-KD RAC-PKα, HA-473A RAC-PKα or HA-308A RAC-PKα. After treatment for 10 minutes with or without 100 nM wortmannin, the cells were stimulated for 10 minutes with or without 100 nM insulin or 50 ng/mL IGF-1 in the continued presence of wortmannin. RAC-PKα was immunoprecipitated from the lysates and assayed, and activities corrected for the relative levels of expression of each HA-RAC-PKα. The results are expressed relative to the specific activity of WT HA-RAC-PKα from unstimulated 293 cells (2.5.+−.0.5 U/mg).

(b)—Twenty (20).mu.g of protein from each lysate was electrophoresed on a 10% SDS/polyacrylamide gel and immunoblotted using monoclonal HA-antibody. The molecular markers are those used in FIG. 5 (b).

Figure 9:
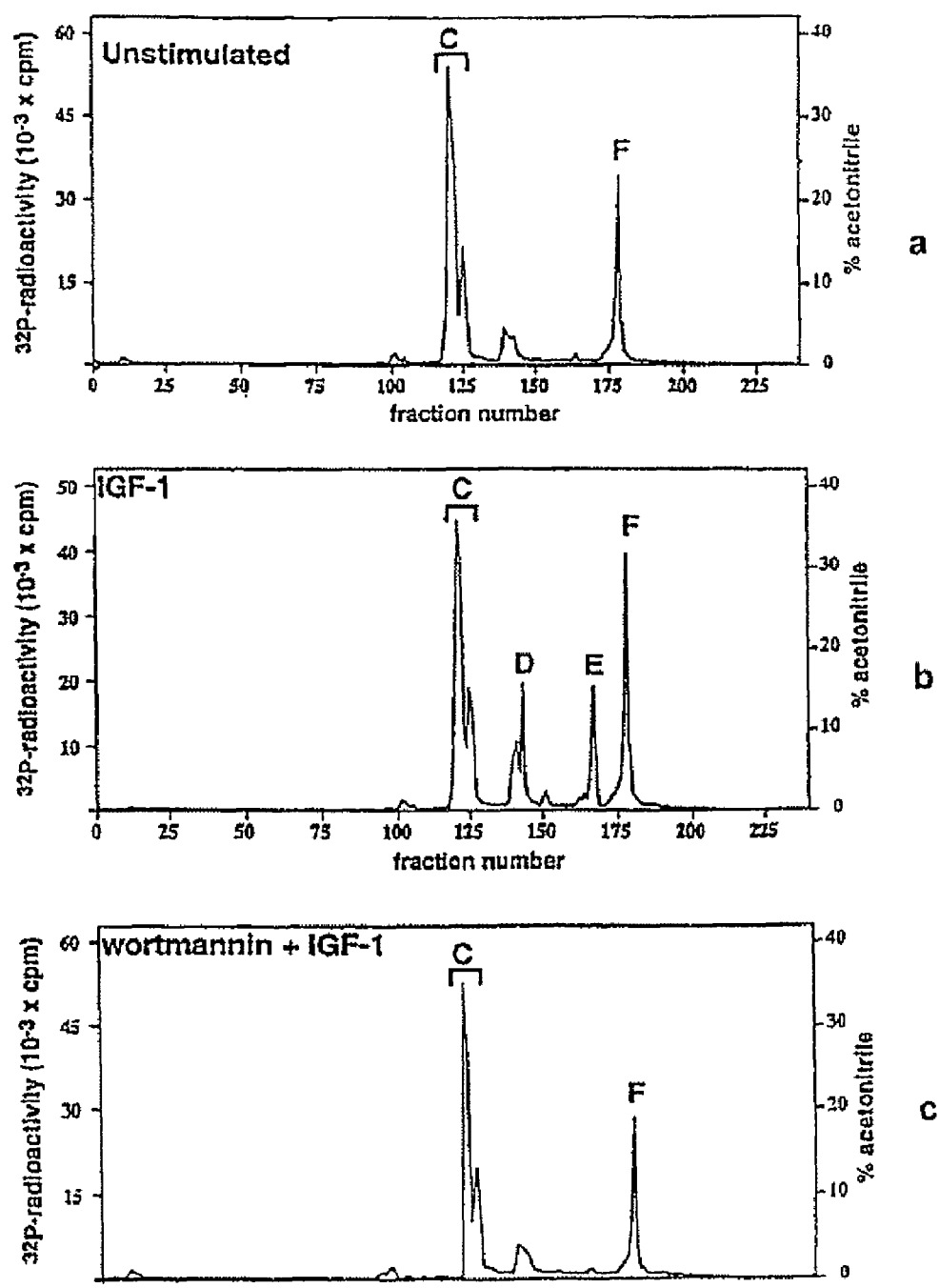
FIG. 9 shows that IGF-1 stimulation of 293 cells induces the phosphorylation of two peptides in transfected HA-RAC-PKα. Two hundred ninety-three (293) cells transiently transfected with WT HARAC-PKα DNA constructs were $^{32}$P-labelled, treated for 10 minutes without (a and b) or with (c) 100 nM wortmannin and then for 10 minutes without (a) or with (b and c) 50 ng/mL IGF-1. The $^{32}$P-labelled HA-RAC-PKα was immunoprecipitated from the lysates, treated with 4-vinylpyridine, electrophoresed on a 10% polyacrylamide gel, excised from the gel and digested with trypsin. Subsequent chromatography on a C18-column resolved 4 major phosphopeptides termed C, D, E and F. Similar results were obtained in 6 separate experiments for (a) and (b), and in 2 experiments for (c).

FIG. 9—IGF-1 stimulation of 293 cells induces the phosphorylation of two peptides in transfected HA-RAC-PKα. Two hundred ninety-three (293) cells transiently transfected with WT HARAC-PKα DNA constructs were .sup.32P-labelled, treated for 10 minutes without (a and b) or with (c) 100 nM wortmannin and then for 10 minutes without (a) or with (b and c) 50 ng/mL IGF-1. The .sup.32p-labelled HA-RAC-PKα was immunoprecipitated from the lysates, treated with 4-vinylpyridine, electrophoresed on a 10% polyacrylamide gel, excised from the gel and digested with trypsin. Subsequent chromatography on a C18-column resolved 4 major phosphopeptides termed C, D, E and F. Similar results were obtained in 6 separate experiments for (a) and (b), and in 2 experiments for (c).

Stimulation with insulin and TGF-1 resulted in 20-fold and 46-fold activation of transfected RAC-PKα, respectively [see FIG. 8 (a)], the half time for activation being 1 minute, as found with other cells. Activation of RAC-PKα by insulin or IGF-1 was prevented by prior incubation with wortmannin [see FIG. 8 (a)] and no activation occurred if 293 cells were transfected with vector alone and then stimulated with insulin or 1 GF-1 (data not shown).

Two prominent .sup.32P-labelled peptides were present in unstimulated 293 cells. See FIG. 9 (a). One, termed Peptide C, usually eluted as a doublet at 20-21% acetonitrile while the other, termed Peptide F, eluted at 29.7% acetonitrile. Stimulation with insulin or IGF-1 did not affect the .sup.32P-labelling of Peptides C and F [see FIG. 9 (a and b)], but induced the .sup.32P-labelling of 2 new peptides, termed D (23.4% acetonitrile) and E (28% acetonitrile), which eluted at the same acetonitrile concentrations as Peptides A and B from L6 myotubes [see FIG. 6 (b)] and had the same isoelectric points (7.2 and 4.0, respectively). Treatment of 293 cells expressing HA-RAC-PKα with 100 nM wortmannin, prior to stimulation with IGF-1, prevented the phosphorylation of Peptides D and E, but had no effect on the .sup.32P-labelling of Peptides C and F. See FIG. (c).

Peptides C, D, E and F were further purified by re-chromatography on the C18-column at pH 6.5 and sequenced. Peptides C gave rise to three separate (but closely eluting) .sup.32P-labelled peptides (data not shown). Amino acid sequencing revealed that all 3 commenced at residue 122 of RAC-PKα and that Ser124 was the site of phosphorylation. See FIG. 10 (a). Peptide D only contained phosphoserine and, as expected, corresponded to the RAC-PKα tryptic peptide commencing at residue 465 that was phosphorylated at Ser473. See FIG. 10 (b). Peptide E, only contained phosphothreonine and amino acid sequencing demonstrated that it corresponded to residues 308-325, the phosphorylation site being Thr308. See FIG. 10 (c). Peptide F only contained phosphothreonine and corresponded to the peptide commencing at residue 437 of RAC-PKα phosphorylated at Thr450. See FIG. 10 (d).

In the presence of phosphatidylserine, RAC-PKα binds to PIP3 with submicromolar affinity. See James et al., Biochem J, Vol. 315, Pt. 3, pp. 709-713 (1996); and Frech, Andjelkovic, Falck and Hemmings, in preparation (1996). Phosphatidyl 4,5-bisphosphate and phosphatidyl 3,4 bisphosphate bind to RAC-PKα with lower affinities and PI 3,5 bisphosphate and PI 3 phosphate did not bind at all under these conditions. See James et al. (1996), supra. The region of RAC-PKα that interacts with PIP3 is almost certainly the PH domain, because the isolated PH domain binds PIP3 with similar affinity to RAC-PKα itself [see Frech, Andjelkovic, Falck and Hemmings (1996), supra] and because the PH domain of several other proteins, such as the PH-domains of, β-spectrin and phospholipase C1, are known to interact specifically with other phosphoinositides. See Hyvonen et al., EMBO J, Vol. 14, No. 19, pp. 4676-4685 (1995); and Lemmon et al., Proc Natl Acad Sci USA, Vol. 92, No. 23, pp. 10472-10476 (1995).

The experiments described above were repeated using insulin instead of IGF-1. The results were identical, except that the .sup.32P-labelling of Peptides D and E was about 50% of the levels observed with IGF-1 (data not shown). This is consistent with the two-fold lower level of activation of RAC-PKα by insulin compared with IGF-1 (FIG. 7A).

EXAMPLE 6

MAPKAP Kinase-2 Phosphorylates Ser473 of RAC-PKα Causing Partial Activation

Ser473 of RAC-PKα lies in a consensus sequence Phe-x-x-Phe/Tyr-SerfFhr-Phe/Tyr found to be conserved in a number of PKs that participate in signal transduction pathways. See Pearson et al., EMBO J, Vol. 14, No. 21, pp. 5279-5287 (1995). In order to Identify the Ser473 kinase(s) we therefore chromatographed rabbit skeletal muscle extracts on CM-Sephadex, and assayed the fractions for protein kinases capable of phosphorylating a synthetic peptide corresponding to residues 465-478 of RAC-PKα. These studies identified an enzyme eluting at 0.3 M NaCl which phosphorylated the peptides 465-478 at the residue equivalent to Ser473 of RAC-PKα. The Ser473 kinase co-eluted from CM-Sephadex with MAPKAP kinase-2 [see Stokoe et al. (1992), supra], which is a component of a stress and cytokine-activated MAP kinase cascade. See Rouse et al., Cell, Vol. 78, No. 6, pp. 1027-1037 (1994); and Cuenda et al., FEBS Lett, Vol. 364, No. 2, pp. 229-233 (1995). The Ser473 kinase continued to cofractionate with MAPKAP kinase-2 through phenyl-Sepharose, heparin-Sepharose, Mono S and Mono Q and was immunoprecipitated quantitatively by an anti-MAPKAP kinase-2 antibody [see Gould, Cuenda, Thomson and Cohen, Biochem J, Vol. 311, pp. 735-738 (1995)] demonstrating that MAPKAP kinase-2 was indeed the Ser473 kinase we had purified.

Figure 11:
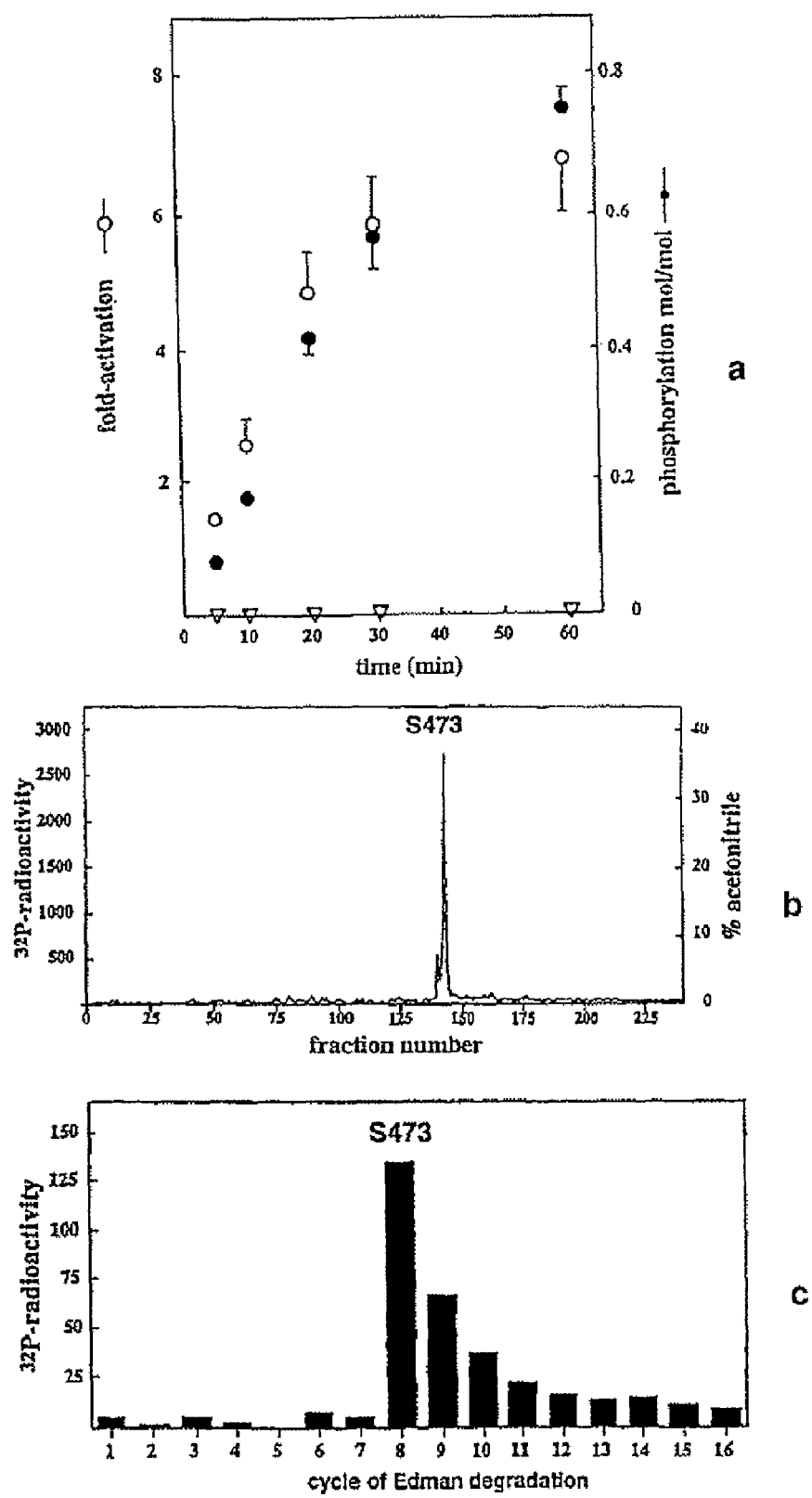
FIG. 11 depicts the immunoprecipitation of HA-RAC-PKα from the lysates of unstimulated COS-1 cells expressing these constructs.

FIG. 11—HA-RAC-PKα was immunoprecipitated from the lysates of unstimulated COS-1 cells expressing these constructs.

(a)—0.5.mu.g of immunoprecipitated HA-RAC-PKα was incubated with MAPKAP kinase-2 (50 U/mL), 10 mM magnesium acetate and 100 mM [.gamma.sup.32P]ATP in a total of 40.mu.L of Buffer B. At various times, aliquots were removed and either assayed for RAC-PKα activity (open circles) or for incorporation of phosphate into RAC-PKα (closed circles). Before measuring RAC-PKα activity, EDTA was added to a final concentration of 20 mM to stop the reaction, and the immunoprecipitates washed twice with 1.0 mL of buffer B containing 0.5 M NaCl, then twice with 1.0 mL of buffer B to remove MAPKAP kinase-2. The results are presented as .+–.SEM for 6 determinations (2 separate experiments) and RAC-PKα activities are presented relative to control experiments in which HA-RAC-PKα was incubated with MgATP in the absence of MAPKAP kinase-2 (which caused no activation). Phosphorylation was assessed by counting the .sup.32P-radioactivity associated with the band of RAC-PKα after SDS/polyacrylamide gel electrophoresis. The open triangles show the activity of immunoprecipitated HA-KD RAC-PKα phosphorylated by MAPKAP kinase-2.

(b)—HA-RAC-PKα phosphorylated for 1 hour with MAPKAP kinase-2 and 32P-.gamma.-ATP as in (a) was digested with trypsin and chromatographed on a C18-column as described in the legend for FIG. 2 (c). The major .sup.32P-labelled peptide from (b) was analyzed on the 470A sequencer as in FIG. 3 to identify the site of phosphorylation.

Bacterially-expressed MAPKAP kinase-2 phosphorylated WT HA-RAC-PKα or the catalytically-inactive mutant HA-RAC-PKα in which Lys179 had been mutated to Ala (data not shown) to a level approaching 1 mol per mole protein. See FIG. 11 (a). Phosphorylation of WT RAC-PKα was paralleled by a 7-fold increase in activity, whereas phosphorylation of the catalytically-inactive mutant did not cause any activation. See FIG. 11 (a). No phosphorylation or activation of WT HA-RAC-PKα occurred if MAPKAP kinase-2 or MgATP was omitted from the reaction (data not shown). WT HA-RAC-PKα that had been maximally-activated with MAPKAP kinase-2, was completely dephosphorylated and inactivated by treatment with protein phosphatase 2A (data not shown).

HA-RAC-PKα that had been maximally-phosphorylated with MAPKAP kinase-2 was digested with trypsin and C18-chromatography revealed a single major .sup.32P-labelled phosphoserine-containing peptide. See FIG. 11 (b). This peptide eluted at the same acetonitrile concentration [see FIG. 11 (b)] and had the same isoelectric point of 7.2 (data not shown) as the .sup.32P-labelled tryptic peptide containing Ser473 [compare FIG. 11 (b) and FIG. 6 (b)]. Solid phase sequencing gave a burst of .sup.32P-radioactivity after the eighth cycle of Edman degradation [see FIG. 11 (c)], establishing that Ser473 was the site of phosphorylation. The same .sup.32P-peptide was obtained following tryptic digestion of catalytically inactive HA-KD RAC-PKα that had been phosphorylated with MAPKAP kinase-2 (data not shown).

EXAMPLE 7

Phosphorylation of Thr308 and Ser473 Causes Synergistic Activation of RAC-PKα

The experiments described above demonstrated that phosphorylation of Ser-473 activates RAC-PKα in vitro but did not address the role of phosphorylation of Thr-308, or how phosphorylation of Thr-308 might influence the effect of Ser-473 phosphorylation on activity, or vice versa. We therefore prepared HA-tagged RAC-PKα DNA constructs in which either Ser473 or Thr308 would be changed either to Ala (to block the effect of phosphorylation) or to Asp (to try and mimic the effect of phosphorylation).

Figure 12:
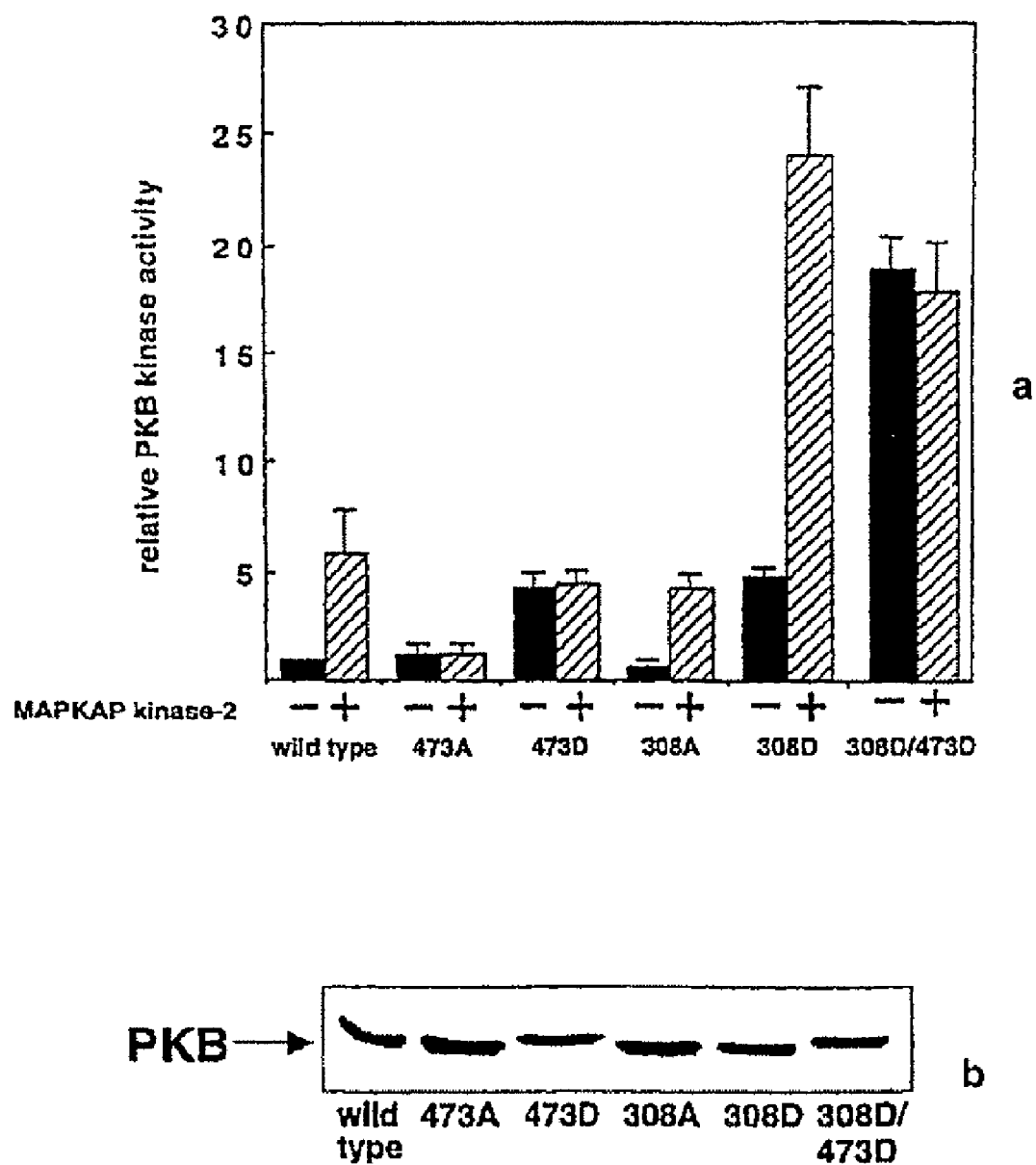
FIGS. 12(a) and 12(b) depict activation of HA-RAC-PKα mutants in vitro by MAPKAP kinase-2.

FIG. 12—Activation of HA-RAC-PKα mutants in vitro by MAPKAP kinase-2.

(a)—WT and mutant HA-RAC-PKα proteins were immunoprecipitated from the lysates of unstimulated COS-1 cells expressing these constructs and incubated for 60 minutes with MgATP in the absence (−, filled bars) or presence (+, hatched bars) of MAPKAP kinase-2 and MgATP (50 U/mL). The RAC-PKα protein was expressed as similar levels in each construct and specific activities are presented relative to WT HA-RAC-PKα incubated in the absence of MAPKAP kinase-2 (0.03 U/mg). The results are shown as the average .+–. SEM for 3 experiments.

(b)—Twenty (20).mu.g of protein from each lysate was electrophoresed on a 10% SDS/polyacrylamide gel and immunoblotted using monoclonal HA-antibody.

All the mutants were expressed at a similar level in serum-starved COS-1 cells (data not shown) and the effects of maximally phosphorylating each of them at Ser473 is shown in FIG. 12 (a). Before phosphorylation with MAPKAP kinase-2 the activity of HA-473A RAC-PKα was similar to that of unstimulated WT HA-RAC-PKα and, as expected, incubation with MAPKAP kinase-2 and MgATP did not result in any further activation of HA-473A RAC-PKα. In contrast, the activity of HA-473D RAC-PKα was 5- to 6-fold higher than that of unstimulated WT HARAC-PKα protein, and similar to that of WT HA-RAC-PKα phosphorylated at Ser473. As expected, HA-473D RAC-PKα was also not activated further by incubation with MAPKAP kinase-2 and MgATP. The activity of HA-308A RAC-PKα was about 40% that of the unstimulated WT enzyme, and after phosphorylation with MAPKAP kinase-2 is activity increased to a level similar to that of WT HA-RAC-PKα phosphorylated at Ser473. Interestingly, HA-308D RAC-PKα which (like HA473D PK) was 5-fold more active than dephosphorylated WT HA-RAC-PKα, was activated dramatically by phosphorylation of Ser473. After incubation with MAPKAP kinase-2 and MgATP, the activity of HA-308D RAC-PKα was nearly 5-fold higher than that of WT HA-RAC-PKα phosphorylated at Ser473. See FIG. 12 (b). These results suggested that the phosphorylation of either Thr308 or Ser473 leads to partial activation of RAC-PKα in vitro, and that phosphorylation of both residues results in a synergistic activation of the enzyme. This idea was supported by further experiments in which both Thr308 and Ser473 were changed to Asp. When this double-mutant was expressed in COS-1 cells it was found to possess an 18-fold higher specific activity than the dephosphorylated WT protein. As expected, the activity of this mutant was not increased further by incubation with MAPKAP kinase-2 and MgATP. See FIG. 12 (b).

EXAMPLE 8

Phosphorylation of Both Thr308 and Ser473 is Required for a High Level of Activation of RAC-PKα In Vivo FIG. 9—Effect of mutation of RAC-PKα on its activation by insulin in 293 cells.

(a)—Two hundred ninety-three (293) cells were transiently transfected with DNA constructs expressing WT RAC-PKα, HA-D473-RAC-PKα and HA-308D/473D-RAC-PKα. After treatment for 10 minutes with or without 100 nM wortmannin, cells were stimulated for 10 minutes with or without 100 nM insulin in the continued presence of wortmannin. RAC-PKα was immunoprecipitated from the lysates and assayed, and activities corrected for the relative levels of HA-RAC-PKα expression as described in the methods. The results are expressed relative to the specific activity of WT HA-RAC-PKα obtained from unstimulated 293 cells.

(b)—Twenty (20).mu.g of protein from each lysate was electrophoresed on a 10% SDS/polyacrylamide gel and immunoblotted using monoclonal HA-antibody.

Figure 13:
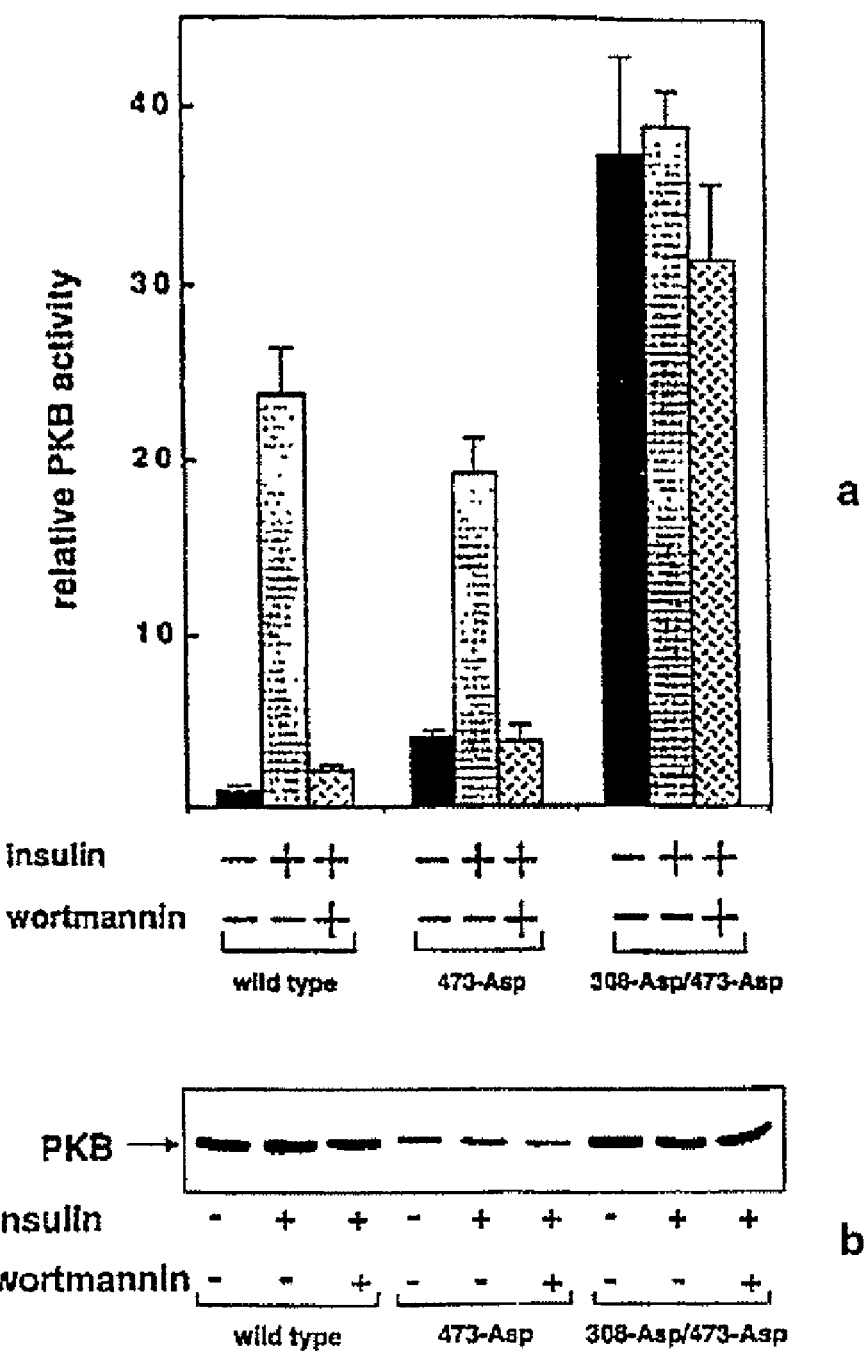
FIG. 13 shows that HA-473D RAC-PKα displayed 5-fold higher activity and the HA-308D/HA473D double-mutant 40-fold higher activity than WT HA-RAC-PKα when expressed in unstimulated cells. Following stimulation with insulin, HA-473D RAC-PKA was activated to a level similar to that observed with the WT enzyme, while the HA-308D/ HA-473D double-mutant could not be activated further.

The basal level of activity of HA-473A RAC-PKα derived from unstimulated cells was similar to that of WT RAC-PKα. See FIG. 8 (a). Stimulation of 293 cells expressing HA-473A RAC-PKα with insulin or IGF-1 increased the activity of this mutant 3- and 5-fold, respectively; i.e., to 15% of the activity of WT HA-RAC-PKα which had been transiently-expressed and stimulated under identical conditions. The basal activity of HA-308A RAC-PKα in unstimulated cells was also similar to that of WT HA-RAC-PKα derived from unstimulated cells, but virtually no activation of this mutant occurred following stimulation of the cells with insulin or IGF-1. These data are consistent with in vitro experiments and indicate that maximal activation of RAC-PKα requires phosphorylation of both Ser473 and Thr308 and that phosphorylation of both residues results in a synergistic activation of the enzyme. Consistent with these results, HA-473D RAC-PKα displayed 5-fold higher activity and the HA-308D/HA473D double-mutant 40-fold higher activity than WT HA-RAC-PKα when expressed in unstimulated cells. Following stimulation with insulin, HA-473D RAC-PKA was activated to a level similar to that observed with the WT enzyme, while the HA-308D/HA-473D double-mutant could not be activated further. See FIG. 13. As expected, activation of HA-473D RAC-PKα by insulin was prevented by wortmannin, and the activity of the HA-308D/HA-473D double-mutant was resistant to wortmannin. See FIG. 13.

EXAMPLE 9

Phosphorylation of Thr308 is Not Dependent on Phosphorylation of Ser473 or Vice Versa (in 293 Cells)

Figure 10:
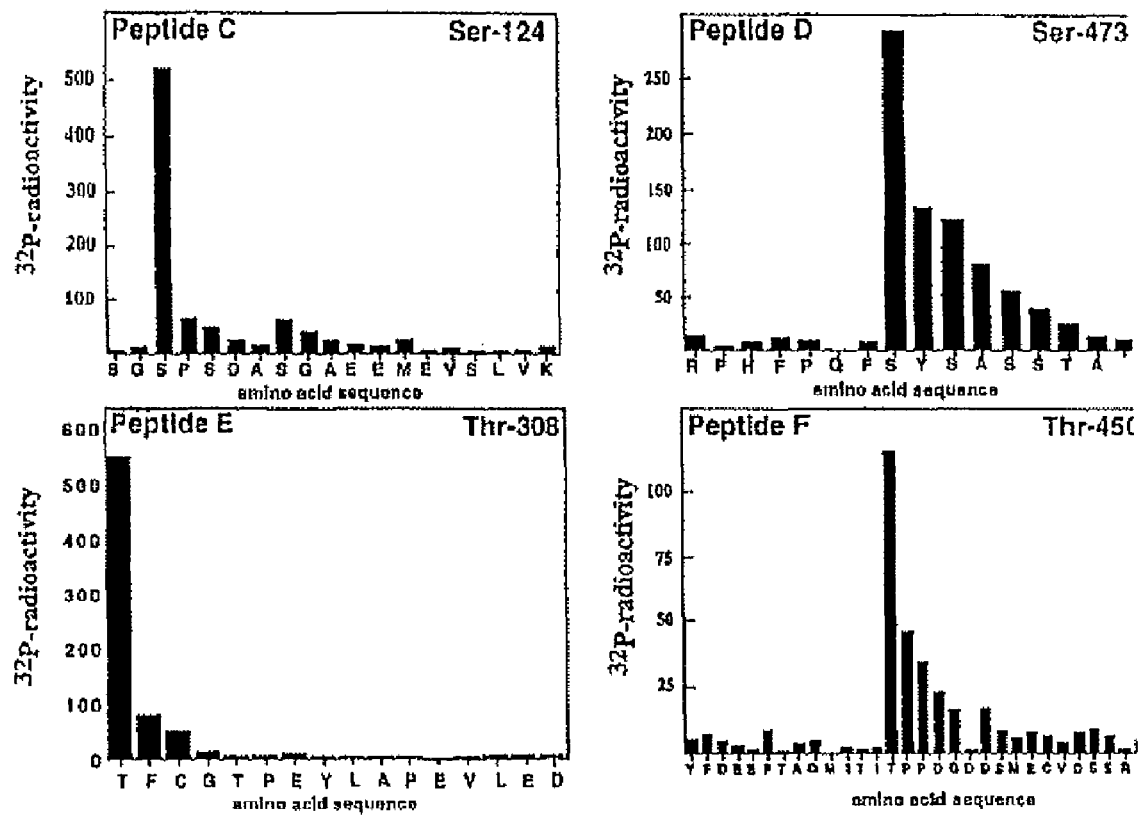
FIG. 10 shows the results of further purification of peptides C, D, E and F by re-chromatography on the C18-column at pH 6.5, followed by their sequencing. Amino acid sequencing revealed that all 3 commenced at residue 122 of RAC-PKα and that Ser124 was the site of phosphorylation (see FIG. 10(a)). Peptide D only contained phosphoserine and, as expected, corresponded to the RAC-PKα tryptic peptide commencing at residue 465 that was phosphorylated at Ser473 (see FIG. 10(b)). Peptide E only contained phosphothreonine and amino acid sequencing demonstrated that it corresponded to residues 308-325, the phosphorylation site being Thr308 (see FIG. 10(c)). Peptide F only contained phosphothreonine and corresponded to the peptide commencing at residue 437 of RAC-PKα phosphorylated at Thr450 (see FIG. 10(d)).

FIG. 10—A 10 cm dish of 293 cells were transfected with either HA-308A RAC-PKα or HA-473A RAC-PKα, .sup.32P-labelled, then stimulated for 10 minutes with either IGF-1 (50 ng/mL) or buffer. The .sup.32P-labelled RAC-PKα mutants were immunoprecipitated from the lysates, treated with 4-vinylpyridine, electrophoresed on a 10% polyacrylamide gel, excised from the gel and digested with trypsin, then chromatographed on a C18-column. The tryptic peptides containing the phosphorylated residues Ser124, Thr308, Thr450, Ser473 are marked and their assignments were confirmed by phosphoamino acid analysis and sequencing to identify the sites of phosphorylation (data not shown). The phosphopeptides containing Thr308 and Ser473 were absent if stimulation with IGF-1 was omitted, while the phosphopeptides containing Ser124 and Thr450 were present at similar levels as observed with WT RAC-PKα. See FIG. 9 (a). Similar results were obtained in 3 separate experiments.

These experiments demonstrated that IGF-1 stimulation induced the phosphorylation of HA-473A RAC-PKα at Thr308, and the phosphorylation of HA-308A RAC-PKα at Ser473. Similar results were obtained after stimulation with insulin rather than IGF-I.

EXAMPLE 10

IGF-1 or Insulin Induces Phosphorylation of Thr308 and Ser473 in a Catalytically Inactive Mutant of RAC-PKα

Figure 15:
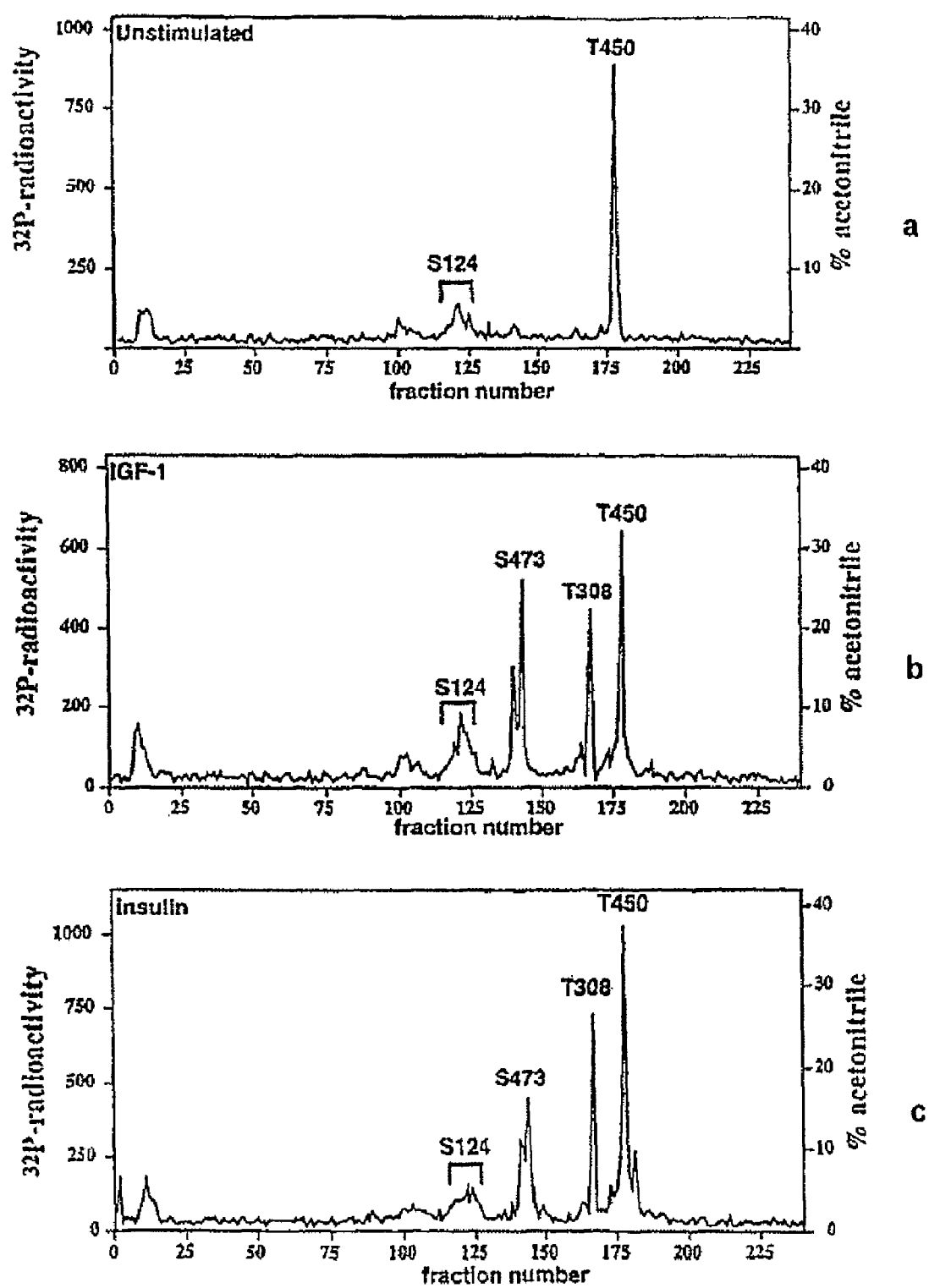
FIG. 15 demonstrates that the catalytically-inactive RAC-PKα mutant (HA-KD-RAC-PKα) expressed in 293 cells is phosphorylated at Thr308 and Ser473 after stimulation with IGF-1. Each 10 cm dish of 293 cells transiently-transfected with HA-KD-RAC-PKα DNA constructs was $^{32}$P-labelled and incubated for 10 minutes with buffer (a), 50 ng/mL IGF-1 (b) or 100 nM insulin (c). The $^{32}$P P-labelled HA-KD-RAC-PKα was immunoprecipitated from the lysates, treated with 4 vinylpyridine, electrophoresed on a 10% polyacrylamide gel, excised from the gel and digested with trypsin, then chromatographed on a C18-column. The tryptic peptides containing the phosphorylated residues Ser124, Thr308, Thr450 and Ser473 are marked. Similar results were obtained in 3 separate experiments for (b) and (b), and in 2 experiments for (c).

FIG. 15—The catalytically-inactive RAC-PKα mutant (HA-KD-RAC-PKα) expressed in 293 cells is phosphorylated at Thr308 and S er473 after stimulation with IGF-1. Each 10 cm dish of 293 cells transiently-transfected with HA-KD-RAC-PKα DNA constructs was .sup.32P-labelled and incubated for 10 minutes with buffer (a), 50 ng/mL IGF-1 (b) or 100 nM insulin (c). The .sup.32P-labelled HA-KD-RAC-PKα was immunoprecipitated from the lysates, treated with 4 vinylpyridine, electrophoresed on a 10% polyacrylamide gel, excised from the gel and digested with trypsin, then chromatographed on a C18-column. The tryptic peptides containing the phosphorylated residues Ser124, Thr308, Thr450 and Ser473 are marked. Similar results were obtained in 3 separate experiments for (b) and (b), and in 2 experiments for (c).

This "kinase dead" mutant of RAC-PKα, termed HA-KD-RAC-PKα, in which Lys179 was changed to Ala (see above) was transiently expressed in 293 cells and its level of expression found to be several-fold lower than that of WT HA-RAC-PKα expressed under identical conditions. See FIG. 8 (b). As expected, no RAC-PKα activity was detected when 293 cells expressing HA-KD-RAC-PKα, were stimulated with insulin or IGF-1. See FIG. 7 (a).

Figure 14:
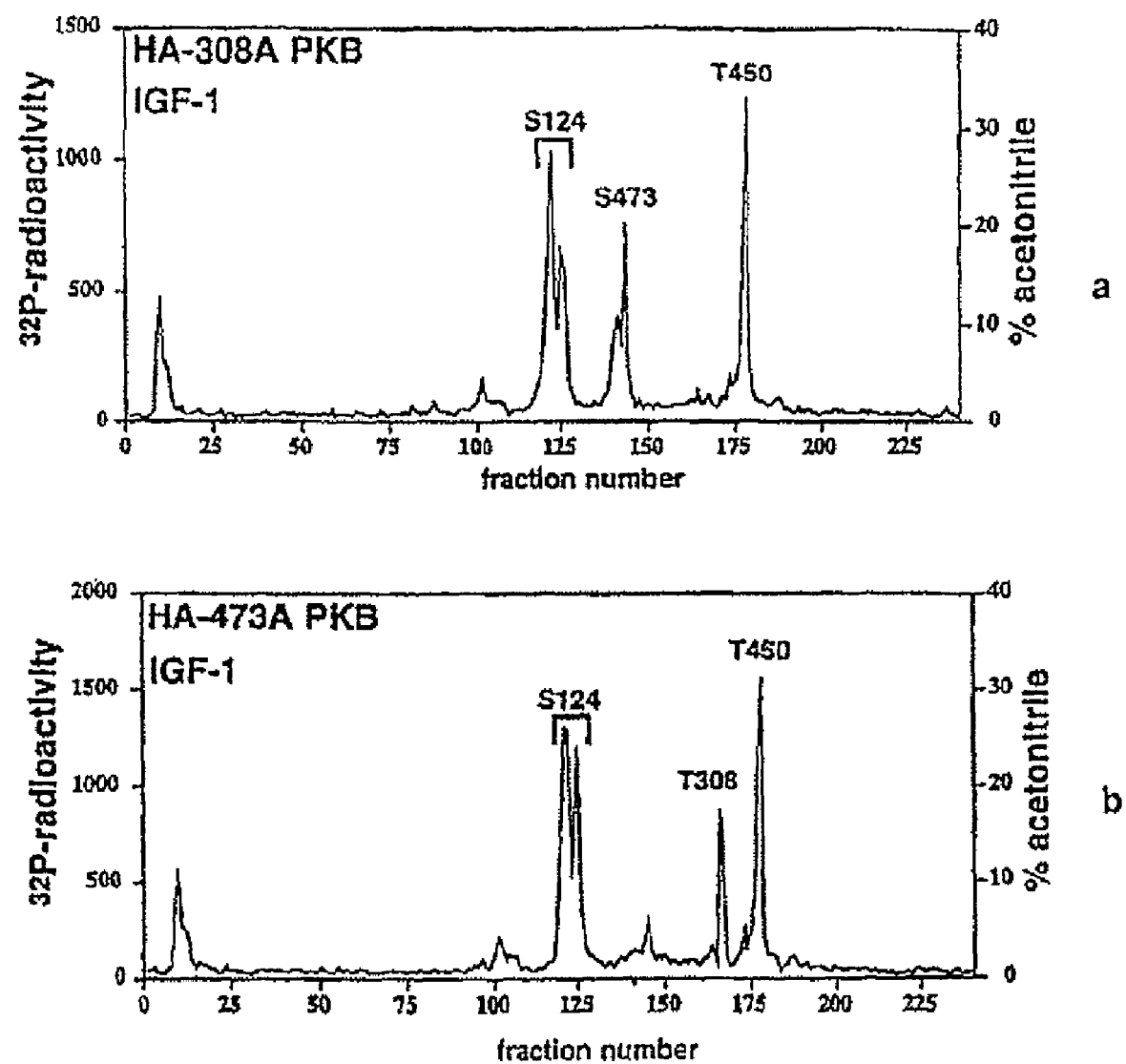
FIG. 14 demonstrates that phosphorylation of Ser124 was greatly decreased when "kinase dead" RAC-PKα was transfected into 293 cells (as described herein).

Two hundred ninety-three (293) cells that had been transiently transfected with HA-KD-RAC-PKα were .sup.32P-labelled, then stimulated with buffer, insulin or TGF-1 and sites on RAC-PKα phosphorylated under these conditions were mapped. In contrast to WT HA-RAC-PKα from unstimulated 293 cells (see FIG. 9), HA-KD RAC-PKα was phosphorylated to a much lower level at Ser124, but phosphorylated similarly at Thr450. See FIG. 15 (a). Following stimulation with IGF-1 [see FIG. 15 (b)] or insulin [see FIG. 14 (c)], HA-KD-RAC-PKα became phosphorylated at the peptides containing Thr308 and Ser473, the extent of phosphorylation of these sites being at least as high as WT RAC-PKα. Amino acid sequencing of these peptides established that they were phosphorylated at Thr308 and Ser473, respectively.

The above examples establish that RAC-PK influences GSK3 activity; that Thr308 and Ser473 are the major residues in RAC-PKα that become phosphorylated in response to insulin or IGF-1 (see FIGS. 2 and 5) and that phosphorylation of both residues is required to generate a high level of RAC-PKα activity. Thus, mutation of either Thr308 or Ser473 to Ala greatly decreased the activation of transfected RAC-PKα by insulin or IGF-1 in 293 cells. See FIG. 8. Moreover, RAC-PKα became partially active in vitro when either Thr308 or Ser473 were changed to Asp or when Ser473 was phosphorylated by MAPKAP kinase-2 in vitro, and far more active when the D308 mutant of RAC-PKα was phosphorylated by MAPKAP kinase-2 or when Thr308 and Ser473 were both mutated to Asp. See FIG. 12. Moreover, the D308/D473 double-mutant could not be activated further by stimulating cells with insulin. See FIG. 13. These observations demonstrate that the phosphorylation of Thr308 and Ser473 act synergistically to generate a high level of RAC-PKα activity.

Thr308, and the amino acid sequence surrounding it, is conserved in rat RAC-PKβ and RAC-PK.gamma. but, interestingly, Ser473 (and the sequence surrounding it) is only conserved in RAC-PKβ. In rat RAC-PK.gamma., Ser473 is missing because the C-terminal 23 residues are deleted. This suggests that the regulation of RAC-PK.gamma. may differ significantly from that of RAC-PKα and RAC-PKβ in the rat.

Thr308 is located in subdomain VIII of the kinase catalytic domain, 9 residues upstream of the conserved Ala-Pro-Glu motif, the same position as activating phosphorylation sites found in many other PKs. However, Ser473 is located C-terminal to the catalytic domain in the consensus sequence Phe-Xaa-Xaa-Phe/Tyr-Ser/Thr-Phe/Tyr which is present in several protein kinases that participate in growth factor-stimulated kinase cascades, such as p70 S6 kinase, PKC and p9orsk. See Pearson et al. (1995), supra. However, it is unlikely that a common PK phosphorylates this motif in every enzyme for the following reasons. Firstly, phosphorylation of the equivalent site in p70 S6 kinase is prevented by the immunosuppressant drug rapamycin [see Pearson et al. (1995), supra] which does not prevent the activation of RAC-PKα by insulin [see Cross et al., Nature, Vol. 378, No. 6559, pp. 785-789 (1995)] or is phosphorylation at Ser473. See D. Alessi, unpublished work. Secondly, the equivalent residue in PK cascade is phosphorylated constitutively and not triggered by stimulation with growth factors. See Tsutakawa et al., J Biol Chem, Vol. 270, No. 45, pp. 26807-26812 (1995).

MAPKAP kinase-2 is a component of a PK cascade which becomes activated when cells are stimulated with interleukin-1 or tumour necrosis factor or exposed cellular stresses. See Rouse et al. (1994), supra; and Cuenda et al. (1995), supra. MAPKAP kinase-2 phosphorylates RAC-PKα stoichiometrically at Ser473 (see FIG. 11) and this finding was useful in establishing the role of Ser473 phosphorylation in regulating RAC-PKα activity. However, although MAPKAP kinase-2 activity is stimulated to a small extent by insulin in L6 cells, no activation could be detected in 293 cells in response to insulin or IGF-1. Moreover, exposure of L6 cells or 293 cells to a chemical stress (0.5 mM sodium arsenite) strongly activated MAPKAP kinase-2 (see D. Alessi, unpublished work) as found in other cells [see Rouse et al. (1994), supra; and Cuenda et al. (1995), supra], but did not activate RAC-PKα at all. Furthermore, the drug SB 203580 which is a specific inhibitor of the PK positioned immediately upstream of MAPKAP kinase-2 [see Cuenda et al. (1995), supra], prevented the activation of MAPKAP kinase-2 by arsenite but had no effect on the activation of RAC-PKα by insulin or IGF-1. Finally, the activation of RAC-PKα was prevented by wortmannin (see FIGS. 6 and 9), but wortmannin had no effect on the activation of MAPKAP kinase-2 in L6 or 293 cells. It should also be noted that the sequence surrounding Ser473 of RAC-PKα (HFPQFSY) does not conform to the optimal consensus for phosphorylation by MAPKAP kinase-2 which requires Arg at position n–3 and a bulky hydrophobic residue at position n–5, where n is the position of the phosphorylated residue. The Km for phosphorylation of the synthetic peptide comprising residues 465-478 is nearly 100-fold higher than the Km for the standard MAPKAP kinase-2 substrate peptide (data not shown). It is therefore unlikely that MAPKAP kinase-2 mediates the phosphorylation of Ser473 in vivo.

The enzyme(s) which phosphorylates Thr308 and Ser473 in vivo does not appear to be RAC-PKα itself. Thus incubation of the partially active AsP-308 mutant with MgATP did not result in the phosphorylation of Ser473, phosphorylation of the latter residue only occurring when MAPKAP kinase-2 was added. See FIG. 11 (a) and FIG. 12. Similarly, Thr308 did not become phosphorylated when either the partially-active D473 mutant or the partially-active Ser473 phosphorylated form of RAC-PKα were incubated with M gATP. RAC-PKα when bound to lipid vesicles containing phosphatidylserine and PIP3 also fails to activate upon incubation with MgATP [see Alessi et al. (1996), supra] and after transfection into 293 cells, a "kinase dead" mutant of RAC-PKα became phosphorylated on Thr308 and Ser473 in response to insulin or IGF-1. See FIG. 14. Furthermore, HA-RAC-PKα from either unstimulated or insulin-stimulated 293 cells failed to phosphorylate the synthetic C-terminal peptide comprising amino acids 467-480.

In unstimulated L6 myotubes, the endogenous RAC-PKα was phosphorylated at a low level at a number of sites [see FIG. 6 (a)], but in unstimulated 293 cells the transfected enzyme was heavily phosphorylated at Ser124 and Thr450. See FIG. 10. Ser124 and Thr450 are both followed by praline (Pro) residues suggesting the involvement of "Pro-directed" PKs. Although, the phosphorylation of Ser124 was greatly decreased when "kinase dead" RAC-PKα was transfected into 293 cells (see FIG. 14), it would be surprising if Ser124 is phosphorylated by RAC-PKα itself because the presence of a C-terminal Pro abolishes the phosphorylation of synthetic peptides by RAC-PKα (see D. Alessi, unpublished work). Since transfected RAC-PKα is inactive in unstimulated 293 cells (see FIG. 12), phosphorylation of Ser124 and Thr450 clearly does not activate RAC-PKα directly. Ser 24 is located in the linker region between the PH domain and the catalytic domain of the mammalian RAC-PKα isoforms but, unlike Thr450, is not conserved in the Drosophila homologue. See Andjelkovic et al., Proc Nat Acad Sci USA (1995), supra.

While we do not wish to be bound by hypotheses, the results described suggest that agonists which activate PI 3-kinase are likely to stimulate RAC-PKα activity via one of the following mechanisms. Firstly, PIP3 or P13,4-bisP may activate one or more protein kinases which then phosphorylate RAC-PKα at Thr308 and Ser473. Secondly, the formation of PIP3 may lead to the recruitment of RAC-PKα to the plasma membrane where it is activated by a membrane-associated PK(s). The membrane associated Thr308 and Ser473 kinases might themselves be activated by PIP3 and the possibility that Thr308 and/or Ser473 are phosphorylated directly by PI 3-kinase has also not been excluded, because this enzyme is known to phosphorylate itself [see Dhand et al., EMBO J, Vol. 13, No. 3, pp. 522-533 (1994)] and other proteins [see Lam et al., J Biol Chem, Vol. 269, No., pp. 20648-20652 (1994)] on serine residues.

EXAMPLE 11

Molecular Basis for Substrate Specificity of RAC-PK

RAC-PKα has been shown to influence GSK3 activity. GSK3α and GSK30 are phosphorylated at Ser21 and Ser9, respectively, by 2 other insulin-stimulated PKs, namely p70 S6 kinase and MAP kinase-activated PK-1 (MAPKAP-K1, also known as p90 S6 kinase). However, these enzymes are not rate-limiting for the inhibition of GSK3 by insulin in L6 myotubes because specific inhibitors of their activation (rapamycin-p70 S6 kinase; PD 98059-MAPKAP kinase-1) have no effect. See Cross et al. (1995), supra.

The activation of PI 3-kinase is essential for many of the effects of insulin and growth factors, including the stimulation of glucose transport, fatty acid synthesis and DNA synthesis, protection of cells against apoptosis and actin cytoskeletal rearrangements. Reviewed in Carpenter and Cantley, Curr Opinion Cell Biol, Vol. 8, No. 2, pp. 153-158 (1996). These observations raise the question of whether RAC-PKα mediates any of these events by phosphorylating other proteins. To address this issue we characterized the substrate specificity requirements of RAC-PKα. We find that the optimal consensus sequence for phosphorylation by RAC-PKα is the motif Arg-Xaa-Arg-Yaa-Zaa-Ser/Thr-Hy, where Yaa and Zaa are small amino acids (other than Gly) and Hyd is a large hydrophobic residue, such as Phe or Leu. We also demonstrate that RAC-PKα phosphorylates histone H2B (a substrate frequently used to assay RAC-PKα in vitro) at Ser36 which lies in an Arg-Xaa-Arg-Xaa-Xaa-Ser-Hyd motif. These studies identified a further RAC-PKα substrate (Arg-Pro-Arg-Ala-Ala-Thr-Phe) that, unlike other peptides, is not phosphorylated to a significant extent by either p70 S6 kinase or MAPKAP-K1.

Results
Preparation of Pk-Bα

In order to examine the substrate specificity of RAC-PKα, it was first necessary to obtain a kinase preparation that was not contaminated with any other PK activities. Two hundred ninety-three (293) cells were therefore transiently-transfected with a DNA construct expressing HA-tagged RAC-PKα, stimulated with IGF-1 and the HA-RAC-PKα immunoprecipitated from the lysates. IGF-1 stimulation resulted in a 38-fold activation of RAC-PKα (see FIG. 16) and analysis of the immunoprecipitates by SDS-polyacrylamide gel electrophoresis revealed that the 60 kDa RAC-PKα was the major protein staining with coomassie Blue apart from the heavy- and light-chains of the HA monoclonal antibody. See FIG. 16, Lanes 2 and 3. The minor contaminants were present in control immunoprecipitates derived from 293 cells transfected with an empty pCMV5 vector but lacked HA-RAC-PK activity. See FIG. 16, Lane 4. Furthermore, a catalytically inactive mutant HA-RAC-PKα immunoprecipitated from the lysates of IGF-1 stimulated 293 cells had no Crosstide kinase activity. See Alessi et al. (1996), supra. Thus, all the Crosstide activity in HA-RAC-PK immunoprecipitates is catalyzed by RAC-PKα.

Figure 17:
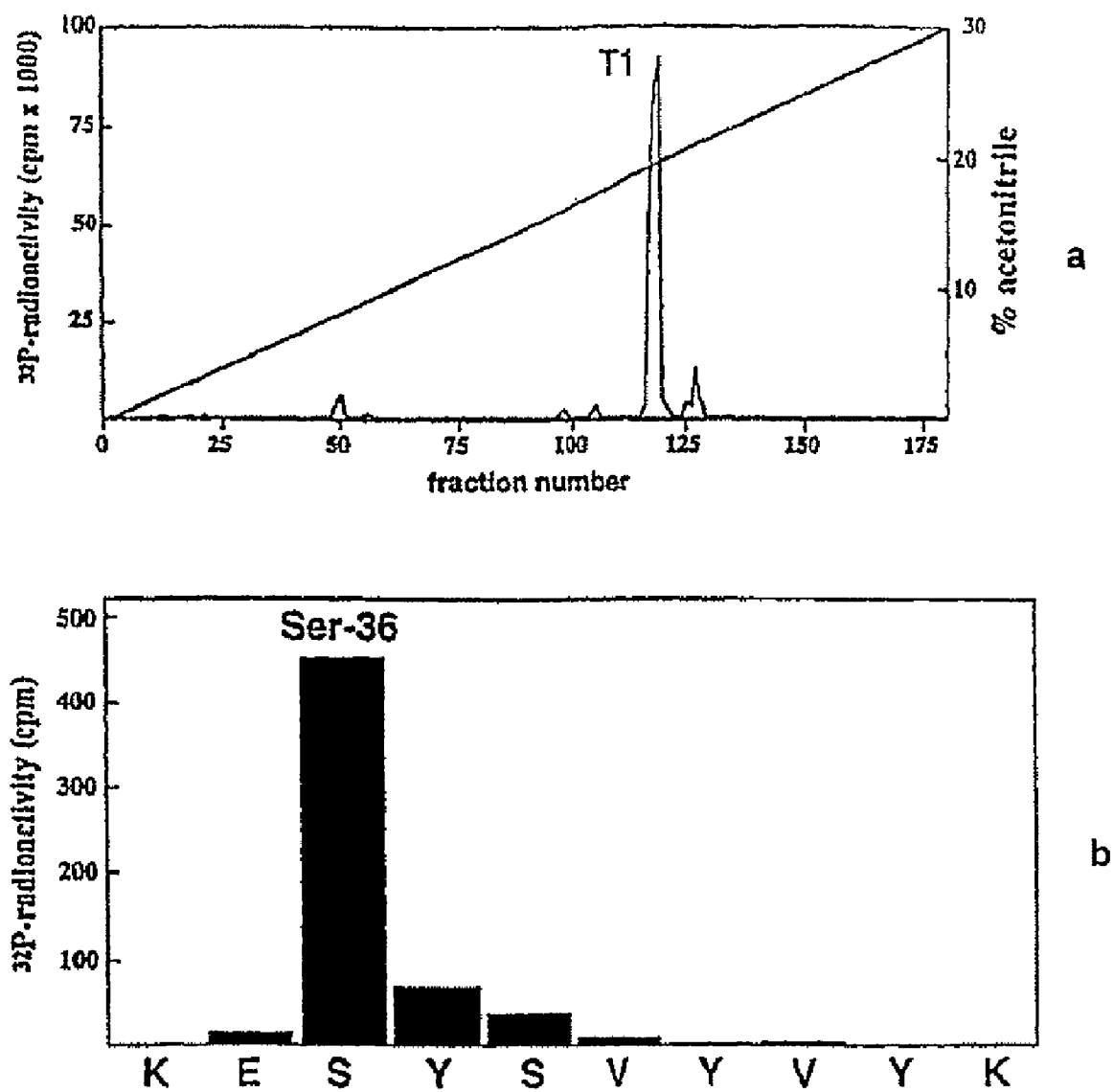
As seen in FIG. 17(b), the peptide contained phosphoserine, its sequence commenced at residue 34 of histone $H_2B$, and a single burst of radioactivity occurred after the third cycle of Edman degradation.

Identification of the residues in histone H2B phosphorylated by RAC-PKα. Currently, 3 substrates are used to assay RAC-PKα activity in different laboratories, histone H2B, MBP and Crosstide. RAC-PKα phosphorylated Crosstide with a Km of 4.mu.M and a Vmax of 260 U/mg (see Table 7.1 A, peptide 1), histone H2B with a Km of 5.mu.M and a Vmax of 68 U/mg and MBP with a Km of 5.mu.M and a Vmax of 25 U/mg. Thus the Vmax of histone H2B and MBP are 4- and 10-fold lower than for Crosstide. In order to identify the residue(s) in histone H2B phosphorylated by RAC-PKα, .sup.32P-labelled histone H2B was digested with trypsin (see Methods) and the resulting peptides chromatographed on a C18-column at pH 1.9. Only one major .sup.32P-labelled peptide (termed T1) eluting at 19.5% acetonitrile was observed. See FIG. 17 (a). The peptide contained phosphoserine (data not shown), its sequence commenced at residue 34 of histone H2B and a single burst of radioactivity occurred after the third cycle of Edman degradation [see FIG. 17 (b)], demonstrating that RAC-PKα phosphorylates histone H2B at Ser36 within the sequence Arg-Ser-Arg-Lys-Glu-Ser-Tyr. Thus, like the serine phosphorylated in Crosstide, Ser36 of histone H2B lies in an Arg-Xaa-Arg-Xaa-Xaa-Ser-Hyd motif (where Hyd is a bulky hydrophobic residue-Phe in Crosstide, Tyr in H2B).

Molecular Basis for the Substrate Specificity of RAC-PKα

To further characterize the substrate specificity requirements for RAC-PKα, we first determined the minimum sequence phosphorylated efficiently by RAC-PKα by removing residues sequentially from the C-terminal and N-terminal end of Crosstide. Removal of the N-terminal Gly and up to 3 residues from the C-terminus had little effect on the kinetics of phosphorylation by RAC-PKα. See Table 7.1A, comparing peptides 1 and 5. However any further truncation of either the N- or C-terminus virtually abolished phosphorylation. See Table 7.1A, peptides 8 and 9. The minimum peptide phosphorylated efficiently by RAC-PKα (Arg-Pro-Arg-Thr-Ser-Ser-Phe) was found to be phosphorylated exclusively at the second Ser residue as expected. Consistent with this finding, a peptide in which this Ser was changed to Ala was not phosphorylated by RAC-PKα. See Table 7.1A, peptide 7. All further studies were therefore carried out using variants of peptide 5 in Table 7.1A (see below).

A peptide in which the second Ser of peptide 5 (see Table 7.1A) was replaced by Thr was phosphorylated with a Km of 30.mu.M and an unchanged Vmax. See Table 7.1, peptide 6. All the $^{32}$P-radioactivity incorporated was present as phosphothreonine and solid phase sequencing revealed that the peptide was only phosphorylated at the second Thr residue, as expected (data not shown). Thus RAC-PKα is capable of phosphorylating Thr, as well as Ser residues, but has a preference for Ser.

We next changed either of the two Arg residues in peptide 5 to Lys. These substitutions drastically decreased the rate of phosphorylation by RAC-PKα (see Table 7.1A, peptides 10 and 11), demonstrating a requirement for Arg (and not simply any basic residue) at both positions.

We then examined the effect of substituting the residues situated immediately C-terminal to the phosphorylated Ser in peptide 5, Table 7.1 B. The data clearly demonstrate that the presence of a large hydrophobic residue at this position is critical for efficient phosphorylation, with the Km increasing progressively with decreasing hydrophobicity of the residue at this position. See Table 7.1 B, peptides 14. Replacement of the C-terminal residue with Lys increased the Km 18-fold and a substitution at this position with either Glu or praline (Pro) almost abolished phosphorylation. See Table 7.1B, peptides 5-7.

Replacement of the Thr situated 2 residues N-terminal to the phosphorylated Ser increased the Km with any amino acid tested. See Table 7.1C. Substitution with Ala only increased Km by 2- to 3-fold, but substitution with other residues was more deleterious and with Asn (a residue of similar size and hydrophilicity to Thr) phosphorylation was almost abolished. See Table 7.1C. Replacement of the Ser situated 1 residue N-terminal to the phosphorylated Ser also increased the Km with any amino acid tested, but the effects were less severe than at position n–2. See Table 7.1C. When residues n–2 and n–1 were both changed to Ala, the resulting peptide RPRAASF (SEQ ID NO: 8) was phosphorylated by RAC-PKα with a Km only 5-fold higher than RPRTSSF (SEQ ID NO: 9). In contrast the peptides RPRGGSF (SEQ ID NO: 10), RPRAGSF (SEQ ID NO: 11) and RPRGASF (SEQ ID NO: 12) were phosphorylated less efficiently. See Table 7.1C.

Comparison of the substrate specificity of RAC-PKα with MAPKAP kinase-1, and p70 S6 kinase. Since MAPKAP-K1 and p70 S6 kinase phosphorylate the same residue in GSK3 phosphorylated by RAC-PKα, and studies with synthetic peptides have established that MAPKAP-K1 and p70 S6 kinase also preferentially phosphorylate peptides in which basic residues are present at positions n–3 and n–5 [see Leighton et al., FEBS Lett, Vol. 375, No. 3, pp. 289-293 (1995)], we compared the specificities of MAPKAP-K1, p70 S6 kinase and RAC-PKα in greater detail.

MAPKAP kinase-1 and p70 S6 kinase phosphorylate the peptides KKKNRTLSVA (SEQ ID NO: 13) and KKRNRTLSVA (SEQ ID NO: 14) with extremely low Km values of 0.2-3.3.mu.M, respectively. See Table 7.2. However, these peptides were phosphorylated by RAC-PKα with 50- to 900-fold higher Km values. See Table 7.2A, peptides 1 and 2. The peptide KKRNRTLTV (SEQ ID NO: 15), which is a relatively specific substrate for p70 S6 kinase [see Leighton et al. (1995), supra] was also phosphorylated very poorly by RAC-PKα. See Table 7.2A, peptide 4.

Figure 18:
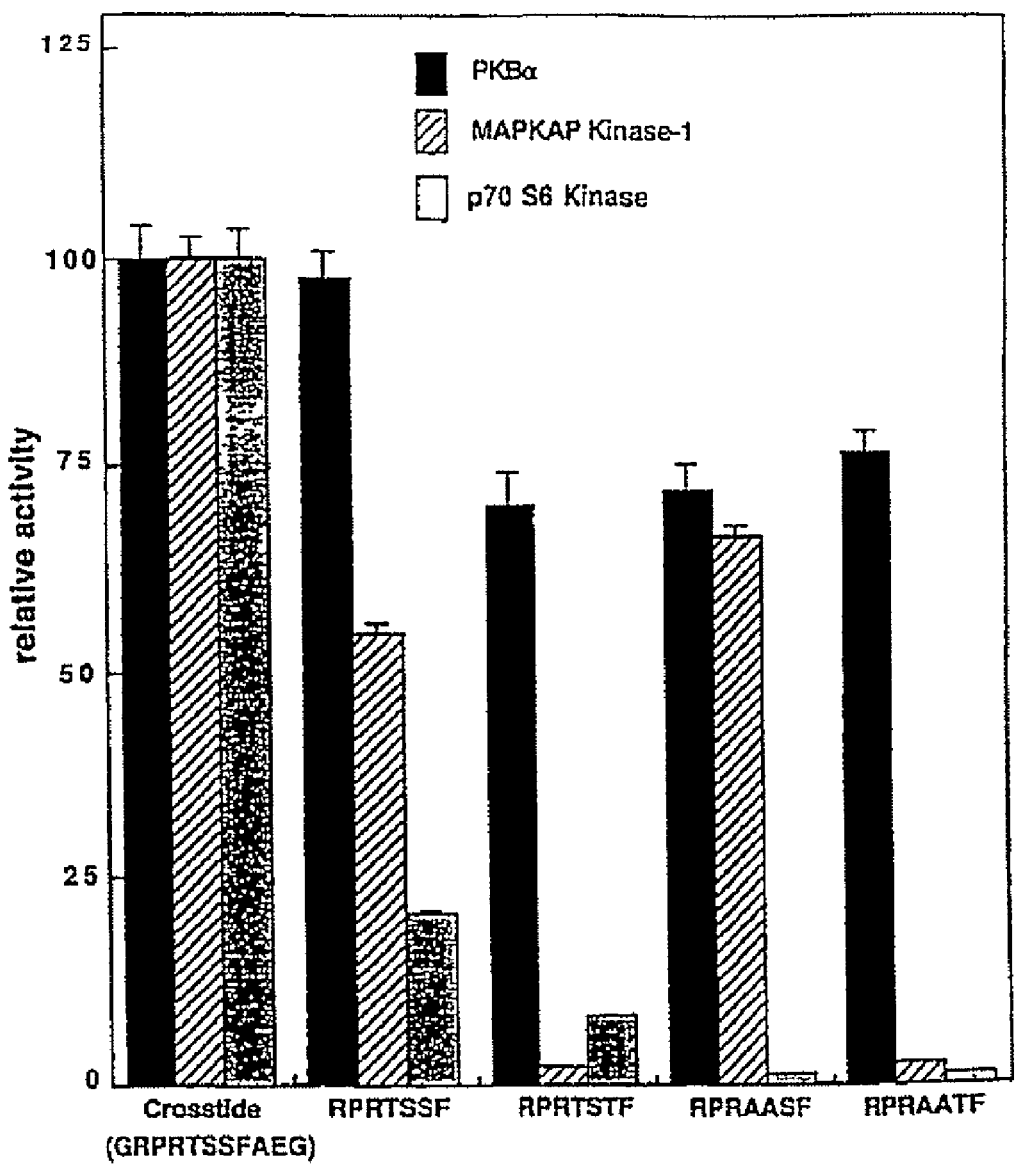
FIG. 18 depicts the identification of phosphorylated residues in histone $H_2B$ phosphorylated by RAC-PKα. $^{32}$P-labelled histone $H_2B$ was digested with trypsin and the resulting peptides chromatographed on a C18-column at pH 1.9. Only one major $^{32}$P-labelled peptide (termed T1) eluting at 19.5% acetonitrile was observed.

Crosstide is phosphorylated by p70 S6 kinase and MAPKAP kinase-1 with similar efficiency to RAC-PKα. See Leighton et al. (1995), supra; Table 7.2B, peptide 1; and FIG. 18. However, truncation of Crosstide to generate the peptide RPRTSSF (SEQ ID NO: 9) was deleterious for phosphorylation by MAPKAP-K1 and even worse for p70 S6 kinase. See Table 7.2B, peptides 1 and 2; and FIG. 18. Moreover, changing the phosphorylated Ser in RPRTSSF (SEQ ID NO: 9) to Thr increased the Km for phosphorylation by p70 S6 kinase much more than for RAC-PKα and almost abolished phosphorylation by MAPKAP-K1. See Table 7.2B, peptide 3; and FIG. 18. The peptide RPRAASF (SEQ ID NO: 8), was phosphorylated by MAPKAP-K1 with essentially identical kinetics to that of RAC-PKα; however phosphorylation by p70 S6 kinase was virtually abolished. See Table 7.2B, peptide 4; and FIG. 18. Based on these observations we synthesized the peptide RPRAATF (SEQ ID NO: 16). This peptide was phosphorylated by RAC-PKα with a Km of 25.mu.M and similar Vmax to RPRTSSF (SEQ ID NO: 9), but was not phosphorylated to a significant extent by either MAPKAP-K1 or p70 S6 kinase. See Table 7.2B, peptide 5; and FIG. 18. In FIG. 18, the PK concentration in the assays towards Crosstide were 0.2 U/mL, and each peptide substrate was assayed at a concentration of 30.mu.M. Filled bars denote RAC-PKα activity, hatched bars MAPKAP kinase-1 activity, and grey bars p70 S6 kinase activity. The activities of each PK are given relative to their activity towards Crosstide (100). The results are shown .+-.SEM for 2 experiments each carried out in triplicate.

Discussion

We have established that the minimum consensus sequence for efficient phosphorylation by RAC-PKα is Arg-Xaa-Arg-Yaa-Zaa-Ser-Hy, where Xaa is any amino acid, Yaa and Zaa are small amino acid other than Gly (Ser, Thr and Ala) and Hyd is a bulky hydrophobic residue (Phe and Leu). See Table 7.1. The heptapeptide with the lowest Km value was RPRTSSF (SEQ ID NO: 9), its Km of 5.mu.M being comparable to many of the best peptide substrates identified for other PKs. The Vmax for this peptide (250 nmoles min-1 mg-1) may be an underestimate because the RAC-PKα was obtained by immunoprecipitation from extracts of IGF-1 stimulated 293 cells over-expressing this PK, and a significant proportion of the RAC-PKα may not have been activated by IGF-1 treatment.

The requirement for Arg residues at positions n–3 and n–5 (where n is the site of phosphorylation) seems important, because substituting either residue with Lys decreases phosphorylation drastically. Ser and Thr residues were preferred at positions n–1 and n–2, although the Km value was only increased about 5-fold if both of these residues were changed to Ala. Ser was preferred at position n, since changing it to Thr caused a 6-fold increase in the Km. The peptide RPRAATF (SEQ ID NO: 16), which was phosphorylated with a Km of 25.mu.M and similar Vmax to RPRTSSF (SEQ ID NO: 9), may therefore be a better substrate for assaying RAC-PKα in partially-purified preparations, because unlike Crosstide, it contains only one phosphorylatable residue and is not phosphorylated significantly by MAPKAP-K1 or p70 S6 kinase. See Table 7.2; FIG. 18; and see below.

The Pro at position n–4 was not altered in this study because it was already clear that this residue was not critical for the specificity of RAC-PKα. Residue n–4 is Pro in GSK3β but Ala in GSK3α. Both GSK3 isoforms are equally good substrates for RAC-PKα in vitro [see Cross et al. (1995), supra], and the peptide GRARTSSFA (SEQ ID NO: 17), corresponding to the sequence in GSK3α, is phosphorylated by RAC-PKα with a Km of 10.mu.M and Vmax of 230 U/mg. See Table 7.1A, peptide 2. Moreover, in histone H2B, the residue located 4 amino acids N-terminal to the RAC-PKα phosphorylation site is Serine. See FIG. 17. The presence of Glu and Lys at positions n–1 and n–2 may explain why histone H2B is phosphorylated by RAC-PKα with a 4-fold lower Vmax than the peptide RPRTSSF (SEQ ID NO: 9).

Two other PKs which are activated by insulin and other growth factors, p70 S6 kinase and MAPKAP-K1, require basic residues at positions n–3 and n–5 [see Leighton et al. (1995), supra], explaining why they also phosphorylate and inactivate GSK3 in vitro. See Sutherland, Leighton and Cohen, Biochem J (1993), supra. Indeed, there is evidence that MAPKAP-K1 plays a role in the inhibition of GSK3 by EGF because, unlike inhibition by insulin which is prevented by inhibitors of PI 3-kinase, the inhibition of GSK3 by EGF is only suppressed partially by inhibitors of PI 3-kinase. Moreover, in NIH 3T3 cells, the inhibition of GSK3α and GSK3β by EGF is largely prevented by expression of a dominant negative mutant of MAPKAP kinase-1. See Eldar-Finkelman, Seger, Vandenheede and Krebs (1995), supra. In contrast, p70 S6 kinase is not rate limiting for the inhibition of GSK3 in the cells that have been examined so far because rapamycin, which prevents the activation of p70 S6 kinase by EGF or insulin, has no effect on the inhibition of GSK3 by these agonists. See Cross et al. (1995), supra; and Saito, Vandenheede and Cohen, Biochem J (1994), supra.

Additional similarities between p70 S6 kinase, MAPKAP-K1 and RAC-PKα include the failure to phosphorylate peptides containing Pro at position n+1 and dislike of a Lys at the same position. This suggests that, in vivo, these kinases are unlikely to phosphorylate the same residues as MAP kinases (which phosphorylates Ser/Thr-Pro motifs) or PK C, which prefers basic residues C-terminal to the site of phosphorylation. However, the present work has also revealed significant differences in the specificities of these enzymes. In particular, MAPKAP-K1 and (to a lesser extent) p70 S6 kinase can tolerate substitution of the Arg at position n−5 by Lys, whereas RAC-PKα cannot. See Tables 7.1A and 7.2A; and Leighton et al. (1995), supra. MAPKAP-K1 and p70 S6 kinase can also tolerate, to some extent, substitution of Arg at position n−3 by Lys. For example, the peptide KKRNKTLSVA is phosphorylated by MAPKAP-K1 and p70 S6 kinase with Km values of 17.mu.M and 34.mu.M, respectively, as compared to Km values of 0.7.mu.M and 1.5.mu.M for the peptide KKRNRTLSVA (SEQ ID NO: 14). See Table 7.2A. In contrast, RAC-PKα does not phosphorylate the peptide KKRNKTLSVA (see Table 7.2A) or any other peptide that lacks Arg at position n−3. RAC-PKα and p70 S6 kinase, but not MAPKAP-K1, phosphorylate Thr, as well as Ser (see Table 7.1 A) and can phosphorylate peptides lacking any residue at position n+2 [see Leighton et al. (1995), supra; and Table 7.2A], while RAC-PKα and NAPKAP-K1, but not p70 S6 kinase, can tolerate substitution of both the n−1 and n−2 positions of the peptide RPRTSSF (SEQ ID NO: 9) with Ala. See Table 7.2B. These differences explain why the peptide RPRAATF (SEQ ID NO: 16) is a relatively specific substrate for RAC-PKα.

One of the best peptide substrates for MAPKAP-K1 and p70 S6 kinase KKRNRTLSVA (SEQ ID NO: 14) was a poor substrate for RAC-PKα (see Table 7.2, peptide 2), despite the presence of Arg at positions n−3 and n−5. The presence of Leu at position n−1 and Val at position n+1 are likely to explain the high Km for phosphorylation, because RAC-PKα prefers a small hydrophilic residue at the former position and a larger hydrophobic residue at the latter position. See Tables 7.1 and 7.2.

EXAMPLE 12

This example demonstrates that coexpression of GSK3 in 293 cells with either the WT or a constitutively-activated RAC-PK results in GSK3 becoming phosphorylated and inactivated. However coexpression of a mutant of GSK3 in which Ser9 is mutated to an Ala residue is not inactivated under these conditions. These experiments provide further evidence that RAC-PKα activation can mediate the phosphorylation and inactivation of GSK3 in a cellular environment, and could be used as an assay system to search for specific RAC-PK inhibitors.

Monoclonal antibodies recognizing the sequence EFMPME (EE) (SEQ ID NO: 18) antibodies and the EQKLISEEDL (SEQ ID NO: 19) c-Myc purchased from Boehringer, Lewis, UK.

Construction of expression vectors and transfections into 293 cells. HA-RAC-PKα, HA-KD-RAC-PK and 308D/473D HA-RAC-PKα as was described previously. See Alessi et al. (1996), supra.

A DNA construct expressing human GSK3B with the EFMPME (EE) (SEQ ID NO: 18) epitope tag at the N-terminus was prepared as follows. A standard PCR reaction was carried out using as a template the human GSK3β cDNA clone in the pBluescript SK+vector and the oligonucleotides GCGGAGATCTGCCACCATGGAGTTCAT-GCCCATGGAGTCAGG GCGGCCCAGAACC (SEQ ID NO: 20) and GCGGTCCGGMCATAGTCCAGCACCAG (SEQ ID NO: 21) that incorporate a bgl II site (underlined) and a Bspe I site (double underlined). A 3-way ligation was then set up in which the resulting PCR product was subcloned as a Bgl II-Bspe I fragment together with the C-terminal Bspe I-Cla I fragment of GSK3 β into the Bgl II-Cla I sites of the pCMV5 vector. See Andersson et al., J Biol Chem, Vol. 264, No. 14, pp. 8222-8229 (1989). The construct was verified by DNA sequencing and purified using the Quiagen plasmid Mega kit according to the manufacturers protocol. The c-Myc GSK3, BA9 construct encodes GSK3β in which Ser9 is mutated to Ala and possesses a c-myc epitope tag at the C-terminus and was prepared as described in Sperber, Leight, Goedert and Lee, Neurosci Lett, Vol. 197, No. 2, pp. 149-153 (1995). The c-Myc GSK3β A9 gene was then subcloned into xba I/ECOR I sites of the pCMV5 eukaryotic expression vector.

Cotransfection of GSK3β with RAC-PKα and its assay. 293 cells growing on 10 cm diameter dishes were transfected with 10.mu.g of DNA constructs expressing EE-GSK3, Myc-GSK3A9 in the presence or absence of HA-RAC-PK, HA-KD-RAC-PK or HA-308D/473D-RAC-PK exactly as described in Alessi et al. (1996), supra. The cells were grown in the absence of serum for 16 hours prior to lysis, and then lysed in 1.0 mL of ice-cold buffer A (50 mM Tris/HCl, pH 7.5, 1 mM EDTA, 1 mM EGTA, 1% (by vol) Triton X100, 1 mM sodium orthopervanadate, 10 mM sodium glycerophosphate, 50 mM NaF, 5 mM sodium pyrophosphate, 1 uM Microcystin-LR, 0.27 M sucrose, 1 mM benzamidine, 0.2 mM phenylmethylsulphonyl fluoride, 10.mu.g/mL leupeptin and 0.1% (by vol) 2-mercaptoethanol). The lysate was centrifuged at 4.degree. C. for 10 minutes at 13,000.mu.g and an aliquot of the supernatant (100.mu.g protein) was incubated for 30 minutes on a shaking platform with 5.mu.L of Protein G-Sepharose coupled to lug of EE monoclonal antibody. The suspension was centrifuged for 1 minute at 13,000.times.g, the Protein G-Sepharose-antibody-EE-GSK3β complex washed twice with 1.0 mL of buffer A containing 0.5 M NaCl, and three times with Buffer B (50 mM Tris, pH 7.5, 0.1 mM EGTA, 0.01% (by vol) Brij-35 and 0.1% (by vol) 2-mercaptoethanol), and the immunoprecipitate assayed for GSK3 activity after incubation with either PP2A or microcystin inactivated PP2A as described previously. See Cross et al. (1994), supra.

Results

Figure 19:
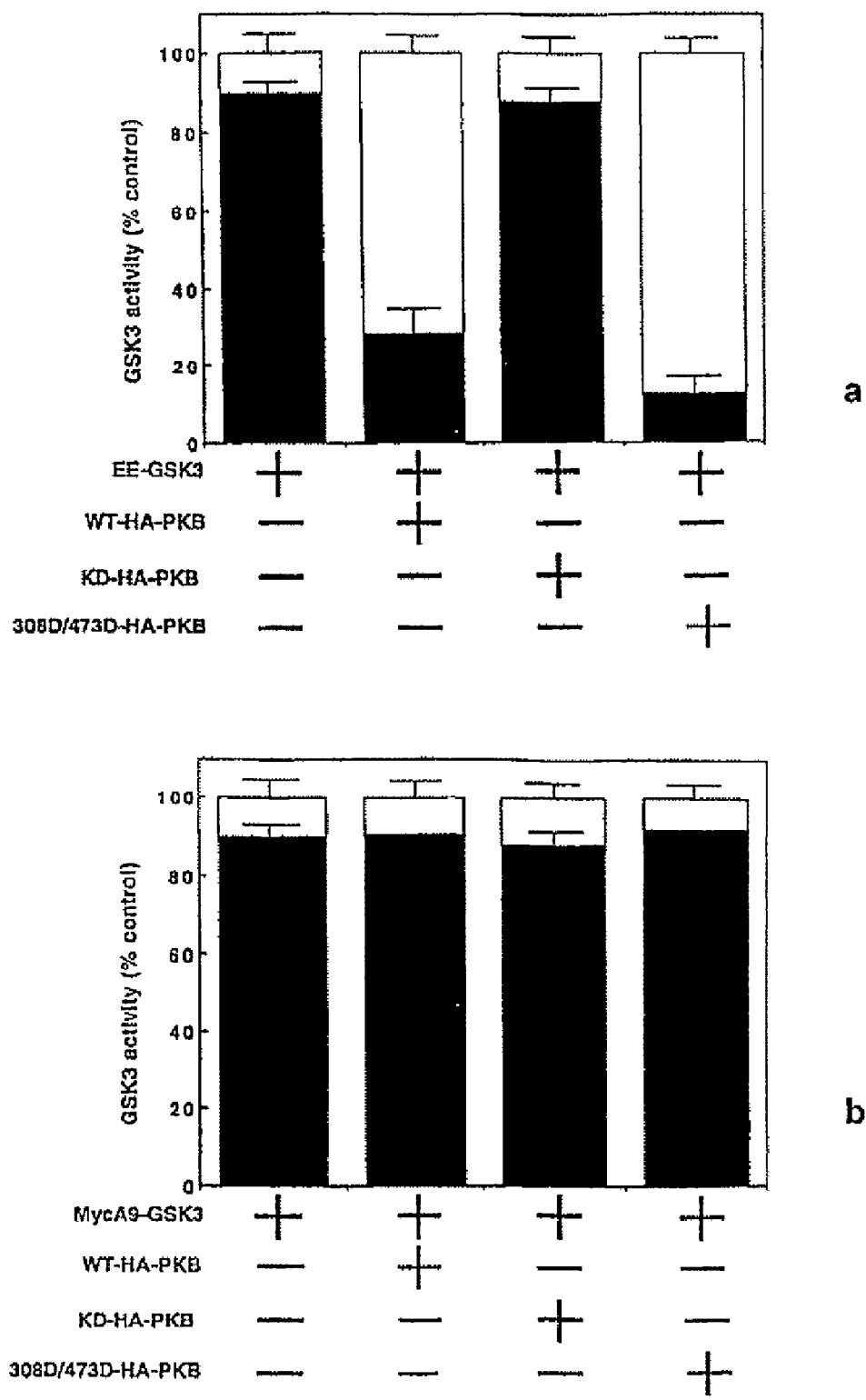
FIG. 19(a) shows that when EE-GSK3β was expressed alone or in the presence of a catalytically inactive RAC-PKα, treatment of the EE-GSK3β with PP2A only resulted in about a 12% increase in activity.
FIG. 19(b) shows that when EE-GSK3β was coexpressed with either the WT RAC-PKα or the constitutively activated 308D/473D-HA-RAC-PKα, treatment of the EE-GSK3 from these cell lysates with PP2A resulted in a 68% and 85% increase in the GSK3 activity, respectively. Coexpression of Myc-GSK3β A9 with HA-RAC-PK or the constitutively active 308D/473D-HA-RAC-PKα did not result in any significant inactivation of this mutant of GSK3 as judged by its ability to be reactivated by PP2A.

Cotransfection of GSK3β with RAC-PKα in 293 cells results in GSK3 phosphorylation and inactivation human embryonic kidney 293 cells were transfected with a DNA construct expressing EE-epitope tagged GSK3β either in the presence or absence of DNA constructs expressing WT-RAC-PKα, a catalytically inactive RAC-PKα or a constitutively active HA-(308D/473D)-RAC-PKα. Cells were serum starved for 16 hours. Thirty-six (36) hours post-transfection, the cells were lysed, and the GSK3β immunoprecipitated from the lysates using monoclonal EE antibodies and the GSK3β activity measured before and after treatment with PP2A. When EE-GSK3β was expressed alone or in the presence of a catalytically inactive RAC-PKα, treatment of the EE-GSK3β with PP2A only resulted in about a 12% increase in activity. See FIG. 19 (a). However when EE-GSK3β was coexpressed with either the WT RAC-PKα or the constitutively activated 308D/473D-HA-RAC-PKα, treatment of the EE-GSK3 from these cell lysates with PP2A resulted in a 68% and 85% increase in the GSK3 activity, respectively. Coexpression of Myc-GSK3β A9 with HA-RAC-PK or the constitutively active 308D/473D-HA-RAC-PKα did not result in any significant inactivation of this mutant of GSK3 as judged by its ability to be reactivated by PP2A. See FIG. 19 (*b*). These data demonstrate that even in a cellular environment, RAC-PKα is capable of phosphorylating GSK3β at Ser9 and inactivation of the enzyme. To estimate the relative levels of EE-GSK3β and RAC-PKα, EE-GSK3 and HA-RAC-PKα were immunoprecipitated from equal volumes of cell lysate, and the immunoprecipitates run on an SDS-polyacrylamide gel, and the gel stained with Coomassie Blue. These experiments revealed that both the WT HA-RAC-PKα and the 308D/473D-RAC-PKα were expressed at a 20- to 30-fold higher level than GSK3α, whereas KD-RAC-PKα is expressed at a level that is about 5-fold lower than that of the WT RAC-PKα. Under the conditions used for the immunoprecipitations, no RAC-PKα was co-immnuoprecipitated with GSK3β, or no GSK3β was co-immunoprecipitated with the RAC-PKα (data not shown). Coexpression of EE-GSK3β with all forms of RAC-PKα resulted in about a 2- to 3-fold decrease in the level of expression on EE-GSK3β compared to when it is expressed alone in cells.

EXAMPLE 13

Basic Assay for Identifying Agents which Affect the Activity of RAC-PK

A 40.mu.L assay mix was prepared containing PK (0.2 U/mL) in 50 mM Tris/HCl, pH 7.5, 0.1 mM EGTA, 0.1% (by vol) 2-mercaptoethanol, 2.5.mu.M PKI, PK substrate (30.mu.M), and the indicated concentration of Ro-318220 or GC 109203X (test inhibitors). After incubation on ice for 10 minutes, the reaction was started by the addition of 10.mu.L of 50 mM magnesium acetate and 0.5 mM [.gamma.sup.32P] ATP (100-200 cpm/pmol). For the assay of mixed isoforms of PKC 20.mu.M diacylglycerol, 0.5 mM CaCl.sub2 and 100.mu.M phosphatidylsene were also present in the incubations. The assays were carried out for 15 minutes at 30.degree. C., then terminated and analyzed as described. See Alessi et al., Methods Enzymol, Vol. 255, pp. 279-290 (1995). One unit of activity was that amount of enzyme that catalyzed the phosphorylation of 1 nmol os substrate in 1 minute. The final concentration of DMSO in each assay was 1% (by vol). This concentration of DMSO does not inhibit any of these enzymes. Mixed isoforms of PKC were assayed using histone H1 as substrate, while MAPKAP-K11 and p70 S6 kinase were assayed using the peptide KKRNRTLSVA (SEQ ID NO: 14). See Leighton et al. (1995), supra. PK B was assayed with the peptide GRPRTSSFAEG [9] (SEQ ID NO: 5) and MAPKAP-K2 was assayed with the peptide KKLNRTLSVA (SEQ ID NO: 27). See Stokoe, Caudwell, Cohen and Cohen, Biochem J, Vol. 296, Pt. 3, pp. 843-849 (1993). p42 MAP kinase was assayed using MBP, and MAPKK-1 and c-Raf1 were assayed as described in Alessi et al., Methods Enzymol (1995), supra.

Results

Figure 20:
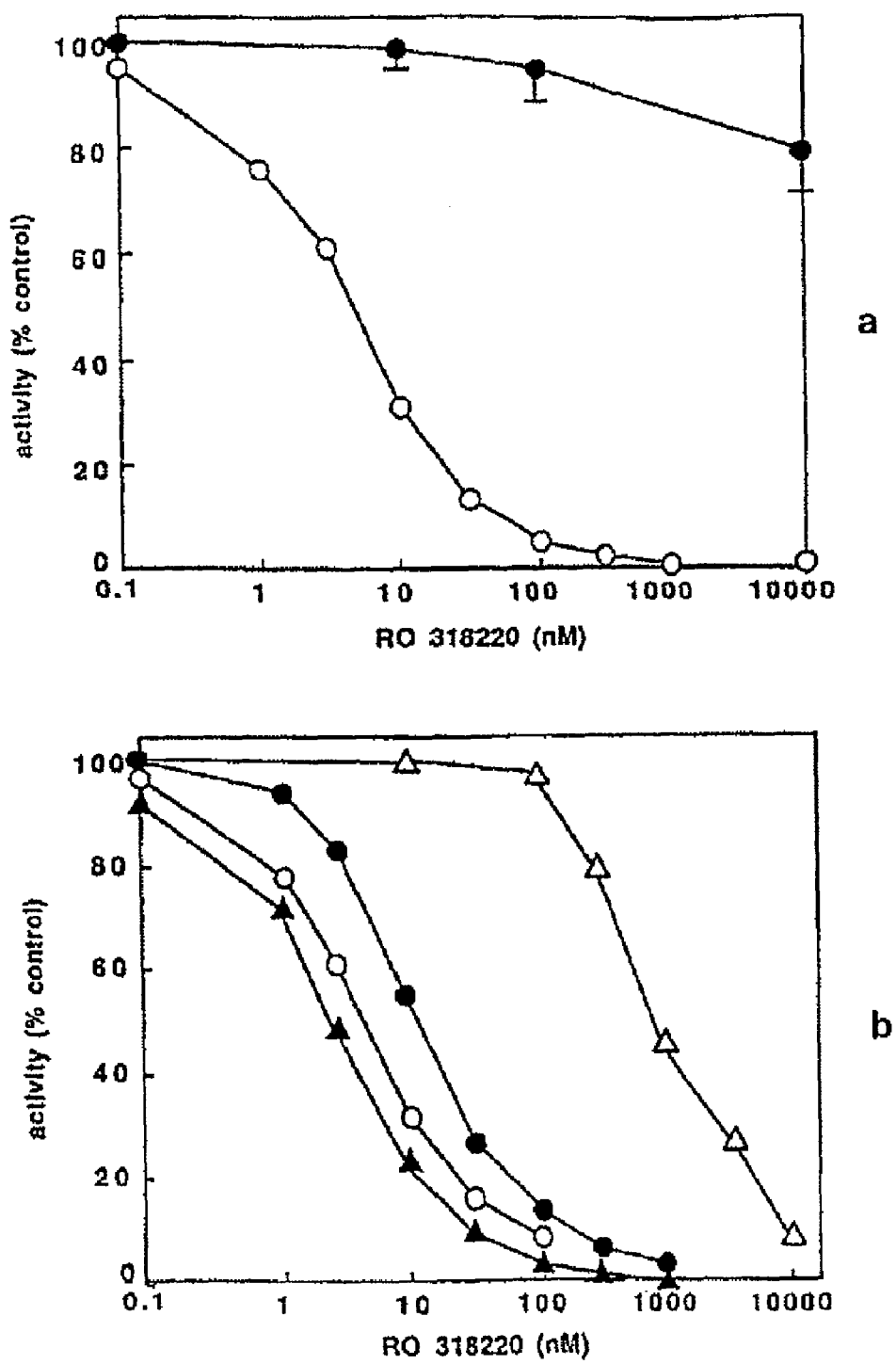

Effect of Ro 318220 and GF 109203X on PKs activated by growth factors, cytokines and cellular stresses. The mixed isoforms of PKC were potently inhibited by Ro 318220, with an IC.sub.50 of 5 nM in our assay. See FIG. 20 (*a*). In contrast, a number of PKs activated by growth factors (c-Raf1, MAPKK-1 and p42 MAP kinase) and 1 PK that is activated by cellular stresses and proinflammatory cytokines (MAPKAP-K2) were not inhibited significantly by Ro 318022 in vitro. See FIG. 20 (*a*). PK B, an enzyme that is activated in response to insulin and growth factors was inhibited by Ro 318220 (IC.sub.50 of 1.mu.M) (see FIG. 20 (*b*) similar to the IC.sub.50 for PKα. However, to our surprise, MAPKAP-K1β an enzyme which lies immediately downstream of p42 and p44 MAP kinases and which is activated in response to every agonist that stimulates this pathway, was inhibited by Ro 318220 even more potently than the mixed PKC isoforms (IC.sub.50=3 nm). See FIG. 20 (*b*). The p70 S6 kinase, which lies on a distinct growth factor-stimulated signaling pathway from MAPKAP-K1, was also potently inhibited by Ro 318220 (IC.sub.50=15 nM). See FIG. 20 (*b*).

Figure 21:
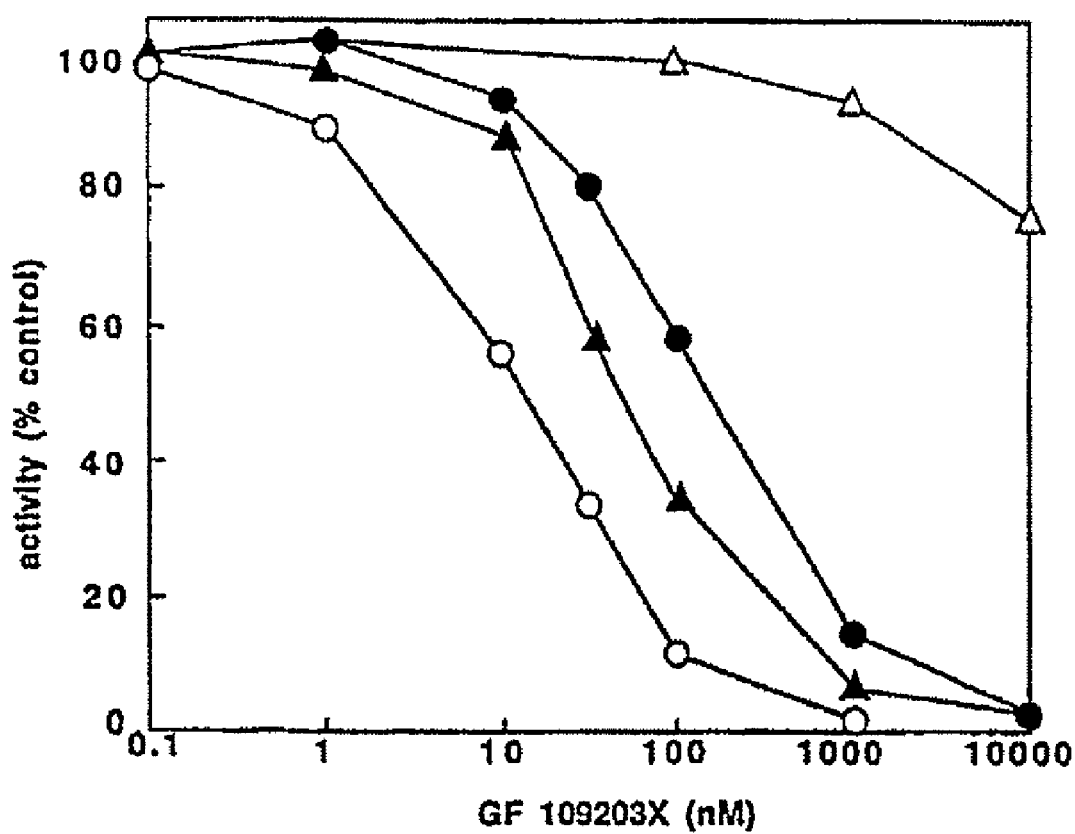
FIG. 21 shows results similar to FIG. 20, obtained using GF 109203× instead of Ro 3318220. MAPKAP-K1 B and p70 S6 kinase were potently inhibited by this compound with $IC_{50}$ values of 50 nM and 100 nM, respectively.

Similar results were obtained using GF 109203X instead of Ro 3318220. As reported previously [see Toullec et al., J Biol Chem, Vol. 266, No. 24, pp. 15771-15781 (1991)], GC 109203X inhibited the mixed isoforms of PKC (IC.sub.50=30 nM) without inhibiting PK B (see FIG. 21) or c-Raf, MAPKK-1 and p42 MAP kinase (data not shown). However MAPKAP-K1 B and p70 S6 kinase were potently inhibited by this compound with IC.sub.50 values of 50 nM and 100 nM, respectively. See FIG. 21.

General Materials and Methods

Tissue culture reagents, MBP, microcystin-LR, and IGF-1 were obtained from Life Technologies Inc. (Paisley, UK), insulin from Novo-Nordisk (Bagsvaerd, Denmark), phosphate free Dulbecco's minimal essential medium (DMEM) from (ICN, Oxon, UK), Protein G-Sepharose and CH-Sepharose from Pharmacia (Milton Keynes, UK), alkylated trypsin from Promega (Southampton, UK), 4-vinylpyridine, wortmannin and fluoroisothiocyanante-labelled antimouse IgG from goat from Sigma-Aldrich (Poole, Dorset, UK). Polyclonal antibodies were raised in sheep against the peptides RPHFPQFSYSASGTA (SEQ ID NO: 22), corresponding to the last 15 residues of rodent RAC-PKα, and MTSALATMRVDYEQIK (SEQ ID NO: 23), corresponding to residues 352-367 of human MAPKAPkinase-2, and affinity purified on peptide-CH-Sepharose. Monoclonal HA antibodies were purified from the tissue culture medium of 12CA5 hybridoma and purified by chromatography on Protein G-Sepharose. The peptide RPRHFPQFSYSAS (SEQ ID NO: 24), corresponding to residues 465478 of RAC-PKα, was synthesized on an Applied Biosystems 430A peptide synthesizer. cDNA encoding residues 46-400 of human MAPKAP kinase-2 was expressed in *E. coli* as a GST fusion protein and activated with p38/RK MAP kinase by Mr A. Clifton (University of Dundee) as described previously. See Ben-Levy et al., EMBO J, Vol. 14, No. 23, pp. 5920-5930 (1995).

Monoclonal antibodies recognizing the HA epitope sequence YPYDVPDYA (SEQ ID NO: 25), Protein G-Sepharose and histone H2B were obtained from Boehringer (Lewes, UK). MAPKAP kinase-1 [see Sutherland, Leighton and Cohen, Biochem J (1993), supra] and p70 S6 kinases [see Leighton et al. (1995), supra] were purified from rabbit skeletal muscle and rat liver, respectively.

Construction of Expression Vectors

The pECE constructs encoding the human HARAC-PKα and kinase-dead (K179A) HA-KD-RAC-PKα have already been described. See Andjelkovic et al. (1996), supra. The mutants at Ser473 (HA-473A RAC-PKα and HA-473D RAC-PKα were created by PCR using a 5' oligonucleotide encoding amino acids 406-414 and mutating 3' oligonucleotide encoding amino acids 468-480, and the resulting PCR products subcloned as CeliI-EcoRI fragment into pECE.HA-RAC-PKα. The Thr308 mutants (HA-308A RAC-PKα and HA308D RAC-PKα) were created by the 2-stage PCR technique [see No et al., Gene, Vol. 77, pp. 51-59 (1989)] and subcloned as NotI-EcoRI fragments into pECE HA-RAC-PK. The double-mutant HA-308D/473D RAC-PK was made by subcloning the CelII-EcoRI fragment encoding 473D into pECE HA-308D RAC-PKα. For construction of cytomegalovinus-driven expression constructs, BglII-XbaI fragments from the appropriate pECE constructs were subcloned into the same restriction sites of the pCMVS vector. See Andersson et al. (1989), supra.

All constructs were confirmed by restriction analysis and sequencing and purified using Quiagen Plasmid Maxi Kit according to the manufacturer's protocol. All oligonucleotide sequences are available upon request.

$^{32}$P-labelling of L6 myotubes and immunoprecipitation of PKRα. L6 cells were differentiated into myotubes on 10 cm diameter dishes. See Hundal et al., Endocrinology, Vol. 131, pp. 1165-1171 (1992). The myotubes were deprived of serum overnight in DMEM, washed three times in phosphate free DMEM and incubated for a further 1 hour with 5 mL of this medium. The myotubes were then washed twice with phosphate free DMEM and incubated for 4 hours with carrier-free [$^{32}$P]orthophosphate (1 mCi/mL). Following incubation in the presence or absence of 100 nM wortmannin for 10 minutes, the myotubes were stimulated for 5 minutes at 37.degree. C. in the presence or absence of 100 nM insulin and placed on ice. The medium was aspirated, the myotubes washed twice with ice-cold DMEM buffer and then lysed with 1.0 mL of ice-cold buffer A (50 mM Tris/HCl, pH 7.5, 1 mM EDTA, 1 mM EGTA, 1% (by vol) Triton X100, 1 mM sodium orthopervanadate, 10 mM sodium glycerophosphate, 50 mM NaF, 5 mM sodium pyrophosphate, 1.mu.M Microcystin-LR, 0.27 M sucrose, 1 mM benzamidine, 0.2 mM phenylmethylsulphonyl fluoride, 10 pg/mL leupeptin, and 0.1% (by vol) 2-mercaptoethanol). The lysates were centrifuged at 4.degree. C. for 10 minutes at 13,000.times.g and the supernatants incubated for 30 minutes on a shaking platform with 50.mu.L of Protein G-Sepharose coupled to 50.mu.g of preimmune sheep IgG. The suspensions were centrifuged for 2 minutes at 13,000.times.g and the supernatants incubated for 60 minutes with 30.mu.L of Protein G-Sepharose covalently coupled to 60.mu.g of RAC-PKα antibody. See Harlow and Lane, Antibodies—A Laboratory Manual, Cold Spring Harbor Laboratory, Cold Spring Harbor, N.Y. (1988). The Protein G-Sepharose-antibody-RAC-PK.alpha-. complex was washed eight times with 1.0 mL of buffer A containing 0.5 M NaCl, and twice with 50 mM Tris/HCl, pH 7.5, 0.1 mM EGTA and 0.1% (by vol) 2-mercaptoethanol (buffer B).

Assay of immunoprecipitated RAC-PKα and protein determinations. Three aliquots of each immunoprecipitate (each comprising only 5% of the total immunoprecipitated RAC-PKα) were assayed for RAC-PKα activity towards the peptide GRPRTSS FAEG (SEQ ID NO: 5) as described previously. See Cross et al. (1995), supra. One unit of activity was that amount which catalyzed the phosphorylation of 1 nmol of substrate in 1 minute. Protein concentrations were determined by the method of Bradford, Anal Biochem, Vol. 72, pp. 248-254 (1976).

Tryptic digestion of in vivo phosphorylated RAC-PKα. The immunoprecipitated RAC-PKα was added to an equal volume of 2% (by mass) SDS and 2% (by vol) 2-mercaptoethanol, and incubated for 5 minutes at 100.degree. C. After-cooling to room temperature, 4-vinylpyridine was added to a final concentration of 2% (by vol) and the mixture was incubated for 1 hour at 30.degree. C. on a shaking platform, followed by electrophoresis on a 10% polyacrylamide gel. After autoradiography, the 60 kDa band corresponding to rat RAC-PKα was excised and the gel piece homogenized in 5 vols of 25 mM N-ethylmorpholine HCl, pH 7.7, containing 0.1% (by mass) SDS and 5% (by vol) 2-mercaptoethanol. The suspension was incubated for 1 hour at 37.degree. C. on a shaking platform, then centrifuged for 1 minute at 13,000.times.g and the supernatant collected. The pellet was incubated for a further 1 hour with 5 vols of the same buffer and centrifuged for 1 minute at 13,000.times.g. The 2 supernatants, containing 80-90% of the $^{32}$P-radioactivity, were combined, 0.2 vols of 100% (by mass) trichloroacetic acid added, and the sample incubated for 1 hour on ice. The suspension was centrifuged for 10 minutes at 13,000.times.g, the supernatant discarded and the pellet washed 5 times with 0.2 mL of water. The pellet was then incubated at 30.degree. C. with 0.3 mL of 50 mM Tris/HCl, pH 8.0, 0.1% (by vol) Triton X100 containing 1.mu.g of alkylated trypsin. After 3 hours, another 1.mu.g of trypsin was added and the suspension left for a further 12 hours. Guanidinium hydrochloride (8 M) was added to bring the final concentration to 1.0 M in order to precipitate any residual SDS and, after standing on ice for 10 minutes, the suspension was centrifuged for 5 minutes at 13,000.times.g. The supernatant containing 90% of the $^{32}$P-radioactivity was chromatographed on a Vydac C18-column as described in the legend to FIG. 2.

Transfection of 293 cells and immunoprecipitation of HA-tagged RAC-PKα. Human embryonic kidney 293 cells were cultured at 37.degree. C. in an atmosphere of 5% CO$_2$, on 10 cm diameter dishes in DMEM containing 10% fetal calf serum (FCS). Cells were split to a density of 2.times.10.sup.6 per 10 cm dish, and after 24 hours at 37.degree. C., the medium was aspirated and 10 mL of freshly-prepared DM EM containing 10% FCS added. Cells were transfected by a modified calcium phosphate method [see Chen and Okayama, Biotechniques, Vol. 6, No. 7, pp. 632-638 (1988)] with 1.mu.g/mL DNA per plate. Ten (10).mu.g of plasmid DNA in 0.45 mL of sterile water was added to 50.mu.L of sterile 2.5 M CaCl$_2$, and then 0.5 mL of a sterile buffer composed of 50 mM N,N-bis[2-hydroxyethyl]-2-aminoethanesulphonic acid/HCl, pH 6.96, 0.28 M NaCl and 1.5 mM Na$_2$HPO$_4$ was added. The resulting mixture was vortexed for 1 minute, allowed to stand at room temperature for 20 minutes, and then added dropwise to a 10 cm dish of 293 cells. The cells were placed in an atmosphere of 3% CO$_2$, for 16 hours at 37.degree. C., then the medium was aspirated and replaced with fresh DMEM containing 10% FCS. The cells were incubated for 12 hornus at 37.degree. C. in an atmosphere of 5% CO$_2$, and then for 12 hours in DMEM in the absence of serum. Cells were preincubated for 10 minutes in the presence of 0.1% DMSO or 100 nM wortmannin in 0.1% DMSO and then stimulated for 10 minutes with either 100 nM insulin or 50 ng/mL IGF-1 in the continued presence of wortmannin. After washing twice with ice-cold DMEM the cells were lysed in 1.0 mL of ice-cold buffer A, the lysate was centrifuged at 4.degree. C. for 10 minutes at 13,000.times.g and an aliquot of the supernatant (10.mu.g protein) was incubated for 60 minutes on a shaking platform with 5.mu.L of Protein G-Sepharose coupled to 2.mu.g of HA monoclonal antibody. The suspension was centrifuged for 1 minute at 13,000.times.g, the Protein G-Sepharose-antibody-HA-RAC-PKα complex washed twice with 1.0 mL of buffer A containing 0.5 M NaCl, and twice with buffer B, and the immunoprecipitate assayed for RAC-PKα activity as described above.

$^{32}$P-Labelling of 293 Cells Transfected with HA-RAC-PKα

Two hundred ninety-three (293) cells transfected with HA-RAC-PKα DNA constructs. were washed with phosphate-free DMEM, incubated with [$^{32}$p] orthophosphate (1 mCi/mL) as described for L6 myotubes, then stimulated with insulin or IGF1 and lysed, and RAC-PKα immunoprecipitated as described above. The NP-labelled HA-RAC-PKα immunoprecipitates were washed, alkylated with 4-vinylpyridine, electrophoresed and digested with trypsin as described above for the endogenous RAC-PKα present in rat L6 myotubes.

Transfection of COS-1 Cells and Immunoprecipitation of HA-RAC-PKα

COS-1 cells were maintained in DMEM supplemented with 10% FCS at 37.degree. C. in an atmosphere of 5% $CO_2$. Cells at 70-80% confluency were transfected by a DEAE-dextran method [see Seed and Aruffo, Proc Natl Acad Sci USA, Vol. 84, pp. 3365-3369 (1987)], and 48 hours later serum-starved for 24 hours. Cells were lysed in a buffer containing 50 mM Tris-HCl, pH 7.5, 120 mM NaCl, 1% Nonidet P-40, 25 mM NaF, 40 mM sodium-, β-glycerophosphate, 0.1 mM sodium orthopervanadate, 1 mM EDTA, 1 mM benzamidine, 1 mM phenylmethylsulphonyl fluoride and lysates centrifuged for 15 minutes at 13,000.times.g at 4.degree. C. Supernatants were pre-cleared once for 30 minutes at 4.degree. C. with 0.1 vols of 50% Sepharose 4B/25% Pansorbin (Pharmacia and Calbiochem, respectively) and HA-RAC-PKα immunoprecipitated from 1 mg of extract using the 12CA5 antibody coupled to Protein A Sepharose beads. Immunoprecipitates were washed twice with lysis buffer containing 0.5 M NaCl and once with lysis buffer.

Immunoblotting and Quantification of Levels of PKα Expression.

Cell extracts were resolved by 7.5% SDS-PAGE and transferred to Immobilon membranes (Millipore). Filters were blocked for 30 minutes in a blocking buffer containing 5% skimmed milk in 1.times.TBS, 1% Triton X-100 and 0.5% Tween 20, followed by a 2 hours incubation with the 12CA5 supernatant 1000-fold diluted in the same buffer. The secondary antibody was alkaline (Alk) conjugated anti-mouse Ig from goat (Southern Biotechnology Associates, Inc), 1000-fold diluted in the blocking buffer. Detection was performed using AP color development reagents from Bio-Rad according to the manufacturer's instructions. Quantification of levels of RAC-PKα expression was achieved by chemiluminescence, using fluoroisothiocyanante-labelled antimouse IgG from goat as the secondary antibody and the Storm 840/860 and ImageQuant software from Molecular Dynamics.

All peptides used to assay RAC-PKα, and TTYADFIAS-GRTGRRNAIHD (SEQ ID NO: 26), the specific peptide inhibitor of cyclic AMP dependent PK—PKI, were synthesized on an Applied Biosystems 431A peptide synthesizer. Their purity (>95%) was established by HPLC and electrospray mass spectrometry, and their concentrations were determined by guantitative amino acid analysis.

Preparation and Assay of RAC-PKα

Figure 16:
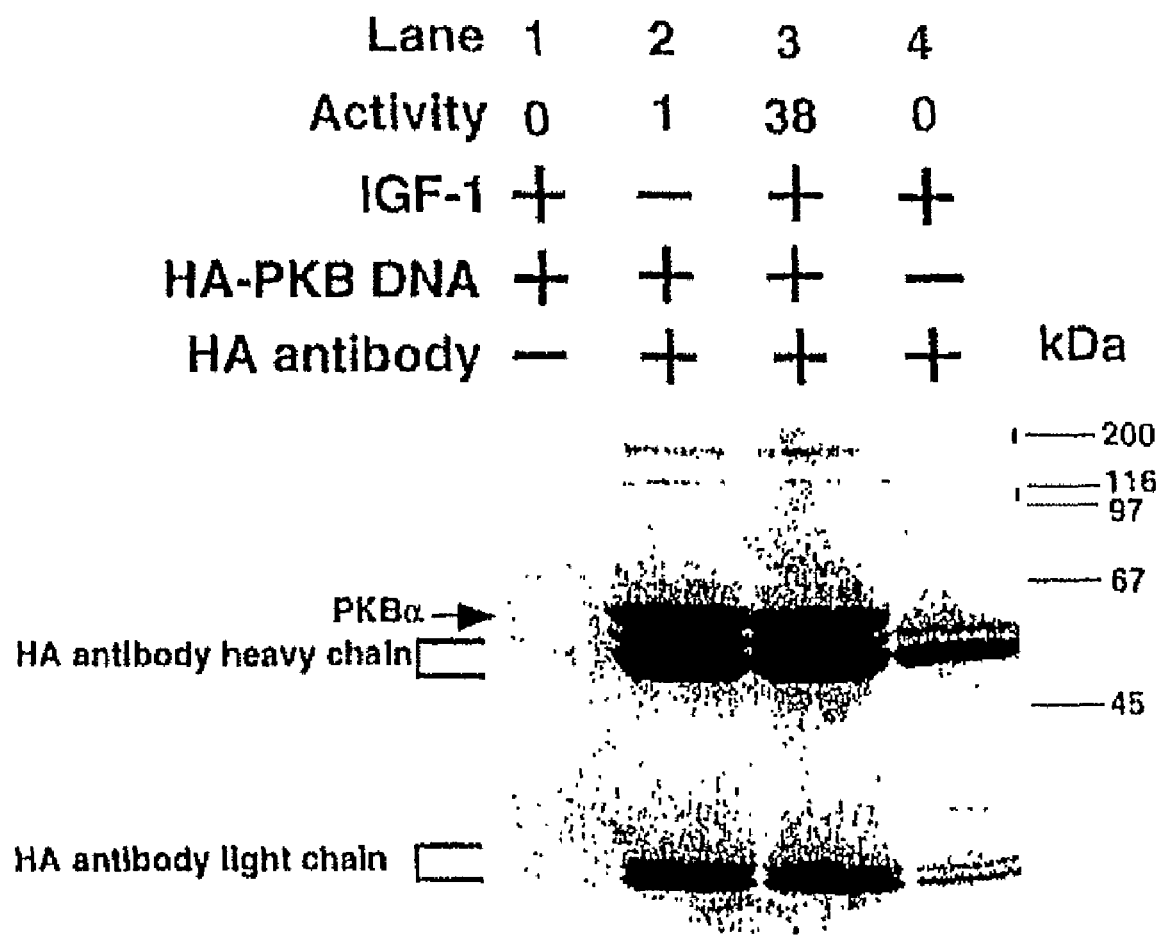
FIG. 16 shows that IGF-1 stimulation resulted in a 38-fold activation of RAC-PKα. Two hundred ninety-three (293) cells were transiently-transfected with a DNA construct expressing HA-tagged RAC-PKα, stimulated with IGF-1 and the HA-RAC-PKα immunoprecipitated from the lysates. Analysis of the immunoprecipitates by SDS-polyacrylamide gel electrophoresis revealed that the 60 kDa RAC-PKα was the major protein staining with coomassie Blue apart from the heavy- and light-chains of the HA monoclonal antibody (see FIG. 16, lanes 2 and 3).

The construction of cytomegalovirus vectors (pCMV5) of the human HA epitope-tagged WT (HA-RAC-PKα) was described previously. See Alessi et al. (1996), supra. Two hundred ninety-three (293) cells grown on 10 cm dishes were transfected with a DNA construct expressing HA-RAC-PKα using a modified calcium phosphate procedure. See Alessi et al. (1996), supra. The cells were deprived of serum for 16 hours prior to lysis and, where indicated, were stimulated for 10 minutes in the presence of 50 ng/mL IGF-1 to activate RAC-PKα. The cells were lysed in 1.0 mL ice-cold buffer A (50 mM Tris/HCl, pH 7.5, 1 mM EDTA, 1 mM EGTA, 1% (by vol) Triton X-100, 1 mM sodium orthovanadate, 10 mM sodium β-glycerophosphate, 50 mM NaF, 5 mM sodium pyrophosphate, 1.mu.M Microcystin-LR, 0.27 M sucrose, 1 mM benzamidine, 0.2 mM phenylmethylsulphonyl fluoride, 10.mu.g/mL leupeptin and 0.1% (by vol) 2-mercaptoethanol) the lysate centrifuged at 4.degree. C. for 10 minutes at 13,000.times.g and the supernatant obtained from one 10 cm dish of cells (2-3 mg protein) was incubated for 60 minutes on a shaking platform with 20 pl of Protein G-Sepharose coupled to 10.mu.g of HA monoclonal antibody. The suspension was centrifuged for 1 minute at 13,000.times.g, the Protein G-Sepharose-antibody-HA-RAC-PKα complex washed twice with 1.0 mL of buffer A containing 0.5 M NaCl, and twice with buffer B (50 mM Tris/HCl, pH 7.5, 0.1 mM EGTA, 0.01% (by vol) Brij-35 and 0.1% (by vol) 2-mercaptoethanol). The RAC-PKα immunoprecipitates were diluted in buffer B to an activity of 2.0 U/mL towards the Crosstide peptide GRPRTSSFAEG (SEQ ID NO: 5) and 0.1 mL aliquots snap frozen in liquid nitrogen and stored at –80.degree. C. No significant loss of RAC-PKα activity occurred upon thawing the RAC-PKα immunoprecipitates or during storage at –80.degree. C. for up to 3 months. The standard RAC-PKα_assay (50.mu.L) contained: 50 mM Tris/HCl, pH 7.5, 0.1 mM EGTA, 0.1% (by vol) 2-mercaptoethanol, 2.5.mu.M PKI, 0.2 U/ml RAC-PKα, Crosstide (30.mu.M), 10 mM magnesium acetate and 0.1 mM [$Y^{32}P$]ATP (100-200 cpm/pmol). The assays were carried out for 15 minutes at 30.degree. C., the assay tubes being agitated continuously to keep the immunoprecipitate in suspension, then terminated and analyzed as described. See Alessi et al. (1995), supra. One unit of activity was that amount of enzyme which catalyzed the phosphorylation of 1 nmol of Crosstide in 1 minute. The phosphorylation of other peptides, histone H2B and MBP were carried out in an identical manner. All the Crosstide activity in HA-RAC-PKα immunoprecipitates is catalysed by RAC-PKα (see Results) and the RAC-PKα concentration in the immunoprecipitates was estimated by densitometric scanning of Coomassie blue-stained polyacrylamide gels, using bovine serum albumin as a standard. Protein concentrations were determined by the method of Bradford using bovine serum albumin as standard. See Bradford (1976), supra. Michaelis constants (Km) and Vmax values were determined from double reciprocal plots of 1/V against 1/S, where V is the initial rate of phosphorylation, and S is the substrate concentration. The standard errors for all reported kinetic constants were within <.+–0.20%, and the data is reported as mean values for 3 independent determinations. FIG. 16 shows the results relative to those obtained for unstimulated RAC-PKα.

Tryptic Digestion of Histone 2B Phosphorylated by RAC-PKα

Histone H2B (30.mu.M) was phosphorylated with 0.2 U/mL HA-RAC-PKα. After 60 minutes, 0.2 vol of 100% (by mass) trichloroacetic acid was added, and the sample incubated for 1 hour on ice. The suspension was centrifuged for 10 minutes at 13,000.times.g, the supernatant discarded and the pellet washed 5 times with 0.2 mL of ice-cold acetone. The pellet was re-suspended in 0.3 mL of 50 mM Tris/HCl, pH 8.0, 0.1% (by vol) reduced Triton-X100 containing 2 pg of alkylated trypsin and, after incubation for 16 hours at 30.degree. C., the digest was centrifuged for 5 minutes at 13,000.times.g. The supernatant, containing 95% of the .sup.32P-radioactivity, was chromatographed on a Vydac C18-column equilibrated with 0.1% (by vol) TFA in water. With reference to the results shown in FIG. 17, the columns were developed with a linear acetonitrile gradient (diagonal line) at a flow rate of 0.8 mL/min. and fractions of 0.4 mL were collected.

(a) Tryptic peptide map of .sup.32P-labelled histone H2B, 70% of the radioactivity applied to the column was recovered from the major .sup.32P-peptide eluting at 19.5% acetonitrile.

(b) A portion of the major .sup.32P-peptide (50 pmol) was analyzed on an Applied Biosystems 476A sequencer, and the Pth amino acids identified after each cycle of Edman degradation are shown using the single-letter code for amino acids. A portion of the major .sup.32P-peptide (1000 cpm) was then coupled covalently to a Sequelon arylamine membrane and analyzed on an Applied Biosystems 470A sequencer using the modified program. See Stokoe et al. (1992), supra..sup.32P-radioactivity was measured after each cycle of Edman degradation.

TABLE 7.1

Molecular Basis for the substrate specificity of RAC-PKα

| | Peptides | Km (μM) | Vmax (U/mg) | V (0.1 mM) |
|---|---|---|---|---|
| A | | | | |
| 1. | GRPRTSSFAEG | 4 | 250 | 100 |
| 2. | RPRTSSFA | 8 | 305 | 109 |
| 3. | GRPRTSSF | 8 | 385 | 129 |
| 4. | RPRTSSF | 5 | 260 | 105 |
| 5. | RPRTSTF | 30 | 243 | 78 |
| 6. | RPRTSAF | — | 0 | |
| 7. | PRTSSF | — | 0 | |
| 8. | RPRTSS | >500 | ND | 2 |
| 9. | KPRTSSF | >500 | ND | 4 |
| 10. | RPKTSSF | >500 | ND | 2 |
| B | | | | |
| 1. | RPRTSSF | 5 | 260 | 105 |
| 2. | RPRTSSL | 8 | 278 | 104 |
| 3. | RPRTSSV | 21 | 300 | 102 |
| 4. | RPRTSSA | 250 | 265 | 30 |
| 5. | RPRTSSK | 80 | 308 | 67 |
| 6. | RPRTSSE | >500 | ND | 9 |
| 7. | RPRTSSPA* | — | | 0 |
| C | | | | |
| 1. | RPRTSSF | 5 | 260 | 105 |
| 2. | RPRASSF | 12 | 230 | 89 |
| 3. | RPRVSSF | 25 | 273 | 77 |
| 4. | RPRGSSF | 60 | 163 | 37 |
| 5. | RPRNSSF | >500 | ND | 21 |
| 6. | RPRTASF | 20 | 213 | 83 |
| 7. | RPRTGSF | 25 | 233 | 77 |
| 8. | RPRTVSF | 30 | 365 | 89 |
| 9. | RPRTNSF | 30 | 300 | 81 |
| 10. | RPRAASF | 25 | 215 | 77 |
| 11. | RFRGGSF | 105 | 345 | 55 |
| 12. | RPRGASF | 105 | 160 | 37 |
| 13. | RPRAGSF | 49 | 114 | 70 |

The phosphorylated residue is shown in boldface type
The altered residue is underlined.
V (100 μM) is the relative rate of phosphorylation at 0.1 mM peptide relative to peptide 1.
ND = not determined.
*An alanine residue was added to the C-terminal of the peptide RPRTSSP, since we have experienced difficulty in synthesizing peptides terminating in Pro.

TABLE 7.2

Comparison of the Substrate Specificities of RAC-PKα, MAPKAP Kinase-1 and p70S6 Kinase

| | Peptide | Protein kinase Bα Km (mM) | Protein kinase Bα Vmax (U/mg) | MAPKAP kinase-1 Km (mM) | MAPKAP kinase-1 Vmax (U/mg) | p70 S6 kinase Km (mM) | p70 S6 kinase Vmax (U/mg) |
|---|---|---|---|---|---|---|---|
| A | | | | | | | |
| 1. | KKKNRTLSVA | 185 | 270 | 0.2* | 1550* | 33* | 890* |
| 2. | KKRNRTLSVA | 80 | 300 | 0.7* | 1800* | 1.5* | 1520* |
| 3. | KKRNKTLSVA | >500 | ND | 17* | 840* | 34* | 760* |
| 4. | KKRNRTLTV | 388 | 330 | 40* | 270* | 4.8* | 1470* |
| B | | | | | | | |
| 1. | GRPRTSSFAEG | 4 | 250 | 2 | 790 | 3 | 1270 |
| 2. | RPRTSSF | 5 | 260 | 12 | 840 | 125 | 705 |
| 3. | RPRTSTF | 30 | 240 | >500 | >500 | 211 | 590 |
| 4. | RPRAASF | 25 | 215 | 20 | 1020 | >500 | ND |
| 5. | RPRAATF | 25 | 230 | >500 | ND | >500 | ND |

Peptides 1 and 2 are very good substrates for MAPKAP kinase-1 and p70 S6 kinase, and Peptide 3 is a relatively specific substrate for p70 S6 kinase.
*Data reported previously.
ND = not determined.

EXAMPLE 14

Mitogenic Stimulation and Phosphorylation of RAC-PK

The Swiss 3T3 cell line [see {haeck over (S)}u{haeck over (s)}a and Thomas, Proc Natl Acad Sci USA, Vol. 87, pp. 7040-7044 (1990)] is utilized to investigate the possible involvement of RAC-PK in growth factor signaling. Quiescent Swiss 3T3 cells are serum-starved for 24 hours, followed by stimulation with 10% FCS.

(a) Kinase activity is assessed by immunoprecipitating RAC-PK and assaying the kinase using MBP as a substrate. Briefly, cell free extracts are prepared by scraping preconfluent cells into ice-cold TBS, lysing the cells in a buffer containing 50 mM Tris-HCl, pH 7.5, 1 mM EDTA, 1.0% Triton X-100, 2 mM EGTA, 1 mM PMSF, 20.mu.M leupeptin, 20.mu.M aprotenin and 10.mu.M molybdate. Lysates are centrifuged for 15 minutes at 12,000.times.g at 4.degree. C. RAC-PKα is immunoprecipitated from pasorbin-cleared extracts using a rabbit polyclonal antibody specific for the conserved C-terminus (anti-RAC.sup.469-480) [see Jones et al. (1991), supra] raised by injecting rabbits subcutaneously with the peptide FPQFSYSASSTA (SEQ ID NO: 7) coupled to keyhole limpet haemocyanin and purified by precipitation using 50% (NH.sub.4).sub.2SO.sub.4 followed by affinity chromatography on RAC-PK coupled Affigel® 10 column (Bio-Rad). These antisera also recognize the b/AKT2 isoform, because its C-terminus differs from that of RAC-PKα in the last 3 amino acids. RAC-PK activity is assayed as described previously using MBP as substrate. See Jones et al. (1991), supra. The extracts are incubated for 2 hours at 4.degree. C. with the antiserum (2.mu.g/100.mu.L extract) the immunoprecipitates collected using Protein A sepharose and washed with lysis buffer. The protein sepharose beads are resuspended in 100.mu.L of 10 mM Tris-HCl, pH 7.5, 1 mM DTT, 10 pm molybdate and 35.mu.L used for the kinase assay, as follows.

Reaction mixtures in a final volume of 50.mu.L contain 50 mM Tris-HCl, pH 7.5, 10 mM MgCl.sub.2, 1 mM DTT, 1 mM PK inhibitor, PKI peptide, 25 pg of MBP (Sigma), 50.mu.M (.gamma.-32P) ATP (3500 cpm/pmol) and 35.mu.L of immunoprecipitate from cell free extracts or purified fractions of RAC-PK. After incubation at 30.degree. C. for 10, 30 or 60 minutes samples are analyzed by 12% SDS/PAGE followed by autoradiography and quantified by scintillation counting of the phosphorylated MBP bands.

Immunoprecipitated RAC-PK activity is found to be 2- to 4-fold higher in serum-stimulated cells versus quiescent cells. Activation occurs within 5 minutes and kinase activity remains elevated for at least 120 minutes.

(b) Activation coincides with decreased mobility of RAC-PK on SDS-PAGE. In order to determine which forms are present on SDS-PAGE gels, immunoblotting is performed using anti-RAC-PK antisera prepared as above. Cell extracts and immunoprecipitates are resolved by 7.5% SDS-PAGE, transferred to Immobilon-P membranes (Millipore) and incubated with the anti-RAC.sup.469-480 antibody. Detection is performed using Alk phosphatase-conjugated anti-rabbit antibody.

At least 3 different forms can be detected by immunoblot analysis, termed a, b and c. The kinase from quiescent cells migrates as a doublet of the a and b forms and during stimulation a slower migrating form c appears, followed by disappearance of form a. These results suggest that RAC-PK activity is modulated by reversible phosphorylation.

(c) To test this possibility the in vivo effects of phosphatase inhibitors okadaic acid and vanadate on RAC-PK from Swiss 3T3 cells are examined. Cells are serum-starved for 24 hours, followed by stimulation with 1.mu.M okadaic acid, or 0.1 mM vanadate prepared with 0.1 mM H.sub.2O.sub.2 [see Posner et al., J Biol Chem, Vol. 269, pp. 4596-4604 (1994)], optionally in conjunction with 10% FCS. Treatment of cells with okadaic acid, a specific inhibitor of PP2A and PP1, induces a 3-fold increase in RAC-PK activity and decreases electrophoretic mobility. Simultaneously treatment with 1.mu.M okadaic acid and 10% serum causes a 5-fold activation and a larger alteration of the electrophoretic mobility. An 11-fold activation is observed following treatment with 0.1 mM vanadate, which converts the major part of the protein into the slowest-migrating form c.

In order to confirm that multiple electrophoretic mobility forms reflect different phosphorylation states of the kinase, RAC-PK is immunoprecipitated from .sup.32P-labelled quiescent and vanadate-stimulated Swiss 3T3 cells. Swiss 3T3 cells are arrested in phosphate-free DMEM/FCS as described [see {haeck over (S)}u{haeck over (s)}a and Thomas (1990), supra] and serum-starved for 16 hours prior to labelling with [.sup.32P]orthophosphate for 6-10 hours (2 mCi per 15 cm dish). Stimulation is performed 0.1 mM vanadate. Quantification of phosphorylation is performed using the ImageQuant software. Vanadate treatment leads to a 3- to 4-fold increase in phosphorylation, demonstrating that the mobility forms b and c represent phosphorylated RAC-PK.

(d) In order to determine which residues are phosphorylated in activated RAC-PK, phosphoamino acid analysis is carried out on cells labelled as above according to Boyle et al., Methods Enzymol, Vol. 201, pp. 110-149 (1991). The kinase from arrested cells appears phosphorylated mainly on Ser residues, and at low levels on Thr, with a ratio of 12:1. Vanadate stimulation leads to an increase in phosphoserine and, in particular, in phosphothreonine content, reducing the ratio to 4:1. Phosphotyrosine is not detected after vanadate stimulation, either by phosphoamino acid analysis, or by immunoblot analysis using an anti-phosphotyrosine antibody. These results show that RAC-PK is activated by a phosphorylation mechanism. Furthermore, we conclude that RAC-PK activation mediated by vanadate is probably indirect, since vanadate is known to be an inhibitor of tyrosine phosphatases.

EXAMPLE 15

Inactivation of RAC-PK by Protein Phosphatase 2A In Vitro

To confirm that RAC-PK is regulated by phosphorylation the effects of PP2A treatment on the kinase immunoprecipitated from quiescent and vanadate-stimulated Swiss 3T3 cells are investigated. As treatment of cells with 1 mM okadaic acid for 2 hours preferentially inactivates PP2A rather than PP1, RAC-PK is incubated either with the purified PP2A catalytic subunit (PP2Ac), or PP2A dimer consisting of the catalytic and regulatory PR65 subunit (PP2A.sub.2).

Immunoprecipitated RAC-PK is incubated with 0.3 U/mL of porcine muscle PP2Ac or 1.7 U/mL of rabbit muscle PP2A.sub.2 in 30 mL buffer containing 50 mM Tris-HCl, pH 7.5, 1% b-mercaptoethanol, 1 mM MnCl.sub.2, 1 mM benzamidine and 0.5 mM phenylmethylsulfonyl fluoride at 30.degree. C. for 60 minutes (1 U is defined as 1 nmol of Pi released from phosphorylase a per min.). The reactions are stopped by addition of 50 nM calyculin A. The immune complexes formed are washed with 50 mM Tris-HCl, pH 7.5, 1 mM benzamidine, 0.5 mM phenylmethylsulfonyl fluoride and 50 nM calyculin A and RAC-PK is assayed as described above.

Dephosphorylation of the activated RAC-PK in vitro by PP2Ac results in an 84% reduction of kinase activity and concomitant change in electrophoretic mobility, converting it from form c to b. PP2A.sub.2 treatment leads to a 92% reduction of activity and restores the protein mobility on SDS-PAGE to the a/b doublet. These results confirm that the activity changes observed are achieved by a reversible phosphorylation mechanism. Moreover, PP2A is indicated as a potential regulator of RAC-PK activity in vivo.

EXAMPLE 16

RAC-PKα Stimulates p70.sup.s6k Activity

In Swiss 3T3 cells RAC-PK is activated by insulin (4.5-fold), comparable to levels detected for p70.sup.s6k. In contrast, insulin has little or no effect on p42.sup.mapk and p44.sup.mapk in these cells, suggesting that RAC-PK and p70.sup.s6k may reside on the same signaling pathway, which is a different pathway to the MAPK pathway.

In order to investigate this possibility the effects of wortmannin and rapamycin on serum induced activation of the two kinases is examined. Wortmannin, an inhibitor of PI 3-kinase, and immunosuppressant rapamycin block the activation of p70.sup.s6k by affecting the same set of phosphorylation sites.

Stimulation of quiescent Swiss 3T3 fibroblasts leads to a .about.4-fold induction of RAC-PK activity, whereas wortmannin treatment preceding serum stimulation almost completely blocks the activation. On the other hand, rapamycin pretreatment does not exert any significant effect on RAC-PK activation. Wortmannin also blocks the appearance of slowest RAC-PK mobility form that is observed following serum treatment, while rapamycin does not affect RAC-PK mobility. In the same experiment wortmannin and rapamycin pretreatment abolish p70s6k activation.

These results suggest that RAC-PK may lie upstream of p70.sup.s6k on the p70.sup.s6k signaling pathway, which is inhibited upstream of RAC-PK by wortmannin and downstream thereof by rapamycin. To examine this possibility, the regulation of p70.sup.s6k is investigated in a transient cotransfection assay using human 293 cells. RAC-PKα constructs are prepared by ligating the RAC-PKα cDNA [see Jones et al. (1991), supra] in-frame to the initiator methionine, in the mammalian expression vector pECE. The construct is also subcloned into a CMV promoter-driven expression vector. The construct is confirmed by restriction analysis and sequencing. Constructs expressing Myc-tagged p70.sup.s6k are obtained from Dr. G. Thomas, Friederich Miescher Institut, Basel, Switzerland. Constructs are transfected into COS cells using standard procedures. Coexpression of RAC-PKα with p70.sup.s6k-MyC results in a 3.5- and 3-fold increase of basal and insulin-stimulated p70.sup.s6k-Myc activity, respectively.

---

We claim:

1. A RAC-PK polypeptide having the amino acid sequence as set forth in SEQ ID NO:3 which is activated by effecting one or both of the mutations Thr308>Asp and Ser473>Asp.

* * * * *

SEQUENCE LISTING

```
<160> NUMBER OF SEQ ID NOS: 27

<210> SEQ ID NO 1
<211> LENGTH: 1302
<212> TYPE: DNA
<213> ORGANISM: Homo sapiens
<220> FEATURE:
<221> NAME/KEY: mRNA
<222> LOCATION: (1)...(1302)
<223> OTHER INFORMATION: RAC-PK Carboxy-Terminal Binding Protein (CTBP)
<221> NAME/KEY: CDS
<222> LOCATION: (2)...(145)
<223> OTHER INFORMATION: Molecule Type: cDNA to mRNA
<221> NAME/KEY: repeat_region
<222> LOCATION: (981)...(1279)
<223> OTHER INFORMATION: Carboxy-Terminal Binding Protein of RAC-PK

<400> SEQUENCE: 1 g aat tcg gca cga gct aga gca agc gcg gcc ccg cgg ccc gga gcc atg         49
  Asn Ser Ala Arg Ala Arg Ala Ser Ala Ala Pro Arg Pro Gly Ala Met
   1               5                  10                  15 ctg agg agc tgc gcc gcg cgc ctc cgc acg ctg ggg gct ctg tgc cgg         97
Leu Arg Ser Cys Ala Ala Arg Leu Arg Thr Leu Gly Ala Leu Cys Arg
             20                  25                  30 ccg cca gta ggc cgg cgc ctg ccg gaa gcg acc cgc gac ccg agc tga        145
Pro Pro Val Gly Arg Arg Leu Pro Glu Ala Thr Arg Asp Pro Ser  *
         35                  40                  45 ggtcattttc ttctgaggaa gtcattctta aggactgttc tgtccccaac cccagctgga        205
acaaggacct aagactgctc tttgaccagt ttatgaagaa atgtgaagat ggctcctgga        265
aacgtttgcc ttcatataaa cgtacaccta ctgaatggat tcaagacttc aaaacccatt       325
ttcttgaccc aaagcttatg aaagaagaac aaatgtcaca ggcccagctc ttcaccagaa       385
gctttgatga tggcctgggc tttgaatacg tgatgttcta caatgacatt gagaaaagga       445
```

```
tggtttgctt atttcaagga ggcccttacc tggaagacca cctggattca ttcatggagg    505
tgccattgca accatgattg atgctactgt tggtatgtgt gcaatgatgg ctgggggaat    565
cgtcatgact gccaatctca acatcaatta tccccgacct atccctcttt gttctgttgt    625
tatgataaat agccaacttg ataaagttga aggaaggaaa ttttttgttt cctgtaatgt    685
tcagagtgtt gatgagaaga ccctatactc agaggcgaca agcttattat aaagtcgaat    745
cctgctaaaa gtcttgatcg ataaagagtc gtcggtgaac tccatctcat tctcgcccct    805
ccagaagaag gcagttgtcc cccaaatact ctgctccctc actgctgaat cctgtaggga    865
gaagcctgcc aacagtgacc ttccgaaaca gccttctgaa tacaaagagg attcagtttc    925
catcttctca acttttttaac acagaaacac ttcctgcgag actatcgaca actctcgggc    985
caggcgctgt ggctcacacc tgtaatccca gcactttagg aggccgaggc aggcggattg   1045
cctgagctca ggagttgaag atcagtctgg gcaacacgat gaaactccgt ctctactaaa   1105
atacaaaaaa ttatccaggc atggtggcgt acgcctgtag tcccagctac tcaggaggct   1165
gaggcaggag aatcgcttga acccaggagg aagaggttgc agtgagccaa gatcatgcca   1225
catcactcca acctgggcaa cagaacaaga acccatctca acaaacaac aaacaaaaaa    1285 aaaaaaaaaa actcgag                                                  1302
```

<210> SEQ ID NO 2
<211> LENGTH: 47
<212> TYPE: PRT
<213> ORGANISM: Homo sapiens
<220> FEATURE:
<223> OTHER INFORMATION: Carboxy-Terminal-Binding Protein of RAC-PK

<400> SEQUENCE: 2

```
Asn Ser Ala Arg Ala Arg Ala Ser Ala Ala Pro Arg Pro Gly Ala Met
 1               5                  10                  15

Leu Arg Ser Cys Ala Ala Arg Leu Arg Thr Leu Gly Ala Leu Cys Arg
            20                  25                  30

Pro Pro Val Gly Arg Arg Leu Pro Glu Ala Thr Arg Asp Pro Ser
        35                  40                  45
```

<210> SEQ ID NO 3
<211> LENGTH: 2610
<212> TYPE: DNA
<213> ORGANISM: Homo sapiens
<220> FEATURE:
<221> NAME/KEY: CDS
<222> LOCATION: (199)...(1641)
<223> OTHER INFORMATION: Human RAC-PK alpha

<400> SEQUENCE: 3

```
atcctgggac agggcacagg gccatctgtc accaggggct tagggaaggc cgagccagcc     60
tgggtcaaag aagtcaaagg ggctgcctgg aggaggcagc ctgtcagctg gtgcatcaga    120
ggctgtggcc aggccagctg ggctcgggga cgccagcct gagaggagcg cgtgagcgtc    180
gcgggagcct cgggcacc atg agc gac gtg gct att gtg aag gag ggt tgg    231
                    Met Ser Asp Val Ala Ile Val Lys Glu Gly Trp
                     1               5                  10 ctg cac aaa cga ggg gag tac atc aag acc tgg cgg cca cgc tac ttc    279
Leu His Lys Arg Gly Glu Tyr Ile Lys Thr Trp Arg Pro Arg Tyr Phe
            15                  20                  25 ctc ctc aag aat gat ggc acc ttc att ggc tac aag gag cgg ccg cag    327
Leu Leu Lys Asn Asp Gly Thr Phe Ile Gly Tyr Lys Glu Arg Pro Gln
        30                  35                  40
```

```
gat gtg gac caa cgt gag gct ccc ctc aac aac ttc tct gtg gcg cag      375
Asp Val Asp Gln Arg Glu Ala Pro Leu Asn Asn Phe Ser Val Ala Gln
     45                  50                  55 tgc cag ctg atg aag acg gag cgg ccc cgg ccc aac acc ttc atc atc      423
Cys Gln Leu Met Lys Thr Glu Arg Pro Arg Pro Asn Thr Phe Ile Ile
 60                  65                  70                  75 cgc tgc ctg cag tgg acc act gtc atc gaa cgc acc ttc cat gtg gag      471
Arg Cys Leu Gln Trp Thr Thr Val Ile Glu Arg Thr Phe His Val Glu
                 80                  85                  90 act cct gag gag cgg gag gag tgg aca acc gcc atc cag act gtg gct      519
Thr Pro Glu Glu Arg Glu Glu Trp Thr Thr Ala Ile Gln Thr Val Ala
             95                 100                 105 gac ggc ctc aag aag cag gag gag gag atg gac ttc cgg tcg ggc          567
Asp Gly Leu Lys Lys Gln Glu Glu Glu Met Asp Phe Arg Ser Gly
         110                 115                 120 tca ccc agt gac aac tca ggg gct gaa gag atg gag gtg tcc ctg gcc      615
Ser Pro Ser Asp Asn Ser Gly Ala Glu Glu Met Glu Val Ser Leu Ala
125                 130                 135 aag ccc aag cac cgc gtg acc atg aac gag ttt gag tac ctg aag ctg      663
Lys Pro Lys His Arg Val Thr Met Asn Glu Phe Glu Tyr Leu Lys Leu
140                 145                 150                 155 ctg ggc aag ggc act ttc ggc aag gtg atc ctg gtg aag gag aag gcc      711
Leu Gly Lys Gly Thr Phe Gly Lys Val Ile Leu Val Lys Glu Lys Ala
                 160                 165                 170 aca ggc cgc tac tac gcc atg aag atc ctc aag aag gaa gtc atc gtg      759
Thr Gly Arg Tyr Tyr Ala Met Lys Ile Leu Lys Lys Glu Val Ile Val
             175                 180                 185 gcc aag gac gag gtg gcc cac aca ctc acc gag aac cgc gtc ctg cag      807
Ala Lys Asp Glu Val Ala His Thr Leu Thr Glu Asn Arg Val Leu Gln
         190                 195                 200 aac tcc agg cac ccc ttc ctc aca gcc ctg aag tac tct ttc cag acc      855
Asn Ser Arg His Pro Phe Leu Thr Ala Leu Lys Tyr Ser Phe Gln Thr
205                 210                 215 cac gac cgc ctc tgc ttt gtc atg gag tac gcc aac ggg ggc gag ctg      903
His Asp Arg Leu Cys Phe Val Met Glu Tyr Ala Asn Gly Gly Glu Leu
220                 225                 230                 235 ttc ttc cac ctg tcc cgg gaa cgt gtg ttc tcc gag gac cgg gcc cgc      951
Phe Phe His Leu Ser Arg Glu Arg Val Phe Ser Glu Asp Arg Ala Arg
                 240                 245                 250 ttc tat ggc gct gag att gtg tca gcc ctg gac tac ctg cac tcg gag      999
Phe Tyr Gly Ala Glu Ile Val Ser Ala Leu Asp Tyr Leu His Ser Glu
             255                 260                 265 aag aac gtg gtg tac cgg gac ctc aag ctg gag aac ctc atg ctg gac     1047
Lys Asn Val Val Tyr Arg Asp Leu Lys Leu Glu Asn Leu Met Leu Asp
         270                 275                 280 aag gac ggg cac att aag atc aca gac ttc ggg ctg tgc aag gag ggg     1095
Lys Asp Gly His Ile Lys Ile Thr Asp Phe Gly Leu Cys Lys Glu Gly
285                 290                 295 atc aag gac ggt gcc acc atg aag acc ttt tgc ggc aca cct gag tac     1143
Ile Lys Asp Gly Ala Thr Met Lys Thr Phe Cys Gly Thr Pro Glu Tyr
300                 305                 310                 315 ctg gcc ccc gag gtg ctg gag gac aat gac tac ggc cgt gca gtg gac     1191
Leu Ala Pro Glu Val Leu Glu Asp Asn Asp Tyr Gly Arg Ala Val Asp
                 320                 325                 330 tgg tgg ggg ctg ggc gtg gtc atg tac gag atg atg tgc ggt cgc ctg     1239
Trp Trp Gly Leu Gly Val Val Met Tyr Glu Met Met Cys Gly Arg Leu
             335                 340                 345 ccc ttc tac aac cag gac cat gag aag ctt ttt gag ctc atc ctc atg     1287
Pro Phe Tyr Asn Gln Asp His Glu Lys Leu Phe Glu Leu Ile Leu Met
         350                 355                 360
```

```
gag gag atc cgc ttc ccg cgc acg ctt ggt ccc gag gcc aag tcc ttg   1335
Glu Glu Ile Arg Phe Pro Arg Thr Leu Gly Pro Glu Ala Lys Ser Leu
    365                 370                 375 ctt tca ggg ctg ctc aag aag gac ccc aag cag agg ctt ggc ggg ggc   1383
Leu Ser Gly Leu Leu Lys Lys Asp Pro Lys Gln Arg Leu Gly Gly Gly
380                 385                 390                 395 tcc gag gac gcc aag gag atc atg cag cat cgc ttc ttt gcc ggt atc   1431
Ser Glu Asp Ala Lys Glu Ile Met Gln His Arg Phe Phe Ala Gly Ile
                400                 405                 410 gtg tgg cag cac gtg tac gag aag aag ctc agc cca ccc ttc aag ccc   1479
Val Trp Gln His Val Tyr Glu Lys Lys Leu Ser Pro Pro Phe Lys Pro
            415                 420                 425 cag gtc acg tcg gag act gac acc agg tat ttt gat gag gag ttc acg   1527
Gln Val Thr Ser Glu Thr Asp Thr Arg Tyr Phe Asp Glu Glu Phe Thr
        430                 435                 440 gcc cag atg atc acc atc aca cca cct gac caa gat gac agc atg gag   1575
Ala Gln Met Ile Thr Ile Thr Pro Pro Asp Gln Asp Asp Ser Met Glu
    445                 450                 455 tgt gtg gac agc gag cgc agg ccc cac ttc ccc cag ttc tcc tac tcg   1623
Cys Val Asp Ser Glu Arg Arg Pro His Phe Pro Gln Phe Ser Tyr Ser
460                 465                 470                 475 gcc agc agc acg gcc tga ggcggcggtg gactgcgctg gacgatagct          1671
Ala Ser Ser Thr Ala *
                480 tggagggatg gagaggcggc ctcgtgccat gatctgtatt taatggtttt tatttctcgg   1731 gtgcatttga gagaagccac gctgtcctct cgagcccaga tggaaagacg ttttttgtgct  1791 gtgggcagca ccctcccccg cagcggggta gggaagaaaa ctatcctgcg ggttttaatt   1851 tatttcatcc agtttgttct ccgggtgtgg cctcagccct cagaacaatc cgattcacgt   1911 agggaaatgt taaggacttc tacagctatg cgcaatgtgg cattgggggg ccgggcaggt   1971 cctgcccatg tgtcccctca ctctgtcagc cagccgccct gggctgtctg tcaccagcta   2031 tctgtcatct ctctggggcc ctgggcctca gttcaacctg gtggcaccag atgcaacctc   2091 actatggtat gctggccagc accctctcct ggggggtggca ggcacacagc agccccccag  2151 cactaaggcc gtgtctctga ggacgtcatc ggaggctggg cccctgggat gggaccaggg   2211 atgggggatg ggccagggtt tacccagtgg gacagaggag caaggtttaa atttgttatt   2271 gtgtattatg ttgttcaaat gcattttggg ggttttttaat ctttgtgaca ggaaagcccct 2331 ccccccttccc cttctgtgtc acagttcttg gtgactgtcc caccggagcc tccccctcag  2391 atgatctctc cacggtagca cttgaccttt tcgacgctta acctttccgc tgtcgcccca   2451 ggccctccct gactccctgt ggggggtggcc atccctgggc ccctccacgc tcctggcca   2511 gacgctgccg ctgccgctgc caccggcgct ttttttacaa cattcaactt tagtattttt   2571 actattataa tataatatgg aaccttccct ccaaattct                         2610
```

<210> SEQ ID NO 4
<211> LENGTH: 480
<212> TYPE: PRT
<213> ORGANISM: Homo sapiens
<220> FEATURE:
<221> NAME/KEY: PEPTIDE
<222> LOCATION: (1)...(480)
<223> OTHER INFORMATION: Human RAC-PK alpha

<400> SEQUENCE: 4

```
Met Ser Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
```

-continued

```
                20                  25                  30
Gly Thr Phe Ile Gly Tyr Lys Glu Arg Pro Gln Asp Val Asp Gln Arg
                35                  40                  45
Glu Ala Pro Leu Asn Asn Phe Ser Val Ala Gln Cys Gln Leu Met Lys
 50                  55                  60
Thr Glu Arg Pro Arg Pro Asn Thr Phe Ile Ile Arg Cys Leu Gln Trp
 65                  70                  75                  80
Thr Thr Val Ile Glu Arg Thr Phe His Val Thr Pro Glu Glu Arg
                 85                  90                  95
Glu Glu Trp Thr Thr Ala Ile Gln Thr Val Ala Asp Gly Leu Lys Lys
                100                 105                 110
Gln Glu Glu Glu Met Asp Phe Arg Ser Gly Ser Pro Ser Asp Asn
                115                 120                 125
Ser Gly Ala Glu Glu Met Glu Val Ser Leu Ala Lys Pro Lys His Arg
130                 135                 140
Val Thr Met Asn Glu Phe Glu Tyr Leu Lys Leu Leu Gly Lys Gly Thr
145                 150                 155                 160
Phe Gly Lys Val Ile Leu Val Lys Glu Lys Ala Thr Gly Arg Tyr Tyr
                165                 170                 175
Ala Met Lys Ile Leu Lys Lys Glu Val Ile Val Ala Lys Asp Glu Val
                180                 185                 190
Ala His Thr Leu Thr Glu Asn Arg Val Leu Gln Asn Ser Arg His Pro
                195                 200                 205
Phe Leu Thr Ala Leu Lys Tyr Ser Phe Gln Thr His Asp Arg Leu Cys
                210                 215                 220
Phe Val Met Glu Tyr Ala Asn Gly Gly Glu Leu Phe Phe His Leu Ser
225                 230                 235                 240
Arg Glu Arg Val Phe Ser Glu Asp Arg Ala Arg Phe Tyr Gly Ala Glu
                245                 250                 255
Ile Val Ser Ala Leu Asp Tyr Leu His Ser Lys Asn Val Val Tyr
                260                 265                 270
Arg Asp Leu Lys Leu Glu Asn Leu Met Leu Asp Lys Asp Gly His Ile
                275                 280                 285
Lys Ile Thr Asp Phe Gly Leu Cys Lys Glu Gly Ile Lys Asp Gly Ala
                290                 295                 300
Thr Met Lys Thr Phe Cys Gly Thr Pro Glu Tyr Leu Ala Pro Glu Val
305                 310                 315                 320
Leu Glu Asp Asn Asp Tyr Gly Arg Ala Val Asp Trp Trp Gly Leu Gly
                325                 330                 335
Val Val Met Tyr Glu Met Met Cys Gly Arg Leu Pro Phe Tyr Asn Gln
                340                 345                 350
Asp His Glu Lys Leu Phe Glu Leu Ile Leu Met Glu Glu Ile Arg Phe
                355                 360                 365
Pro Arg Thr Leu Gly Pro Glu Ala Lys Ser Leu Leu Ser Gly Leu Leu
                370                 375                 380
Lys Lys Asp Pro Lys Gln Arg Leu Gly Gly Gly Ser Glu Asp Ala Lys
385                 390                 395                 400
Glu Ile Met Gln His Arg Phe Phe Ala Gly Ile Val Trp Gln His Val
                405                 410                 415
Tyr Glu Lys Lys Leu Ser Pro Pro Phe Lys Pro Gln Val Thr Ser Glu
                420                 425                 430
Thr Asp Thr Arg Tyr Phe Asp Glu Glu Phe Thr Ala Gln Met Ile Thr
                435                 440                 445
```

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Ser Thr Ala
465                 470                 475                 480

<210> SEQ ID NO 5
<211> LENGTH: 11
<212> TYPE: PRT
<213> ORGANISM: Homo sapiens
<220> FEATURE:
<221> NAME/KEY: PEPTIDE
<222> LOCATION: (1)...(11)
<223> OTHER INFORMATION: Substrate for measuring RAC-PK activity
      ("Crosstide")

<400> SEQUENCE: 5

Gly Arg Pro Arg Thr Ser Ser Phe Ala Glu Gly
1               5                   10

<210> SEQ ID NO 6
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 6

Arg Pro Arg Ala Ala Thr Cys
1               5

<210> SEQ ID NO 7
<211> LENGTH: 12
<212> TYPE: PRT
<213> ORGANISM: Homo sapiens
<220> FEATURE:
<221> NAME/KEY: PEPTIDE
<222> LOCATION: (1)...(12)
<223> OTHER INFORMATION: Antigen for raising a polyclonal anti-RAC
      rabbit antiserum

<400> SEQUENCE: 7

Phe Pro Gln Phe Ser Tyr Ser Ala Ser Ser Thr Ala
1               5                   10

<210> SEQ ID NO 8
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 8

Arg Pro Arg Ala Ala Ser Phe
1               5

<210> SEQ ID NO 9
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 9

```
Arg Pro Arg Thr Ser Ser Phe
1               5

<210> SEQ ID NO 10
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 10

Arg Pro Arg Gly Gly Ser Phe
1               5

<210> SEQ ID NO 11
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 11

Arg Pro Arg Ala Gly Ser Phe
1               5

<210> SEQ ID NO 12
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 12

Arg Pro Arg Gly Ala Ser Phe
1               5

<210> SEQ ID NO 13
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Substrate for measuring RAC-PK activity

<400> SEQUENCE: 13

Lys Lys Lys Asn Arg Thr Leu Ser Val Ala
1               5                   10

<210> SEQ ID NO 14
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Substrate for measuring RAC-PK activity

<400> SEQUENCE: 14

Lys Lys Arg Asn Arg Thr Leu Ser Val Ala
1               5                   10

<210> SEQ ID NO 15
```

```
<211> LENGTH: 9
<212> TYPE: PRT
<213> ORGANISM: Homo sapiens
<220> FEATURE:
<221> NAME/KEY: PEPTIDE
<222> LOCATION: (1)...(9)
<223> OTHER INFORMATION: Substrate for measuring RAC-PK activity

<400> SEQUENCE: 15

Lys Lys Arg Asn Arg Thr Leu Thr Val
 1               5

<210> SEQ ID NO 16
<211> LENGTH: 7
<212> TYPE: PRT
<213> ORGANISM: Homo sapiens
<220> FEATURE:
<221> NAME/KEY: PEPTIDE
<222> LOCATION: (1)...(7)
<223> OTHER INFORMATION: Substrate for measuring RAC-PK activity

<400> SEQUENCE: 16

Arg Pro Arg Ala Ala Thr Phe
 1               5

<210> SEQ ID NO 17
<211> LENGTH: 9
<212> TYPE: PRT
<213> ORGANISM: Homo sapiens
<220> FEATURE:
<221> NAME/KEY: PEPTIDE
<222> LOCATION: (1)...(9)
<223> OTHER INFORMATION: Substrate for measuring RAC-PK activity

<400> SEQUENCE: 17

Gly Arg Ala Arg Thr Ser Ser Phe Ala
 1               5

<210> SEQ ID NO 18
<211> LENGTH: 6
<212> TYPE: PRT
<213> ORGANISM: Homo sapiens
<220> FEATURE:
<221> NAME/KEY: PEPTIDE
<222> LOCATION: (1)...(6)
<223> OTHER INFORMATION: Antigen for raising monoclonal anti-RAC
      antibody

<400> SEQUENCE: 18

Glu Phe Met Pro Met Glu
 1               5

<210> SEQ ID NO 19
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Antigen for raising monoclonal anti-RAC
      antibody

<400> SEQUENCE: 19

Glu Gln Lys Leu Ile Ser Glu Glu Asp Leu
 1               5                  10

<210> SEQ ID NO 20
<211> LENGTH: 55
<212> TYPE: DNA
<213> ORGANISM: Homo sapiens
```

-continued

```
<220> FEATURE:
<221> NAME/KEY: primer_bind
<222> LOCATION: (1)...(55)
<223> OTHER INFORMATION: Oligonucleotide Primers

<400> SEQUENCE: 20
gcggagatct gccaccatgg agttcatgcc catggagtca gggcggccca gaacc      55

<210> SEQ ID NO 21
<211> LENGTH: 27
<212> TYPE: DNA
<213> ORGANISM: Homo sapiens
<220> FEATURE:
<221> NAME/KEY: primer_bind
<222> LOCATION: (1)...(27)
<223> OTHER INFORMATION: Oligonucleotide Primers

<400> SEQUENCE: 21
gcggtccgga acatagtcca gcaccag                                     27

<210> SEQ ID NO 22
<211> LENGTH: 15
<212> TYPE: PRT
<213> ORGANISM: Homo sapiens
<220> FEATURE:
<221> NAME/KEY: PEPTIDE
<222> LOCATION: (1)...(15)
<223> OTHER INFORMATION: Antigen for raising sheep polyclonal anti-RAC
      antibody

<400> SEQUENCE: 22

Arg Pro His Phe Pro Gln Phe Ser Tyr Ser Ala Ser Gly Thr Ala
1               5                   10                  15

<210> SEQ ID NO 23
<211> LENGTH: 16
<212> TYPE: PRT
<213> ORGANISM: Homo sapiens
<220> FEATURE:
<221> NAME/KEY: PEPTIDE
<222> LOCATION: (1)...(16)
<223> OTHER INFORMATION: Antigen for purifying monoclonal anti-RAC
      antibody

<400> SEQUENCE: 23

Met Thr Ser Ala Leu Ala Thr Met Arg Val Asp Tyr Glu Gln Ile Lys
1               5                   10                  15

<210> SEQ ID NO 24
<211> LENGTH: 13
<212> TYPE: PRT
<213> ORGANISM: Homo sapiens
<220> FEATURE:
<221> NAME/KEY: PEPTIDE
<222> LOCATION: (1)...(13)
<223> OTHER INFORMATION: Antigen for purifying monoclonal anti-RAC
      antibody

<400> SEQUENCE: 24

Arg Pro Arg His Phe Pro Gln Phe Ser Tyr Ser Ala Ser
1               5                   10

<210> SEQ ID NO 25
<211> LENGTH: 9
<212> TYPE: PRT
<213> ORGANISM: Homo sapiens
<220> FEATURE:
<221> NAME/KEY: PEPTIDE
<222> LOCATION: (1)...(8)
<223> OTHER INFORMATION: Substrate for measuring RAC-PK activity
```

```
<400> SEQUENCE: 25

Tyr Pro Tyr Asp Val Pro Asp Tyr Ala
 1               5

<210> SEQ ID NO 26
<211> LENGTH: 20
<212> TYPE: PRT
<213> ORGANISM: Homo sapiens
<220> FEATURE:
<221> NAME/KEY: PEPTIDE
<222> LOCATION: (1)...(20)
<223> OTHER INFORMATION: Substrate for measuring RAC-PK activity

<400> SEQUENCE: 26

Thr Thr Tyr Ala Asp Phe Ile Ala Ser Gly Arg Thr Gly Arg Arg Asn
 1               5                  10                  15

Ala Ile His Asp
            20

<210> SEQ ID NO 27
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Substrate for measuring RAC-PK activity

<400> SEQUENCE: 27

Lys Lys Leu Asn Arg Thr Leu Ser Val Ala
 1               5                  10
```